(12) United States Patent
Hoeflich et al.

(10) Patent No.: US 9,150,548 B2
(45) Date of Patent: Oct. 6, 2015

(54) COMBINATIONS OF AKT INHIBITOR COMPOUNDS AND VEMURAFENIB, AND METHODS OF USE

(75) Inventors: Klaus Hoeflich, South San Francisco, CA (US); Mark Merchant, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/009,310

(22) PCT Filed: Mar. 30, 2012

(86) PCT No.: PCT/US2012/031665
§ 371 (c)(1),
(2), (4) Date: Oct. 1, 2013

(87) PCT Pub. No.: WO2012/135750
PCT Pub. Date: Oct. 4, 2012

(65) Prior Publication Data
US 2014/0275106 A1  Sep. 18, 2014

Related U.S. Application Data

(60) Provisional application No. 61/470,803, filed on Apr. 1, 2011, provisional application No. 61/470,624, filed on Apr. 1, 2011.

(51) Int. Cl.
| | |
|---|---|
| *A61K 31/497* | (2006.01) |
| *A61K 31/44* | (2006.01) |
| *C07D 403/12* | (2006.01) |
| *C07D 239/70* | (2006.01) |
| *A61K 31/437* | (2006.01) |
| *A61K 31/496* | (2006.01) |
| *A61K 31/517* | (2006.01) |
| *A61K 31/58* | (2006.01) |
| *A61K 31/282* | (2006.01) |
| *A61K 31/337* | (2006.01) |
| *A61K 31/4188* | (2006.01) |
| *A61K 31/4745* | (2006.01) |
| *A61K 31/513* | (2006.01) |
| *A61K 31/519* | (2006.01) |
| *A61K 31/704* | (2006.01) |
| *A61K 39/395* | (2006.01) |
| *A61K 39/00* | (2006.01) |

(52) U.S. Cl.
CPC ............ *C07D 403/12* (2013.01); *A61K 31/282* (2013.01); *A61K 31/337* (2013.01); *A61K 31/4188* (2013.01); *A61K 31/437* (2013.01); *A61K 31/4745* (2013.01); *A61K 31/496* (2013.01); *A61K 31/513* (2013.01); *A61K 31/517* (2013.01); *A61K 31/519* (2013.01); *A61K 31/58* (2013.01); *A61K 31/704* (2013.01); *A61K 39/3955* (2013.01); *C07D 239/70* (2013.01); *A61K 2039/505* (2013.01)

(58) Field of Classification Search
CPC .... A61K 31/437; A61K 31/496; A61K 31/44
USPC ............. 514/252.12, 252.13, 252.14, 252.16, 514/299, 300
See application file for complete search history.

(56) References Cited

U.S. PATENT DOCUMENTS

| | | | |
|---|---|---|---|
| 3,885,035 A | 5/1975 | Simpson | |
| 3,956,495 A | 5/1976 | Lacefield | |
| 3,966,936 A | 6/1976 | Cronin et al. | |

(Continued)

FOREIGN PATENT DOCUMENTS

| | | |
|---|---|---|
| EP | 194161 | 9/1986 |
| JP | 2004-512277 | 4/2004 |

(Continued)

OTHER PUBLICATIONS

American Cancer Society, "Cancer Types", http://www.cancer.org/cancer/showallcancertypes/index, 2 pages (2013).
Baade et al., "One in four cancers preventable—but first we need the willpower", The Conversation, http://theconverstion.com/one-in-four-cancers-preventable-but-first-we-need-the-willpower-5850, 3 pages (Mar. 19, 2012).
Blake et al., "Discovery and Preclinical Pharmacology of a Selective ATP—Competitive Akt Inhibitor (GDC-0068) for the Treatment of Human Tumors", *Journal of Medicincal Chemistry*, 55, 8110-8127, 2012.
Bock et al., "Managing drug resistance in cancer: lessons from HIV therapy", Nature.com, vol. 12, 494-501 (2012).

(Continued)

*Primary Examiner* — My-Chau T Tran
(74) *Attorney, Agent, or Firm* — Viksnins Harris & Padys PLLP

(57) ABSTRACT

The invention provides a combination of a) a compound of Formula Ia: [insert Formula Ia], or a pharmaceutically acceptable salt thereof, and b) vemurafenib or a pharmaceutically acceptable salt thereof for the prophylactic or therapeutic treatment of a hyperproliferative disorder, such as cancer.

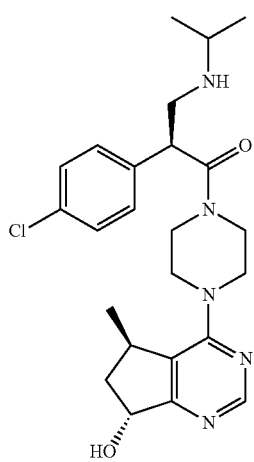

Ia

14 Claims, 43 Drawing Sheets

(56) References Cited

U.S. PATENT DOCUMENTS

| | | | |
|---|---|---|---|
| 4,060,615 A | 11/1977 | Matier et al. | |
| 4,352,928 A | 10/1982 | Hiranuma et al. | |
| 4,749,704 A | 6/1988 | Iwata et al. | |
| 4,871,739 A | 10/1989 | Baldwin et al. | |
| 4,889,856 A | 12/1989 | Tolman et al. | |
| 4,959,368 A | 9/1990 | Awaya et al. | |
| 4,994,464 A | 2/1991 | Tolman et al. | |
| 5,051,412 A | 9/1991 | Macor | |
| 5,525,625 A | 6/1996 | Bridges et al. | |
| 5,563,152 A | 10/1996 | Kulagowski et al. | |
| 5,610,303 A | 3/1997 | Kimura et al. | |
| 5,747,498 A | 5/1998 | Schnur et al. | |
| 5,750,531 A | 5/1998 | Lee et al. | |
| 5,750,545 A | 5/1998 | Akahoshi et al. | |
| 5,817,671 A | 10/1998 | Filla et al. | |
| 6,310,060 B1 | 10/2001 | Barrett et al. | |
| 6,423,716 B1 | 7/2002 | Matsuno et al. | |
| 6,469,004 B1 | 10/2002 | Barrett et al. | |
| 6,506,798 B1 | 1/2003 | Barrett et al. | |
| 6,627,628 B1 | 9/2003 | Schindler et al. | |
| 6,831,175 B2 | 12/2004 | Li et al. | |
| 7,041,687 B2 | 5/2006 | Binch et al. | |
| 7,067,664 B1 | 6/2006 | Chen | |
| 7,115,741 B2 | 10/2006 | Levy et al. | |
| 7,125,880 B1 | 10/2006 | Chen | |
| 7,223,738 B2 | 5/2007 | Bilodeau et al. | |
| 7,223,767 B2 | 5/2007 | Clark et al. | |
| 7,294,332 B2 | 11/2007 | Dugan | |
| 7,504,509 B2 | 3/2009 | Ibrahim et al. | |
| 7,863,288 B2 * | 1/2011 | Ibrahim et al. | 514/300 |
| 7,947,690 B2 | 5/2011 | Yonetoku et al. | |
| 7,960,545 B2 | 6/2011 | Prasad et al. | |
| 8,003,651 B2 | 8/2011 | Mitchell et al. | |
| 8,063,050 B2 * | 11/2011 | Mitchell et al. | 514/252.16 |
| 8,143,271 B2 * | 3/2012 | Ibrahim et al. | 514/300 |
| 8,247,423 B2 | 8/2012 | Estok et al. | |
| 8,846,681 B2 | 9/2014 | Mitchell et al. | |
| 8,853,199 B2 | 10/2014 | Mitchell et al. | |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0199511 A1 | 10/2003 | Li et al. | |
| 2003/0216460 A1 | 11/2003 | Wallace et al. | |
| 2003/0232869 A1 | 12/2003 | Wallace et al. | |
| 2004/0053933 A1 | 3/2004 | Pontillo et al. | |
| 2004/0102360 A1 | 5/2004 | Barnett et al. | |
| 2004/0116710 A1 | 6/2004 | Wallace et al. | |
| 2004/0176400 A1 | 9/2004 | Capelli et al. | |
| 2005/0059687 A1 | 3/2005 | Makings et al. | |
| 2005/0130954 A1 | 6/2005 | Mitchell et al. | |
| 2005/0182061 A1 | 8/2005 | Green et al. | |
| 2006/0025074 A1 | 2/2006 | Liang et al. | |
| 2006/0062400 A1 | 3/2006 | Chia-Chun | |
| 2007/0004708 A1 | 1/2007 | Andreotti et al. | |
| 2007/0027156 A1 | 2/2007 | Nakai et al. | |
| 2007/0135466 A1 | 6/2007 | Ledeboer et al. | |
| 2008/0051399 A1 | 2/2008 | Mitchell et al. | |
| 2008/0076774 A1 | 3/2008 | Anand et al. | |
| 2008/0131526 A1 | 6/2008 | Sebti et al. | |
| 2008/0188482 A1 | 8/2008 | Rice et al. | |
| 2009/0137595 A1 | 5/2009 | Sakai et al. | |
| 2009/0258364 A1 | 10/2009 | Goel et al. | |
| 2010/0069357 A1 | 3/2010 | Bergeron et al. | |
| 2010/0256365 A1 | 10/2010 | Ibrahim et al. | |
| 2012/0232055 A1 * | 9/2012 | Mitchell et al. | 514/210.21 |
| 2014/0221386 A1 | 8/2014 | Nannini et al. | |
| 2014/0256691 A1 | 9/2014 | Nannini et al. | |
| 2014/0349996 A1 | 11/2014 | Mitchell et al. | |
| 2014/0349997 A1 | 11/2014 | Mitchell et al. | |

FOREIGN PATENT DOCUMENTS

| | | |
|---|---|---|
| JP | 2005-521659 | 7/2005 |
| JP | 2005-525303 | 8/2005 |
| WO | WO 95/03286 | 2/1995 |
| WO | WO 98/43960 | 10/1998 |
| WO | WO 99/01421 | 1/1999 |
| WO | WO 99/01426 | 1/1999 |
| WO | WO 00/40235 | 7/2000 |
| WO | WO 00/40237 | 7/2000 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/68201 | 11/2000 |
| WO | WO 01/05390 | 1/2001 |
| WO | WO 01/05391 | 1/2001 |
| WO | WO 01/05392 | 1/2001 |
| WO | WO 01/05393 | 1/2001 |
| WO | WO 01/68619 | 9/2001 |
| WO | WO 01/75160 | 10/2001 |
| WO | WO 02/06213 | 1/2002 |
| WO | WO 02/18319 | 3/2002 |
| WO | WO 02/22604 | 3/2002 |
| WO | WO 02/44166 | 6/2002 |
| WO | WO 02/083139 | 10/2002 |
| WO | WO 03/022214 | 3/2003 |
| WO | WO 03/049678 | 6/2003 |
| WO | WO 03/062225 | 7/2003 |
| WO | WO 03/064397 | 8/2003 |
| WO | WO 03/077855 | 9/2003 |
| WO | WO 03/077914 | 9/2003 |
| WO | WO 03/086279 | 10/2003 |
| WO | WO 03/086394 | 10/2003 |
| WO | WO 03/086403 | 10/2003 |
| WO | WO 03/086404 | 10/2003 |
| WO | WO 03/094918 | 11/2003 |
| WO | WO 2004/041162 | 5/2004 |
| WO | WO 2004/048343 | 6/2004 |
| WO | WO 2004/096130 | 11/2004 |
| WO | WO 2005/014558 | 2/2005 |
| WO | WO 2005/094322 | 10/2005 |
| WO | WO 2005/105780 | 11/2005 |
| WO | WO 2005/117909 | 12/2005 |
| WO | WO 2006/000589 | 1/2006 |
| WO | WO 2006/046023 | 5/2006 |
| WO | WO 2006/071819 | 7/2006 |
| WO | WO 2006/090261 | 8/2006 |
| WO | WO 2006/094230 | 9/2006 |
| WO | WO 2006/136830 | 12/2006 |
| WO | WO 2007/042298 | 4/2007 |
| WO | WO 2007/077961 | 7/2007 |
| WO | WO 2007/125320 | 11/2007 |
| WO | WO 2008/003697 | 1/2008 |
| WO | WO 2008/003958 | 1/2008 |
| WO | WO 2008/003978 | 1/2008 |
| WO | WO 2008/005511 | 1/2008 |
| WO | WO 2008/005964 | 1/2008 |
| WO | WO 2008/006032 | 1/2008 |
| WO | WO 2008/006039 | 1/2008 |
| WO | WO 2008/006040 | 1/2008 |
| WO | WO 2008/012635 | 1/2008 |
| WO | WO 2008/024484 | 2/2008 |
| WO | WO 2008/094321 | 8/2008 |

OTHER PUBLICATIONS

Buck et al., "Rapamycin synergizes with the epidermal growth factor receptor inhibitor erlotinib in non-small-cell lung, pancreatic, colon, and breast tumors", *Mol. Cancer Ther.* 5(11), 267-2684 (2006).

Carver et al., "Reciprocal Feedback Regulation of PI3K and Androgen Receptor Signaling in PTEN-Deficient Prostate Cancer", *Cancer Cell*, vol. 19 (5), 575-586 (2011).

Cohen, "Protein kinases—the major drug targets of the twenty-first century?" *Nature Rev. Drug Discovery 1*, 309-315 (2002).

Davies et al., "Catalytic Enantioselective Synthesis of β-2-Amino Acids", *Angew. Chem.* 114 (12), 2301-2303 (2002).

D'Souza et al., "(R)—(+)—3-Amino-2-phenylpropanoic Acid: a Revised Absolute Configureation based on an Enantioselective Synthesis and an X-Ray Crystal Structure of the Salt with (1S)—(+)—Camphor-10-sulfonic Acid", *J. Chem. Soc. Perkins Trans. 1*, 2 pages, (1995).

Office Action issued by the Columbian Patent Office for CL App. No. 09-010.508, and translation thereof Mar. 25, 2013 (mailing date) 14 pages.

Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate" American Society of Clinical Oncology (ASCO) Annual Meeting, Chicago, IL, Jun. 1-5, 2012, Poster TPS2616, 1 page.

Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate", J. Clin. Oncology (Meeting Abstracts), 30(suppl.), abstract: TPS2616, 3 pages, 2012.

Greco et al., "The Search for Cytotoxic Synergy Between Anticancer Agents: a Case of Dorothy7 and the Ruby Slippers?", *Journal of the Nat. Cancer Institute*, vol. 88 (11), 699-700 (1996).

Grothey, "Focus on Targeted Therapies for Colorectal Cancer—Future Directions: An Expert Interview with Dr. Axel Grothey", Medscape Oncology vol. 9 (2), 1-3 (2006).

Li, Qun "Expert Opinion: Recent Progress in the Discovery of Akt Inhibitors as Anticancer Agents", *Informa Healthcare* 17 (9), 1077-1130 (2007).

Lin, Kui, "GDC-0068, A Novel, Selective, ATP-Competitive Inhibitor of AKT", In: Proceedings of the 102nd Annual Meeting of the American Association for Cancer Research, Apr. 2-6, 2011, Orlando, Florida, Philadelphia (PA): AACR; 2011, Presentation No. DDT02-01, 1 page abstract, and 30 pages of the corresponding presentation given Apr. 3, 2011.

Lin et al., "An ATP-Site On-Off Switch That Restricts Phosphatase Accessibility of Akt", Sci. Signal., 5(223), ra37, pp. 1-10 (2012).

List of Cancer Chemotherapy Drugs, Navigating Cancer, http://www.navigatingcancer.com/library/all/chemotherapy_drugs, 6 pages (2013).

Neidle, "18.3 Failure Modes in Clinical Development", *Cancer Drug Design and Discovery*, (Elsevier/Academic Press), pp. 427-431 (2008).

Ohno, S., et al., "Synthesis and Hypoglycemic Activity of 7,8-Dihydro-6H-thiopyrano[3,2-d]pyrimidine Derivatives and Related Compounds", Chem. Pharm. Bull., 1986, 34(10), 4150-4165.

Patent Cooperation Treaty, International Searching Authority, Search Report and Written Opinion for PCT/US2012/31720, 11 pages Jun. 27, 2012.

Patent Cooperation Treaty, International Searching Authority, Search Report and Written Opinion for PCT/US2012/31671, 10 pages Jun. 28, 2012.

Patent Cooperation Treaty, International Searching Authority, Search Report and Written Opinion for PCT/US2012/31665, 9 pages Jul. 13, 2012.

Patent Cooperation Treaty, International Searching Authority, Search Report and Written Opinion for PCT/US2012/31679, 7 pages Jul. 13, 2012.

Ross, L., et al., "Potential Anticancer Agents. XVIII. Synthesis of Substituted 4,5-Trimethylenepyrimidines", J. Am. Chem. Soc., 1959, 81, 3108-3113.

Sarker et al., "Targeting the PI3K/AKT Pathway for the Treatment of Prostate Cancer", Clin Cancer Res vol. 15, 4799-4805 (2009).

Saura, C., et al., "A Phase Ib Study of the Akt Inhibitor GDC-0068 with Docetaxel or mFOLFOX6 in Patients with Advanced Solid Tumors", American Society of Clinical Oncology (ASCO), Annual Meeting, Chicago, IL, Jun. 1-5, 2012, Poster 3021, 1 page.

Saura, C., et al., "A Phase Ib Study of the Akt Inhibitor GDC-0068 with Docetaxel or mFOLFOX6 in Patients with Advanced Solid Tumors", J. Clin. Oncology (Meeting Abstracts), 30(suppl.), abstract: 3021, 3 pages, 2012.

Schayowitz et al., "Synergistic effect of a novel anti-androgen, VN/124-1, and signal transduction inhibitors in prostate cancer progression to hormone independence in vitro", Mol. Cancer Ther. vol. 7 (1), 121-132 (2008).

Office Action issued by the Japanese Patent Office for JP Patent Application No. 2009-518636 and translation thereof, Sep. 20, 2012 (mailing date), 8 pages.

Tabernero et al., "First-in-human phase I study evaluating the safety, pharmacokinetics (PK), and intratumor pharmacodynamics (PD) of the novel, oral, ATP-competitive Akt inhibitor GDC-0068", J. Clin. Oncol. (Meeting Abstracts), 29(15_suppl), abstract: 3022, 3 pages, 2011.

Tabernero et al., "First-in-human phase I study evaluating the safety, pharmacokinetics (PK), and intratumor pharmacodynamics (PD) of the novel, oral, ATP-competitive Akt inhibitor GDC-0068", American Society of Clinical Oncology (ASCO), Annual Meeting, Chicago, IL, Jun. 3-7, 2011, Poster 3022, 1 page.

Tabernero et al., "Targeting the PI3K-Akt-mTOR pathway with GDC-0068, a novel selective ATP competitive Akt inhibitor", 9th International Symposium on Targeted Anticancer Therapies, Paris, France, Mar. 7-9, 2011; presentation given Mar. 9, 2011, 13 pages.

Truong, T. N., "Office Action for U.S. Appl. No. 10/993,173", United States Patent and Trademark Office, May 26, 2009, 8 pages.

Truong, T. N., "Office Action for U.S. Appl. No. 10/993,173", United States Patent and Trademark Office, Aug. 6, 2008, 8 pages.

Vippagunta et al., "Crystalline (2001). Solids", *Advanced Drug Delivery Reviews 48*, 3-26 (2001).

Wellbrock et al., "BRAF as therapeutic target in melanoma", *Biochemical Pharmacology 80*, 561-567 (2010).

Yan et al., "A first-in-human trial of GDC-0068: A novel, oral, ATP-competitive Akt inhibitor, demonstrates robust suppression of the Akt pathway in surrogate and tumor tissues", AACR-NCI-EORTC International Conference: Molecular Targets and Cancer Therapeutics, San Francisco, CA, Nov. 12-16, Poster B154, 1 page, 2011.

Zhao, Z., et al., "Discovery of 2,3,5-trisubstituted pyridine derivatives as potent Akt1 and Akt2 dual inhibitors", Bioorg. Med. Chem. Lett., 2005, 15, 905-909.

Zhu et al., "Discovery and SAR of oxindole—pyridine-based protein kinase B/Akt inhibitors for treating cancers", *Bioorganic & Medicinal Chemistry Letters*, 16, 3424-3429 (2006).

Hirai et al., "Mk-2206, an allosteric Akt Inhibitor, enhances antitumor efficacy by standard chemotherapeutic agents or molecular targeted drugs in vitro and in vivo", *Molecular Cancer Therapeutics* vol. 9 (7), 1956-1967 (2010).

Bartlett, "Biomarkers and Patient Selection for PI3K/Akt/mTOR Targeted Therapies: Current Status and Future Directions", *Clinical Breast Cancer vol. 10 Suppl. 3*, S86-S95 (2010).

Belyanskaya et al., "Cisplatin activates Akt in small cell lung cancer cells and attenuates apoptosis by surviving upregulation", *Int. J. Cancer 117*, 755-763 (2005).

Brognard et al., "Akt/Protein Kinase B is Constitutively Active in Non-Small Cell Lung Cancer Cells and Promotes Cellular Survival and Resistance to Chemotherapy and Radiation", *Cancer Research 61*, 3986-3997 (2001).

Clark et al., "Constitutive and Inducible Akt Activity Chemotherapy, Trastuzumab, or Tamoxifen in Breast Cancer Cells", *Molecular Cancer Therapeutics* vol. 1, 707-717 (2002).

Emran et al., "Doxorubicin resistant neuroblastoma cells secrete factors that activate AKT and attenuate cytotoxicity in drug-sensitive cells", *Cancer Letters 182*, 53-59 (2002).

Fedier et al., "Potential of the Akt inhibitor LY294005 to antagonize the efficacy of Cisplatin against HCT116 tumor cells in a DNA mismatch repair-dependent manner", *International Journal of Oncology 29*, 1303-1310 (2006).

Lopiccolo et al., "Targeting the PI3K/Akt/mTOR pathway: Effective combinations and clinical considerations", *Drug Resistance Updates 11*, 32-50 (2008).

Shi et al., "Optimal Classes of Chemotherapeutic Agents Sensitized by Specific Small-Molecule Inhibitors of Akt In Vitro and In Vivo", *Neoplasia*, vol. 7 (11), 992-1000 (2005).

Tenzer et al., "The Phosphatidylinositide 3'-Kinase/Akt Survival Pathway is a Target for the Anticancer and Radiosensitizing Agent PKC412, an Inhibitor of Protein Kinase C1", *Cancer Research 61*, 8203-8210 (2001).

Tsurutani et al., "Inhibition of the Phosphatidylinositol 3-Kinase/Akt/Mammalian Target of Rapamycin Pathway but not the MEK/ERK Pathway Attenuates Laminin-Mediated Small Cell Lung Cancer Cellular Survival and Resistance to Imatinib Mesylate or Chemotherapy", *Cancer Res 65* (18), 8423-8432 (2005).

West et al., "Activation of the PI3K/Akt pathway and chemotherapeutic resistance", *Drug Resistance Updates 5*, 234-248 (2002).

Yang et al., "Akt/Protein Kinase B Signaling Inhibitor-2, a Selective Small Molecule Inhibitor of Akt Signaling with Antitumor Activity in Cancer Cells Overexpressing Akt", *Cancer Research 64*, 4394-4399 (2004).

* cited by examiner

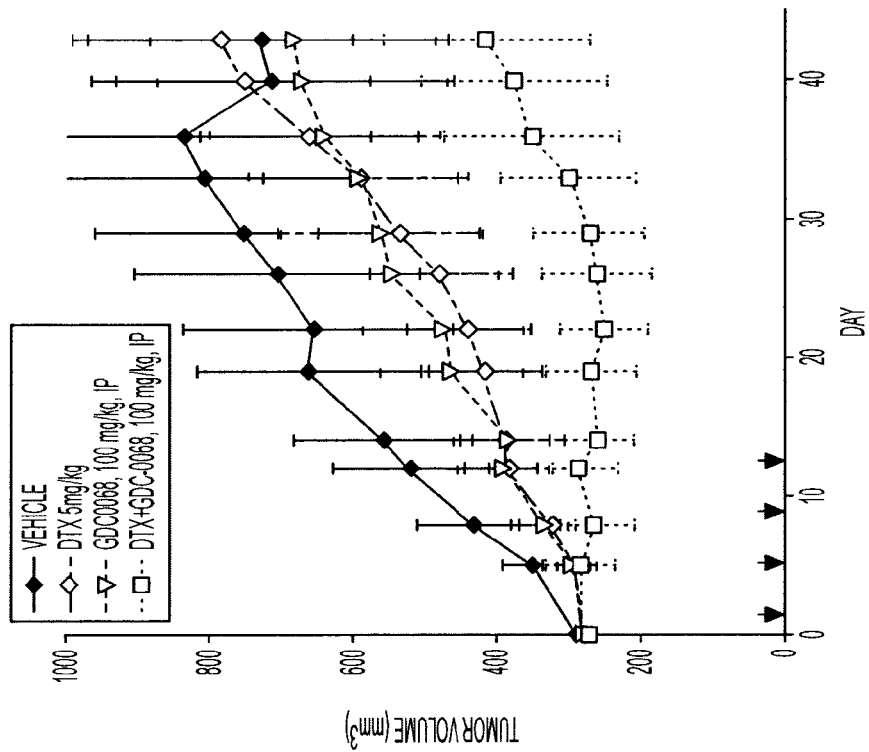
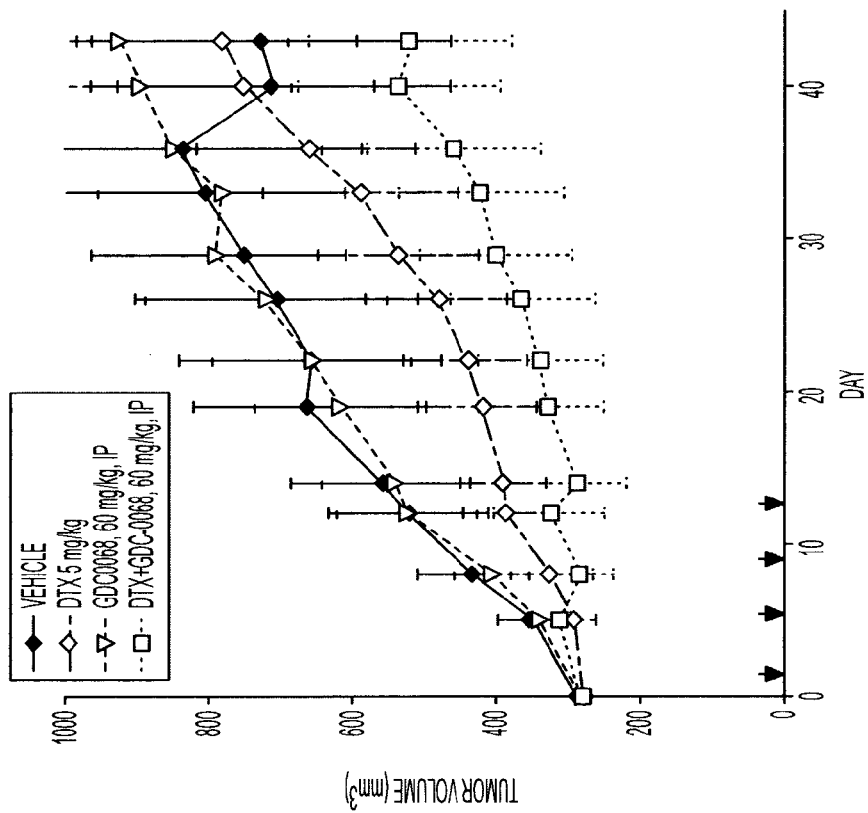

| TEST AGENT | ROUTE | SCHEDULE | DOSE (mg/kg) | DAY 0 (n) | LAST DAY | LAST DAY (n) | LAST DAY (VOLUME) | %TGI (LOWER, UPPER) | TTP 2X | TTP 5X | PR | CR | STI |
|---|---|---|---|---|---|---|---|---|---|---|---|---|---|
| VEHICLE (MCT) | PO | QD | 0+0 | 10 | 21 | 10 | 1715 | 0 (0, 0) | 4 | 11.5 | 0 | 0 | 10 |
| GDC-0068 | PO | QD | 50+0 | 5 | 21 | 5 | 1457 | 22 (-12, 45) | 4.5 | 17 | 0 | 0 | 5 |
| GDC-0068 | PO | QD | 75+0 | 5 | 21 | 2 | 1047 | 36 (6, 56) | 4.5 | NA | 0 | 0 | 5 |
| GDC-0068 | PO | QD | 100+0 | 5 | 21 | 4 | 1053 | 41 (14, 60) | 5.5 | NA | 0 | 0 | 5 |
| GDC-0973 | PO | QD | 0+2.5 | 5 | 21 | 5 | 747 | 60 (41, 73) | 5.5 | NA | 0 | 0 | 5 |
| GDC-0973 | PO | QD | 0+5 | 5 | 21 | 5 | 949 | 40 (15, 58) | 4.5 | NA | 0 | 0 | 5 |
| GDC-0973 | PO | QD | 0+7.5 | 5 | 21 | 5 | 862 | 45 (20, 62) | 4.5 | NA | 0 | 0 | 5 |
| GDC-0068+GDC-0973 | PO | QD | 50+2.5 | 5 | 21 | 4 | 786 | 55 (32, 69) | 6.5 | NA | 0 | 0 | 5 |
| GDC-0068+GDC-0973 | PO | QD | 75+2.5 | 5 | 21 | 4 | 792 | 43 (15, 61) | 5.5 | NA | 0 | 0 | 5 |
| GDC-0068+GDC-0973 | PO | QD | 100+2.5 | 5 | 21 | 3 | 750 | 59 (37, 74) | 6.5 | NA | 0 | 0 | 5 |
| GDC-0068+GDC-0973 | PO | QD | 50+5 | 5 | 21 | 4 | 879 | 43 (17, 62) | 4.5 | NA | 0 | 0 | 5 |
| GDC-0068+GDC-0973 | PO | QD | 75+5 | 5 | 21 | 4 | 641 | 68 (52, 80) | 7.5 | NA | 0 | 0 | 5 |
| GDC-0068+GDC-0973 | PO | QD | 100+5 | 5 | 21 | 1 | 635 | 78 (61, 90) | 9.5 | NA | 0 | 0 | 5 |
| GDC-0068+GDC-0973 | PO | QD | 50+7.5 | 5 | 21 | 4 | 577 | 74 (60, 83) | 8 | NA | 0 | 0 | 5 |
| GDC-0068+GDC-0973 | PO | QD | 75+7.5 | 5 | 21 | 2 | 405 | 85 (74, 93) | NA | NA | 0 | 0 | 5 |
| GDC-0068+GDC-0973 | PO | QD | 100+7.5 | 5 | 21 | 2 | 635 | 68 (46, 82) | 8 | NA | 0 | 0 | 5 |

FIG. 10C

| TEST AGENT | ROUTE | SCHEDULE | DOSE (mg/kg) | DAY 0 (n) | LAST DAY | LAST DAY (n) | LAST DAY (VOLUME) | %TGI (LOWER, UPPER) | TTP 2X | TTP 5X | PR | CR | STI |
|---|---|---|---|---|---|---|---|---|---|---|---|---|---|
| VEHICLE (MCT) | PO | QD | 0 + 0 | 10 | 21 | 10 | 1715 | 0 (0, 0) | 4 | 11.5 | 0 | 0 | 10 |
| GDC-0068 | PO | QD | 50 + 0 | 5 | 21 | 5 | 1457 | 22 (-12, 45) | 4.5 | 17 | 0 | 0 | 5 |
| GDC-0068 | PO | QD | 75 + 0 | 5 | 21 | 2 | 1047 | 36 (6, 56) | 4.5 | NA | 0 | 0 | 5 |
| GDC-0068 | PO | QD | 100 + 0 | 5 | 21 | 4 | 1053 | 41 (14, 60) | 5.5 | NA | 0 | 0 | 5 |
| GDC-0973 | PO | QD | 0 + 2.5 | 5 | 21 | 5 | 747 | 60 (41, 73) | 5.5 | NA | 0 | 0 | 5 |
| GDC-0973 | PO | QD | 0 + 5 | 5 | 21 | 5 | 949 | 40 (15, 58) | 4.5 | NA | 0 | 0 | 5 |
| GDC-0973 | PO | QD | 0 + 7.5 | 5 | 21 | 5 | 862 | 45 (20, 62) | 4.5 | NA | 0 | 0 | 5 |
| GDC-0068+GDC-0973 | PO | QD | 50 + 2.5 | 5 | 21 | 4 | 786 | 55 (32, 69) | 6.5 | NA | 0 | 0 | 5 |
| GDC-0068+GDC-0973 | PO | QD | 75 + 2.5 | 5 | 21 | 4 | 792 | 43 (15, 61) | 5.5 | NA | 0 | 0 | 5 |
| GDC-0068+GDC-0973 | PO | QD | 100 + 2.5 | 5 | 21 | 3 | 750 | 59 (37, 74) | 6.5 | NA | 0 | 0 | 5 |
| GDC-0068+GDC-0973 | PO | QD | 50 + 5 | 5 | 21 | 4 | 879 | 43 (17, 62) | 4.5 | NA | 0 | 0 | 5 |
| GDC-0068+GDC-0973 | PO | QD | 75 + 5 | 5 | 21 | 4 | 641 | 68 (52, 80) | 7.5 | NA | 0 | 0 | 5 |
| GDC-0068+GDC-0973 | PO | QD | 100 + 5 | 5 | 21 | 1 | 635 | 78 (61, 90) | 9.5 | NA | 0 | 0 | 5 |
| GDC-0068+GDC-0973 | PO | QD | 50 + 7.5 | 5 | 21 | 4 | 577 | 74 (60, 83) | 8 | NA | 0 | 0 | 5 |
| GDC-0068+GDC-0973 | PO | QD | 75 + 7.5 | 5 | 21 | 2 | 405 | 85 (74, 93) | NA | NA | 0 | 0 | 5 |
| GDC-0068+GDC-0973 | PO | QD | 100 + 7.5 | 5 | 21 | 2 | 635 | 68 (46, 82) | 8 | NA | 0 | 0 | 5 |

FIG. 11C

| TEST AGENT | ROUTE | SCHEDULE | DOSE (mg/kg) | DAY 0 (n) | LAST DAY | LAST DAY (n) | LAST DAY (VOLUME) | %TGI (LOWER, UPPER) | TTP 2X | TTP 5X | PR | CR | STI |
|---|---|---|---|---|---|---|---|---|---|---|---|---|---|
| VEHICLE (MCT) | PO | QD | 0 + 0 | 10 | 21 | 10 | 1715 | 0 (0, 0) | 4 | 11.5 | 0 | 0 | 10 |
| GDC-0068 | PO | QD | 50 + 0 | 5 | 21 | 5 | 1457 | 22 (-12, 45) | 4.5 | 17 | 0 | 0 | 5 |
| GDC-0068 | PO | QD | 75 + 0 | 5 | 21 | 2 | 1047 | 36 (6, 56) | 4.5 | NA | 0 | 0 | 5 |
| GDC-0068 | PO | QD | 100 + 0 | 5 | 21 | 4 | 1053 | 41 (14, 60) | 5.5 | NA | 0 | 0 | 5 |
| GDC-0973 | PO | QD | 0 + 2.5 | 5 | 21 | 5 | 747 | 60 (41, 73) | 5.5 | NA | 0 | 0 | 5 |
| GDC-0973 | PO | QD | 0 + 5 | 5 | 21 | 5 | 949 | 40 (15, 58) | 4.5 | NA | 0 | 0 | 5 |
| GDC-0973 | PO | QD | 0 + 7.5 | 5 | 21 | 5 | 862 | 45 (20, 62) | 4.5 | NA | 0 | 0 | 5 |
| GDC-0068+GDC-0973 | PO | QD | 50 + 2.5 | 5 | 21 | 4 | 786 | 55 (32, 69) | 6.5 | NA | 0 | 0 | 5 |
| GDC-0068+GDC-0973 | PO | QD | 75 + 2.5 | 5 | 21 | 4 | 792 | 43 (15, 61) | 5.5 | NA | 0 | 0 | 5 |
| GDC-0068+GDC-0973 | PO | QD | 100 + 2.5 | 5 | 21 | 3 | 750 | 59 (37, 74) | 6.5 | NA | 0 | 0 | 5 |
| GDC-0068+GDC-0973 | PO | QD | 50 + 5 | 5 | 21 | 4 | 879 | 43 (17, 62) | 4.5 | NA | 0 | 0 | 5 |
| GDC-0068+GDC-0973 | PO | QD | 75 + 5 | 5 | 21 | 4 | 641 | 68 (52, 80) | 7.5 | NA | 0 | 0 | 5 |
| GDC-0068+GDC-0973 | PO | QD | 100 + 5 | 5 | 21 | 1 | 635 | 78 (61, 90) | 9.5 | NA | 0 | 0 | 5 |
| GDC-0068+GDC-0973 | PO | QD | 50 + 7.5 | 5 | 21 | 4 | 577 | 74 (60, 83) | 8 | NA | 0 | 0 | 5 |
| GDC-0068+GDC-0973 | PO | QD | 75 + 7.5 | 5 | 21 | 2 | 405 | 85 (74, 93) | NA | NA | 0 | 0 | 5 |
| GDC-0068+GDC-0973 | PO | QD | 100 + 7.5 | 5 | 21 | 2 | 635 | 68 (46, 82) | 8 | NA | 0 | 0 | 5 |

FIG. 12C

| TEST AGENT | ROUTE | SCHEDULE | DOSE (mg/kg) | DAY 0 (n) | LAST DAY | LAST DAY (n) | DAY 18 (VOLUME) | %TGI (LOWER, UPPER) | TTP 2X | PR | CR |
|---|---|---|---|---|---|---|---|---|---|---|---|
| MCT + MDV3100 VEHICLE | PO/PO | QD + QD | 0 | 9 | 21 | 8 | 935 | 0 (0,0) | 11 | 0 | 0 |
| GDC-0068 | PO | QD | 50 | 9 | 21 | 9 | 553 | 54 (19, 82) | NA | 0 | 0 |
| MDV3100 | PO | QD | 5 | 9 | 21 | 9 | 596 | 43 (0, 72) | 17.5 | 0 | 0 |
| EXAMPLE 2 + MDV3100 | PO/PO | QD + QD | 50 + 5 | 9 | 21 | 8 | 309 | 95 (73, 115) | NA | 0 | 0 |

FIG. 13C

COMBO CI VALUE SUMMARY

| CELL LINE | TUMOR TYPE | GENE MUTATIONS | CHEMOTHERAPEUTIC | CHEMO EC50 | GDC-0068 EC50 | SYNERGY? | GDC-0068 CI EC50 |
|---|---|---|---|---|---|---|---|
| BT549 | BREAST | PTEN NEG, K-RAS | 5-FU | >40 | >2.5 | NO | 0.83 |
| CAL-51 | BREAST | PI3K E542K, PTEN NEG | 5-FU | >40 | 0.29 | YES | 0.6 |
| CAL-51X1.1 | BREAST | | 5-FU | 8 | 0.6 | YES | 0.65 |
| CAL120 | BREAST | | 5-FU | >40 | >2.5 | YES | 0.61 |
| HCC1954 | BREAST | PI3K H1047R | 5-FU | >40 | 0.9 | NO | 0.7 |
| MDA-MB-361 | BREAST | PI3K E545K | 5-FU | >40 | >2.5 | YES | 0.27 |
| MCF7 | BREAST | PI3K E545K | 5-FU | 7.8 | >2.5 | YES | 0.5 |
| MCF7(PRC) | BREAST | | 5-FU | 7.8 | >2.5 | YES | 0.34 |
| MDA-MB468 | BREAST | PI3K C769G T435I, PTEN NEG | 5-FU | 20 | >2.5 | NO | 1.24 |
| ZR-75-1 | BREAST | PTEN NEG | 5-FU | 20 | >2.5 | YES | 0.37 |
| U87(PRC) | GLIOMA | | 5-FU | 12 | >2.5 | YES | 0.3 |
| H2122 | LUNG | KRAS G12C | 5-FU | 0.35 | >2.5 | NO | 0.85 |
| KPP1 | MOUSE LINE | | 5-FU | 0.9 | >2.5 | YES? | 0.5??? |
| IGROV1 | OVARIAN | PI3K O1069W | 5-FU | 15.6 | 0.56 | YES | 0.56 |
| 22RV1 | PROSTATE | PI3K Q546R, B-RAF L597R | 5-FU | 0.625 | >2.5 | NO | 1.05 |
| PC3(GNE) | PROSTATE | PTEN NEG, PI3K N996H | 5-FU | >40 | 2.2 | NO | 0.84 |
| MCF7(PRC) | BREAST | | CARBOPLATIN | >12.5 | >2.5 | YES | 0.49 |
| MDA-MB-361 | BREAST | PI3K E545K | CARBOPLATIN | >12.5 | >2.5 | YES | 0.19 |
| U87(PRC) | GLIOMA | | CARBOPLATIN | >12.5 | >2.5 | NO | 0.72 |

FROM FIG. 16A

| | | | | | |
|---|---|---|---|---|---|
| A549(GNE) | LUNG | | CARBOPLATIN | >12.5 | >2.5 | YES | 0.51 |
| A549(PRC) | LUNG | PI3K M772X N996H, KRAS G12S | CARBOPLATIN | >12.5 | >2.5 | YES | 0.66 |
| H1299(PRC) | LUNG | | CARBOPLATIN | >12.5 | >2.5 | NO | 0.77 |
| H2122 | LUNG | KRAS G12C | CARBOPLATIN | >12.5 | >2.5 | NO | 0.87 |
| A375(PRC) | MELANOMA | (B-RAF V600E IN GNE LINE) | CARBOPLATIN | >12.5 | >2.5 | NO | 0.84 |
| IGROV1 | OVARIAN | PI3K O1069W | CARBOPLATIN | >12.5 | 0.56 | NO | 1.2 |
| SKOV3(PRC) | OVARIAN | | CARBOPLATIN | >12.5 | >2.5 | NO | 1.09 |
| PC3(GNE) | PROSTATE | PTEN NEG, PI3K N996H | CARBOPLATIN | >12.5 | >2.5 | YES | 0.09 |
| PC3(PRC) | PROSTATE | | CARBOPLATIN | >12.5 | >2.5 | NO | 0.95 |
| KM12 | COLON | PTEN NEG | CPT-11 | >2.5 | >2.5 | YES | 0.57 |
| WiDR | COLON | | CPT-11 | >2.5 | >2.5 | YES | 0.54 |
| BT549 | BREAST | PTEN NEG, K-RAS | DOCETAXEL | 0.002 | >2.5 | YES | 0.47 |
| CAL-51 | BREAST | PI3K E542K, PTEN NEG | DOCETAXEL | 0.003 | 0.29 | YES | 0.54 |
| CAL-51X1.1 | BREAST | | DOCETAXEL | 0.009 | 0.6 | YES | 0.58 |
| CAL120 | BREAST | | DOCETAXEL | 0.02 | >2.5 | YES | 0.4 |
| HCC1954 | BREAST | PI3K H1047R | DOCETAXEL | 0.004 | 0.9 | YES | 0.48 |
| MCF7 | BREAST | PI3K E545K | DOCETAXEL | 0.005 | >2.5 | YES | 0.43 |
| MCF7(PRC) | BREAST | | DOCETAXEL | 0.005 | >2.5 | YES | 0.47 |
| MDA-MB-361 | BREAST | PI3K E545K | DOCETAXEL | 0.003 | >2.5 | YES | 0.24 |
| MDA-MB468 | BREAST | PI3K C769G T435I, PTEN NEG | DOCETAXEL | 0.005 | >2.5 | NO | 0.78 |

FROM FIG. 16B

| | | | | | | |
|---|---|---|---|---|---|---|
| ZR-75-1 | BREAST | PTEN NEG | DOCETAXEL | 0.0025 | >2.5 | YES | 0.52 |
| U87(ARRAY) | GLIOMA | | DOCETAXEL | 0.0625 | >2.5 | YES | 0.17 |
| U87(ARRAY) | GLIOMA | | DOCETAXEL | 0.009 | >2.5 | YES | 0.2 |
| U87(GNE) | GLIOMA | PI3K I397M, PTEN NEG | DOCETAXEL | 0.00625 | >2.5 | YES | 0.47 |
| U87(GNE) | GLIOMA | PI3K I397M, PTEN NEG | DOCETAXEL | 0.009 | >2.5 | YES | 0.35 |
| U87(PRC) | GLIOMA | | DOCETAXEL | 0.009 | >2.5 | YES | 0.32 |
| U87(PRC) | GLIOMA | | DOCETAXEL | 0.00625 | >2.5 | YES | 0.42 |
| U87(PRC) | GLIOMA | | DOCETAXEL | 0.009 | >2.5 | YES | 0.25 |
| A549(GNE) | LUNG | PI3K M772X N996H, KRAS G12S | DOCETAXEL | 0.0025 | >2.5 | YES | 0.59 |
| A549(PRC) | LUNG | | DOCETAXEL | 0.0025 | >2.5 | YES | 0.39 |
| H1299(PRC) | LUNG | | DOCETAXEL | 0.025 | >2.5 | NO | 0.72 |
| H2122 | LUNG | KRAS G12C | DOCETAXEL | 0.01 | >2.5 | NO/YES? | 0.71(0.54) |
| A375(PRC) | MELANOMA | | DOCETAXEL | 0.0025 | >2.5 | YES | 0.64 |
| IGROV1 | OVARIAN | PI3K O1069W | DOCETAXEL | 0.00392 | 0.56 | YES | 0.54 |
| SKOV3(PRC) | OVARIAN | | DOCETAXEL | 0.005 | >2.5 | NO | 0.79 |
| 22RV1 | PROSTATE | PI3K Q546R, B-RAF L597R | DOCETAXEL | 0.005 | >2.5 | YES | 0.64 |
| PC3(GNE) | PROSTATE | PTEN NEG, PI3K N996H | DOCETAXEL | 0.0052 | 1.09 | YES | 0.44(0.66) |
| PC3(PRC) | PROSTATE | | DOCETAXEL | 0.0025 | >2.5 | YES | 0.55 |
| MCF7(PRC) | BREAST | | DOXORUBICIN | 0.2 | >2.5 | YES | 0.35 |
| U87(PRC) | GLIOMA | | DOXORUBICIN | 0.15 | >2.5 | NO | 0.92 |

FROM FIG. 16C

| | | | | | | |
|---|---|---|---|---|---|---|
| A549(GNE) | LUNG | PI3K M772X N996H, KRAS G12S | DOXORUBICIN | 0.2 | >2.5 | YES | 0.48 |
| A549(PRC) | LUNG | | DOXORUBICIN | 0.2 | >2.5 | YES | 0.67 |
| H1299(PRC) | LUNG | | DOXORUBICIN | 0.2 | >2.5 | NO | 0.8 |
| H2122 | LUNG | KRAS G12C | DOXORUBICIN | 0.01 | >2.5 | NO | 0.9 |
| A375(PRC) | MELANOMA | | DOXORUBICIN | 0.03 | >2.5 | NO | 0.72 |
| EFO21 | OVARIAN | PTEN NEG, B-RAF I457N | DOXORUBICIN | 0.12 | 0.3 | NO | 0.91 |
| SKOV3 | OVARIAN | PI3K H1047R | DOXORUBICIN | 0.3 | >2.5 | YES | 0.67 |
| SKOV3(PRC) | OVARIAN | | DOXORUBICIN | 0.07 | >2.5 | NO | 0.87 |
| PC3(GNE) | PROSTATE | PTEN NEG, PI3K N996H | DOXORUBICIN | 0.4 | >2.5 | NO | 0.74 |
| PC3(PRC) | PROSTATE | | DOXORUBICIN | 0.4 | >2.5 | YES | 0.38 |
| BT549 | BREAST | PTEN NEG, K-RAS | GEMCITABINE | 0.012 | >2.5 | NO | 0.73 |
| CAL-51 | BREAST | PI3K E42K, PTEN NEG | GEMCITABINE | 0.0024 | 0.29 | NO | 0.87 |
| CAL-51X1.1 | BREAST | | GEMCITABINE | 0.00625 | 0.6 | YES | 0.47 |
| CAL120 | BREAST | | GEMCITABINE | 0.7 | >2.5 | YES | 0.12 |
| HCC1954 | BREAST | PI3K H1047R | GEMCITABINE | 0.005 | 0.9 | YES | 0.61 |
| MCF7 | BREAST | PI3K E545K | GEMCITABINE | 0.005 | >2.5 | YES | 0.42 |
| MCF7(PRC) | BREAST | | GEMCITABINE | 0.00625 | >2.5 | YES | 0.44 |
| MDA-MB-361 | BREAST | PI3K E545K | GEMCITABINE | 0.012 | >2.5 | YES | 0.19 |
| MDA-MB-468 | BREAST | PI3K C769G T435I, PTEN NEG | GEMCITABINE | 0.0025 | >2.5 | NO | 1.14 |

FROM FIG. 16D

| | | | | | |
|---|---|---|---|---|---|
| ZR-75-1 | BREAST | | GEMCITABINE | 0.01 | >2.5 | YES | 0.42 |
| U87(PRC) | GLIOMA | PTEN NEG | GEMCITABINE | 0.00625 | >2.5 | YES | 0.3 |
| A549(GNE) | LUNG | PI3K M772X N996H, KRAS G12S | GEMCITABINE | 0.01 | >2.5 | YES | 0.88 |
| A549(PRC) | LUNG | | GEMCITABINE | 0.01 | >2.5 | YES | 0.35 |
| H2122 | LUNG | KRAS G12C | GEMCITABINE | 0.0027 | >2.5 | NO | 0.7 |
| KPP1 | MOUSE LINE | | GEMCITABINE | 0.017 | >2.5 | NO | 1.04 |
| IGROV1 | OVARIAN | PI3K O1069W | GEMCITABINE | 0.0088 | 0.56 | NO | 0.92 |
| SKOV3 | OVARIAN | PI3K H1047R | GEMCITABINE | 0.05 | >2.5 | NO | 0.97 |
| 22RV1 | PROSTATE | PI3K Q546R, B-RAF L597R | GEMCITABINE | 0.005 | >2.5 | YES | 0.54 |
| PC3(GNE) | PROSTATE | PTEN NEG, PI3K N996H | GEMCITABINE | 0.125 | >2.5 | YES | 0.67 |
| PC3(PRC) | PROSTATE | | GEMCITABINE | 0.0125 | >2.5 | YES | 0.34 |
| COLO205 | COLON | B-RAF V600E | SN38 | 0.012 | >2.5 | YES | 0.55 |
| HCT116 | COLON | PI3K H1047R | SN38 | 0.024 | >2.5 | YES | 0.48 |
| HT29 | COLON | B-RAF V600E | SN38 | 0.04 | >2.5 | NO | 0.93 |
| G140 | GLIOMA | | TEMODAR | >10 | >2.5 | NO | 0.73 |
| G61 | GLIOMA | | TEMODAR | >10 | >2.5 | YES | 0.55 |
| U87(GNE) | GLIOMA | PI3K I397M, PTEN NEG | TEMODAR | >10 | >2.5 | YES | 0.31 |
| LOX | MELANOMA | B-RAF V600E | | | | NO | 0.93 |

FIG. 16E

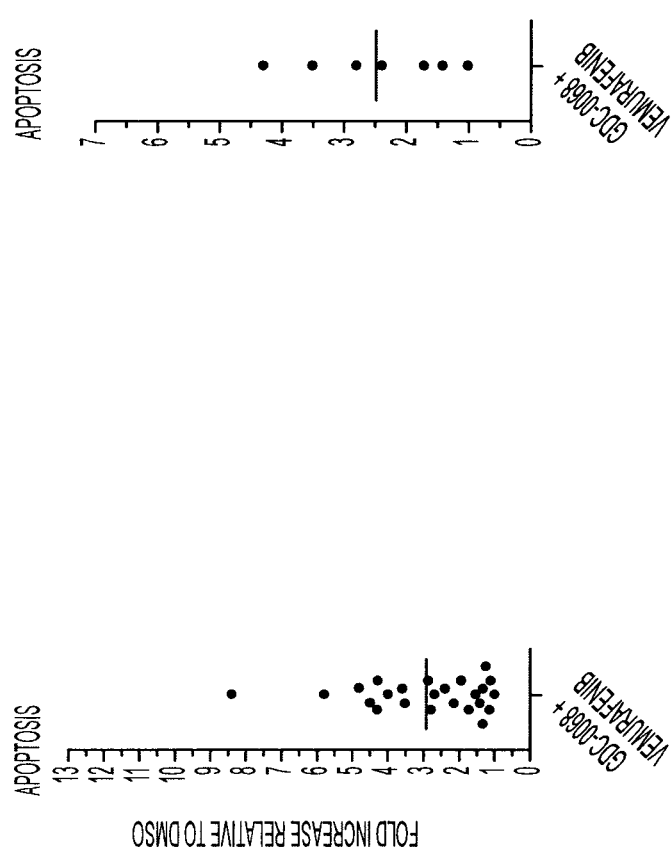

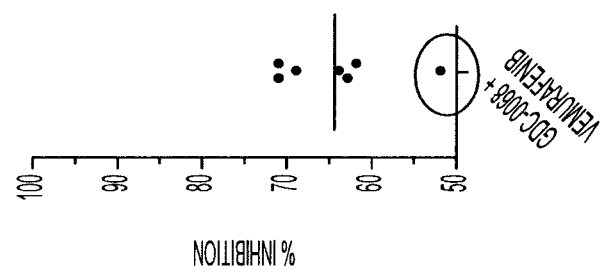

COMBINATIONS OF AKT INHIBITOR COMPOUNDS AND VEMURAFENIB, AND METHODS OF USE

PRIORITY OF INVENTION

This application claims priority to U.S. Provisional Application No. 61/470,803 that was filed on Apr. 1, 2011, and to U.S. Provisional Application No. 61/470,624 that was filed on Apr. 1, 2011. The entire content of these provisional applications are hereby incorporated herein by reference.

FIELD OF THE INVENTION

The invention relates generally to pharmaceutical combinations of compounds with activity against hyperproliferative disorders such as cancer and which include compounds that inhibit AKT kinase activity. The invention also relates to methods of using the combinations for in vitro, in situ, and in vivo diagnosis or treatment of mammalian cells, or associated pathological conditions.

BACKGROUND OF THE INVENTION

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

International Patent Application Publication Number WO 2008/006040 discusses a series of inhibitors of AKT of formula I:

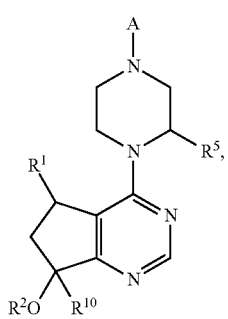

Currently, there remains a need for improved methods and compositions that can be used to treat hyperproliferative diseases such as cancer.

SUMMARY OF THE INVENTION

It has been determined that additive or synergistic effects in inhibiting the growth of cancer cells in vitro and in vivo can be achieved by administering a compound of formula I or a pharmaceutically acceptable salt thereof in combination with certain other specific chemotherapeutic agents. The combinations and methods may be useful in the treatment of hyperproliferative disorders such as cancer.

One aspect of the invention provides a method for treating a hyperproliferative disorder in a mammal comprising, administering to the mammal, a) a compound of formula I:

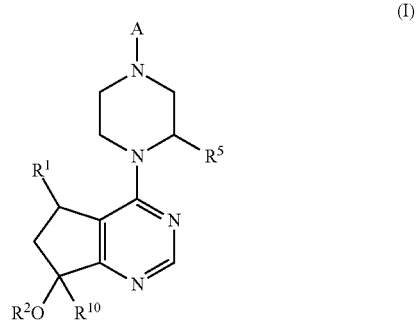

or a pharmaceutically acceptable salt thereof; and b) one or more agents selected from 5-FU, a platinum agent (carboplatin, cisplatnin, oxaliplatin, etc.) irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973.

The compound of formula I or the pharmaceutically acceptable salt thereof and the chemotherapeutic agent may be co-formulated for administration in a combination as a pharmaceutical composition or they may be administered separately in alternation (sequentially) as a therapeutic combination.

One aspect of the invention provides a method for treating a disease or condition modulated by AKT kinase in a mammal comprising, administering to the mammal, a) a compound of formula I or a pharmaceutically acceptable salt thereof; and b) one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973.

One aspect of the invention provides the combination of a) a compound of formula I or a pharmaceutically acceptable salt thereof; and b) one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 for treating a hyperproliferative disorder.

One aspect of the invention provides the combination of a) a compound of formula I or a pharmaceutically acceptable salt thereof; and b) one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 for treating a disease or condition modulated by AKT kinase.

One aspect of the invention provides the use of a compound of formula I or a pharmaceutically acceptable salt thereof in the preparation of a medicament for the treatment of a hyperproliferative disorder in a mammal, wherein one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 are administered to the mammal.

One aspect of the invention provides the use of a compound of formula I or a pharmaceutically acceptable salt thereof in the preparation of a medicament for the treatment of a disease or condition modulated by AKT kinase in a mammal, wherein one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 are administered to the mammal.

One aspect of the invention provides a kit comprising a compound of formula I or a pharmaceutically acceptable salt thereof, a container, and a package insert or label indicating the administration of the compound of formula I or a pharmaceutically acceptable salt thereof with one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 for treating a hyperproliferative disorder.

One aspect of the invention provides a product comprising a compound having formula I or a pharmaceutically acceptable salt thereof, and a chemotherapeutic agent selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973; as a combined preparation for separate, simultaneous or sequential use in the treatment of a hyperproliferative disorder.

One aspect of the invention provides a method for treating a hyperproliferative disorder in a mammal comprising, administering to the mammal, a) a compound of formula I or a pharmaceutically acceptable salt thereof; and b) vemurafenib or a pharmaceutically acceptable salt thereof.

One aspect of the invention provides a method for treating a hyperproliferative disorder in a mammal comprising, administering to the mammal, a) GDC-0068 or a pharmaceutically acceptable salt thereof; and b) vemurafenib or a pharmaceutically acceptable salt thereof.

One aspect of the invention provides a method for treating lymphoma, colon cancer, metastatic melanoma, thyroid cancer or lung cancer in a mammal comprising, administering to the mammal a) GDC-0068 or a pharmaceutically acceptable salt thereof; and b) vemurafenib or a pharmaceutically acceptable salt thereof.

One aspect of the invention provides a method for treating a disease modulated by BRAF V600E mutation in a mammal comprising, administering to the mammal a) GDC-0068 or a pharmaceutically acceptable salt thereof; and b) vemurafenib or a pharmaceutically acceptable salt thereof.

One aspect of the invention provides a method for treating a vemurafenib single agent-resistant disease in a mammal comprising, administering to the mammal, a) GDC-0068 or a pharmaceutically acceptable salt thereof; and b) vemurafenib or a pharmaceutically acceptable salt thereof.

One aspect of the invention provides a method for treating vemurafenib single agent-resistant metastatic melanoma in a mammal comprising, administering to the mammal, a) GDC-0068 or a pharmaceutically acceptable salt thereof; and b) vemurafenib or a pharmaceutically acceptable salt thereof.

In addition to providing improved treatment for a given hyperproliferative disorder, administration of certain combinations of the invention may improve the quality of life for a patient compared to the quality of life experienced by the same patient receiving a different treatment. For example, administration of a combination of a compound of formula I or a pharmaceutically acceptable salt thereof, and a chemotherapeutic agent as described herein to a patient may provide an improved quality of life compared to the quality of life the same patient would experience if they received only the chemotherapeutic agent as therapy. For example, the combined therapy with the combination described herein may lower the dose of chemo agents needed, thereby lessening the side-effects associated with high-dose chemotherapeutic agents (e.g., nausea, vomiting, hair loss, rash, decreased appetite, weight loss, etc.). The combination may also cause reduced tumor burden and the associated adverse events, such as pain, organ dysfunction, weight loss, etc. In another example, the combination may also be effective to treat the disease after it has become resistant to one of the agents alone (for example, vemurafenib resistant cancers, such as metastatic melanoma, may be treated by combinations of vemurafenib and a compound of formula I or a salt thereof).

Accordingly, one aspect of the invention provides a compound of formula I or a pharmaceutically acceptable salt thereof, for therapeutic use for improving the quality of life of a patient treated for a hyperproliferative disorder with an agent selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973.

BRIEF DESCRIPTION OF THE DRAWINGS

FIG. 4 illustrates results from Example 15 for the compound of Example 2 dosed IP intermittently and docetaxel in MCF7-neo/HER2 tumors.

FIG. 16 illustrates data from Example 14 that shows that representative combinations provide additive or synergistic activity against a number of cancer types.

FIG. 25 illustrates the fold increase in cell death relative to DMSO with combinations of GDC-0068 plus vemurafenib in A375 melanoma cell line (FIG. 25A) and vemurafenib resistant cell line (FIG. 25B). This figure demonstrates how the combination of GDC-0068 and vemurafenib acts synergistically to treat patients who become resistant to vemurafenib single agent therapy.

FIG. 26 illustrates the increased sensitivity of vemurafenib-resistant A375 melanoma cell line clones over a parental cell line (red circle) as measured by percent inhibition to the combination of GDC-0068 plus vemurafenib. This figure demonstrates how the combination of GDC-0068 and vemurafenib acts synergistically to treat patients who become resistant to vemurafenib single agent therapy.

DETAILED DESCRIPTION OF EXEMPLARY EMBODIMENTS AND DEFINITIONS

Figure 1:
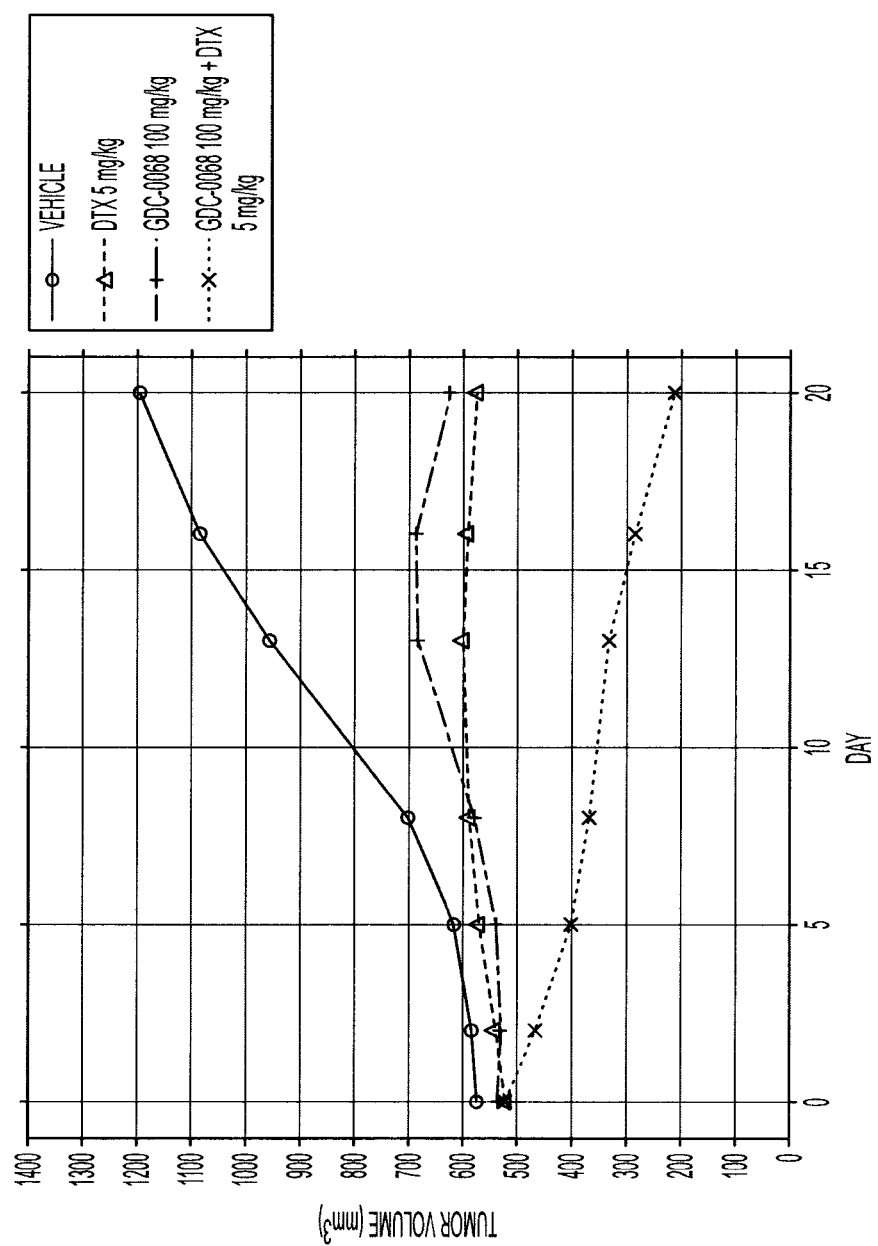
FIG. 1 illustrates results from Example 15 for the compound of Example 2 and docetaxel in LuCap35V primary prostate tumors.

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The terms "heterocycle," "hetercyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), nitrogen (nitrogen-linked) or oxygen (oxygen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that, alone in one example, or in combination with a second chemotherapeutic agent in another example, (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug, alone or in combination, may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug, alone or in combination, may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver. Additionally, examples of cancers driven by the BRAF V600E mutation include non-hodgkins lymphoma, colorectal cancer, metastatic melanoma, papillary thyroid carcinoma, non-small cell lung carcinoma, and adenocarcinoma of the lung. One particular example of cancers driven by the BRAF V600E mutation is metastatic or unresectable melanoma.

A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted conventional chemotherapy.

The term "mammal" includes, but is not limited to, humans, mice, rats, guinea pigs, monkeys, dogs, cats, horses, cows, pigs, sheep, and poultry. The term patient refers to a mammal, and in one embodiment, the patient is a human.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

If the compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to a physical association or complex of one or more solvent molecules and a compound of the invention. The compounds may exist in unsolvated as well as solvated forms. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. This physical association involves varying degrees of ionic and covalent bonding, including hydrogen bonding. In certain instances the solvate will be capable of isolation, for example when one or more solvent molecules are incorporated in the crystal lattice of the crystalline solid. Preparation of solvates is generally known, for example, M. Caira et al, J. Pharmaceutical Sci., 93(3), 601 611 (2004). Similar preparations of solvates, hemisolvate, hydrates and the like are described by E. C. van Tonder et al, AAPS PharmSciTech., 5(1), article 12 (2004); and A. L. Bingham et al, Chem. Commun., 603 604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "synergistic" as used herein refers to a therapeutic combination which is more effective than the additive effects of the two or more single agents. A determination of a synergistic interaction between a compound of formula I or a pharmaceutically acceptable salt thereof and one or more chemotherapeutic agent may be based on the results obtained from the assays described herein. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided by this invention have been evaluated in several assay systems, and the data can be analyzed utilizing a standard program for quantifying synergism, additivism, and antagonism among anticancer agents. The program utilized, for example in FIG. 16, is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained, in one example, when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes or by different oral doses. In general, during alternation therapy, an effective dosage of each active ingredient is administered sequentially, i.e., serially, whereas in combination therapy, effective dosages of two or more active ingredients are administered together.

In some examples (see FIGS. 18-20), combination effects were evaluated using both the BLISS independence model and the highest single agent (HSA) model (Lehár et al. 2007, Molecular Systems Biology 3:80). BLISS scores quantify degree of potentiation from single agents and a BLISS score >0 suggests greater than simple additivity. An HSA score >0 suggests a combination effect greater than the maximum of the single agent responses at corresponding concentrations.

In one aspect the invention provides a method for treating a hyperproliferative disorder wherein administration of the compound of formula I or the salt thereof and the one or more agents selected from 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973 provides a synergistic effect in treating the hyperproliferative disorder. In a further aspect, the synergistic effect has a Combination Index value of less than about 0.8. In a further aspect, the synergistic effect has a BLISS score greater than 0. In a further aspect, the synergistic effect has an HAS score greater than 0. In a further aspect, the hyperproliferative disorder comprises PTEN null status, PTEN low status, a PI3k mutation, an AKT mutation or high pAKT expression or activity.

Another aspect provides a method for treating a cancer selected from lymphoma, colon cancer, metastatic melanoma, thyroid cancer or lung cancer wherein administration of GDC-0068 or a salt thereof and vemurafenib or a salt thereof provides a synergistic effect in treating the cancer. In a further aspect, the cancer comprises a BRAF V600E mutation, and in one example further comprises high pAKT expression or activity levels. In a further aspect, the synergistic effect has a Combination Index value of less than about 0.8. In a further aspect, the synergistic effect has a BLISS score greater than 0. In a further aspect, the synergistic effect has an HAS score greater than 0.

Formula I Compounds

Formula I compounds include a compound of formula I:

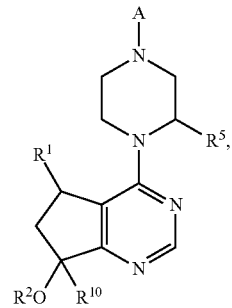

and pharmaceutically acceptable salts thereof, wherein:
$R^1$ is H, Me, Et, vinyl, $CF_3$, $CHF_2$ or $CH_2F$;
$R^2$ is H or Me;
$R^5$ is H, Me, Et, or $CF_3$;
A is

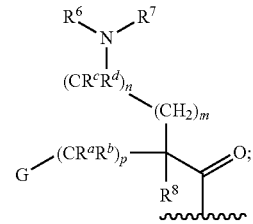

G is phenyl optionally substituted by one to four $R^9$ groups or a 5-6 membered heteroaryl optionally substituted by a halogen;

$R^6$ and $R^7$ are independently H, $OCH_3$, ($C_3$-$C_6$ cycloalkyl)-($CH_2$), ($C_3$-$C_6$ cycloalkyl)-($CH_2CH_2$), V—$(CH_2)_{0-1}$ wherein V is a 5-6 membered heteroaryl having from one to two ring heteroatoms independently selected from N, O and S, W—$(CH_2)_{1-2}$ wherein W is phenyl optionally substituted with F, Cl, Br, I, OMe, $CF_3$ or Me, $C_3$-$C_6$-cycloalkyl optionally substituted with $C_1$-$C_3$ alkyl or O($C_1$-$C_3$ alkyl), hydroxy-($C_3$-$C_6$-cycloalkyl), fluoro-($C_3$-$C_6$-cycloalkyl), $CH(CH_3)CH(OH)$phenyl, 4-6 membered heterocycle optionally substituted with F, OH, $C_1$-$C_3$-alkyl, cyclopropylmethyl or C(=O)($C_1$-$C_3$ alkyl), or $C_1$-$C_6$-alkyl optionally substituted with one or more groups independently selected from OH, oxo, O($C_1$-$C_6$-alkyl), CN, F, $NH_2$, NH($C_1$-$C_6$-alkyl), N($C_1$-$C_6$-alkyl)$_2$, cyclopropyl, phenyl, imidazolyl, piperidinyl, pyrrolidinyl, morpholinyl, tetrahydrofuranyl, oxetanyl, or tetrahydropyranyl, or R$^6$ and R$^7$ together with the nitrogen to which they are attached form a 4-7 membered heterocyclic ring, wherein said heterocyclic ring is optionally substituted with one or more groups independently selected from OH, halogen, oxo, CF$_3$, CH$_2$CF$_3$, CH$_2$CH$_2$OH, O(C$_1$-C$_3$ alkyl), C(=O)CH$_3$, NH$_2$, NHMe, N(Me)$_2$, S(O)$_2$CH$_3$, cyclopropylmethyl and C$_1$-C$_3$ alkyl;

R$^a$ and R$^b$ are H, or R$^a$ is H, and R$^b$ and R$^6$ together with the atoms to which they are attached form a 5-6 membered heterocyclic ring having one or two ring nitrogen atoms;

R$^c$ and R$^d$ are H or Me, or R$^c$ and R$^d$ together with the atom to which they are attached from a cyclopropyl ring;

R$^8$ is H, Me, F or OH, or R$^8$ and R$^6$ together with the atoms to which they are attached form a 5-6 membered heterocyclic ring having one or two ring nitrogen atoms;

each R$^9$ is independently halogen, C$_1$-C$_6$-alkyl, C$_3$-C$_6$-cycloalkyl, O—(C$_1$-C$_6$-alkyl), CF$_3$, OCF$_3$, S(C$_1$-C$_6$-alkyl), CN, OCH$_2$-phenyl, CH$_2$O-phenyl, NH$_2$, NH—(C$_1$-C$_6$-alkyl), N—(C$_1$-C$_6$-alkyl)$_2$, piperidine, pyrrolidine, CH$_2$F, CHF$_2$, OCH$_2$F, OCHF$_2$, OH, SO$_2$(C$_1$-C$_6$-alkyl), C(O)NH$_2$, C(O)NH(C$_1$-C$_6$-alkyl), and C(O)N(C$_1$-C$_6$-alkyl)$_2$;

R$^{10}$ is H or Me; and m, n and p are independently 0 or 1.

A specific compound of Formula I is a compound wherein A is

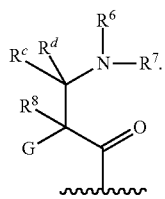

A specific compound of Formula I is a compound Formula Ia:

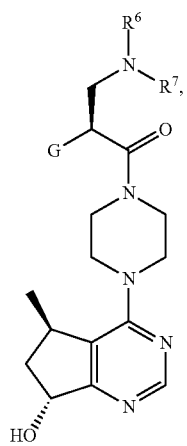

or a pharmaceutically acceptable salt thereof.

In one aspect of the invention the compound of formula I excludes the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one Formula Ia:

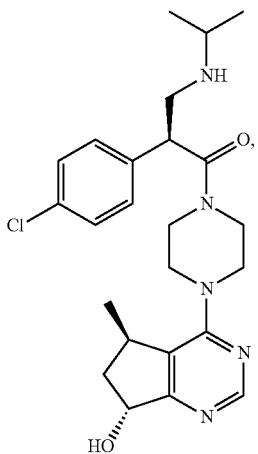

and pharmaceutically acceptable salts thereof (this compound may also be referred to as GDC-0068).

Preparation of Formula I Compounds

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or salts thereof.

For illustrative purposes, Schemes 1-4 and Schemes A-J shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

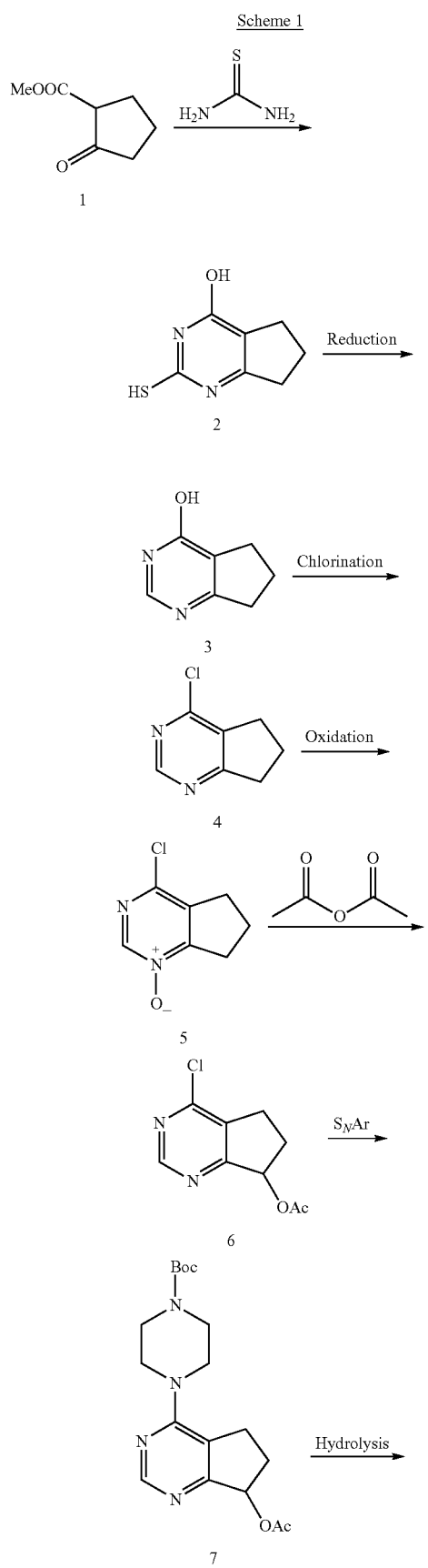

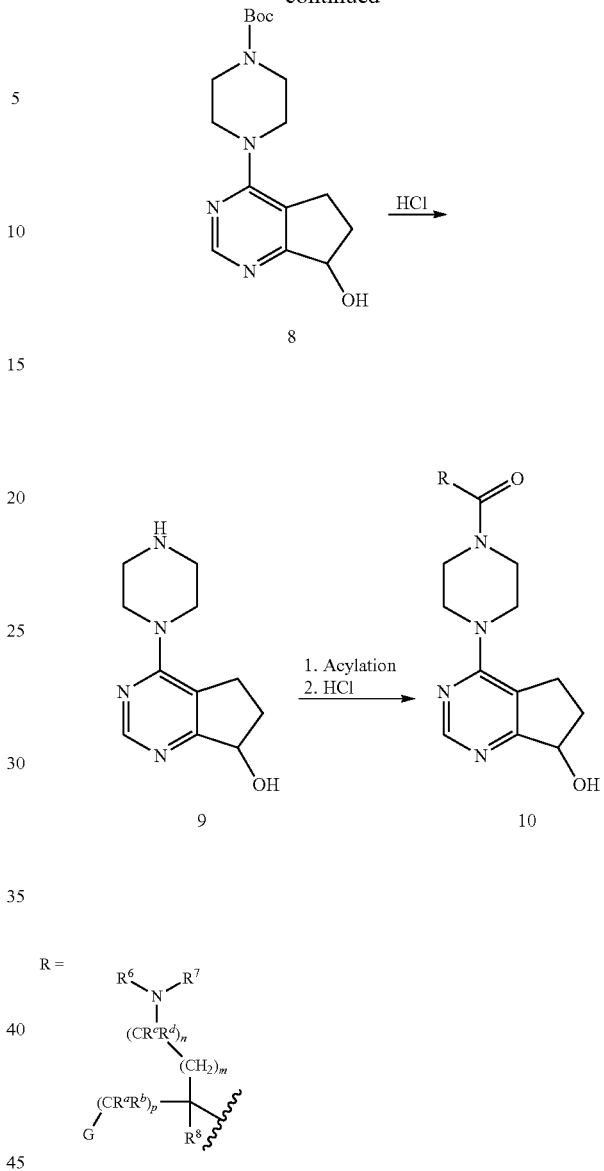

Scheme 1 shows a method of preparing compound 10 of Formula I wherein $R^1$ is H, $R^2$ is H and $R^5$ is H. Formation of pyrimidine 2 can be accomplished by the reaction of the keto ester 1 with thiourea in the presence of a base such as KOH in an appropriate solvent, such as ethanol. After reduction of the mercapto group of compound 2 under standard reducing conditions (e.g., Raney Ni and $NH_4OH$) to provide compound 3, the hydroxypyrimidine 3 can be chlorinated under standard conditions (e.g., $POCl_3$ in DIEA/DCE) to provide compound 4. Compound 4 is then oxidized under standard conditions (e.g., MCPBA in an appropriate solvent such as $CHCl_3$) to give the pyrimidine-oxide 5. Treatment of the pyrimidine-oxide with acetic anhydride gives the rearrangement product 6. Compound 7 is obtained by reacting compound 6 with an appropriately substituted piperidine under standard $S_NAr$ reaction conditions to provide compound 7. Compound 7 is hydrolyzed to provide compound 8, which is then deprotected to yield the intermediate 9. Acylation of the piperazinyl cyclopenta[d]pyrimidine 9 with an appropriated amino acid in the presence of a coupling reagent such as HBTU, followed by deprotection if necessary, gives compound 10 of Formula I.

Scheme 2
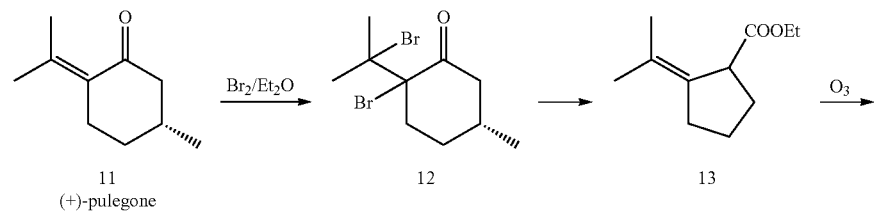
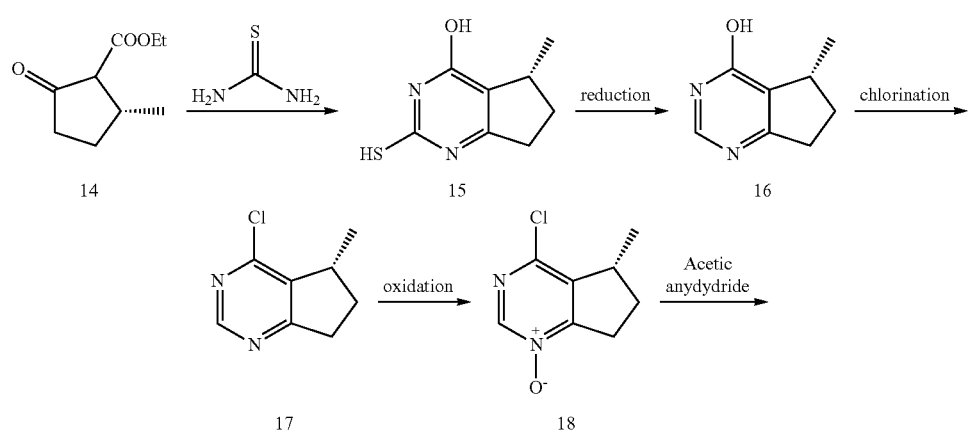
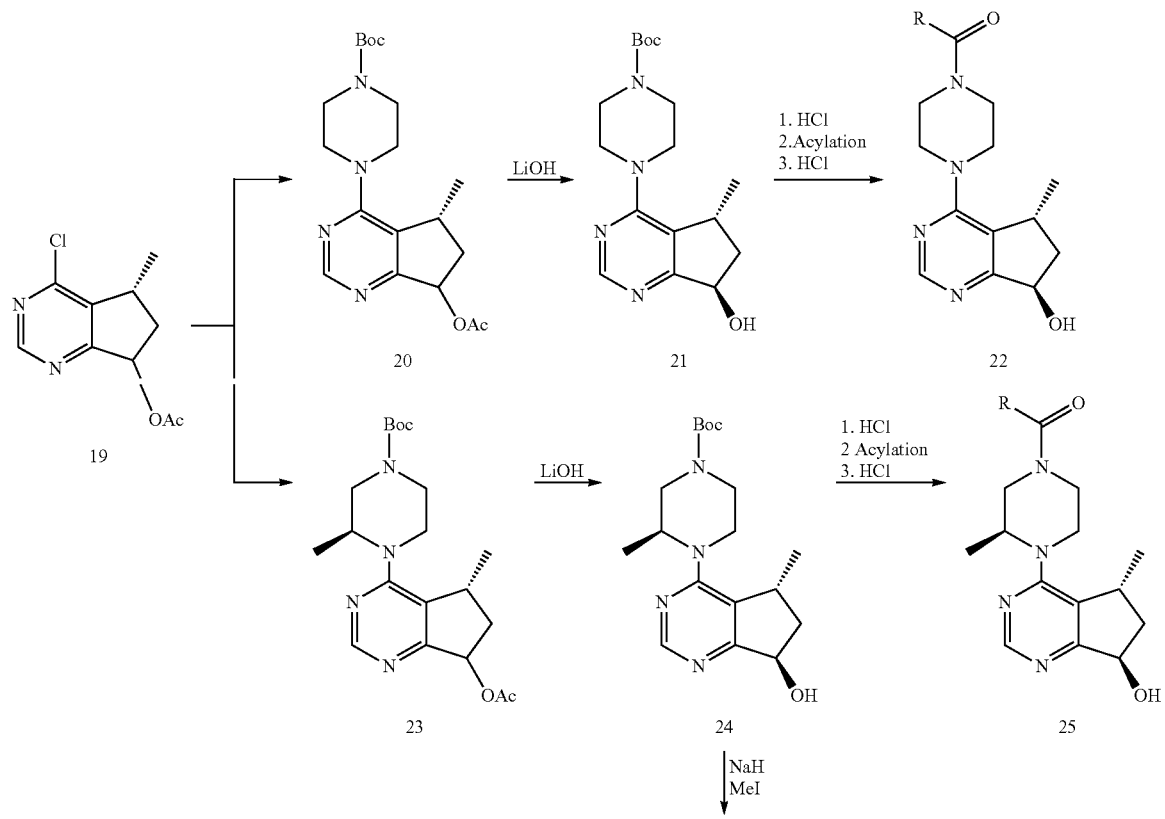

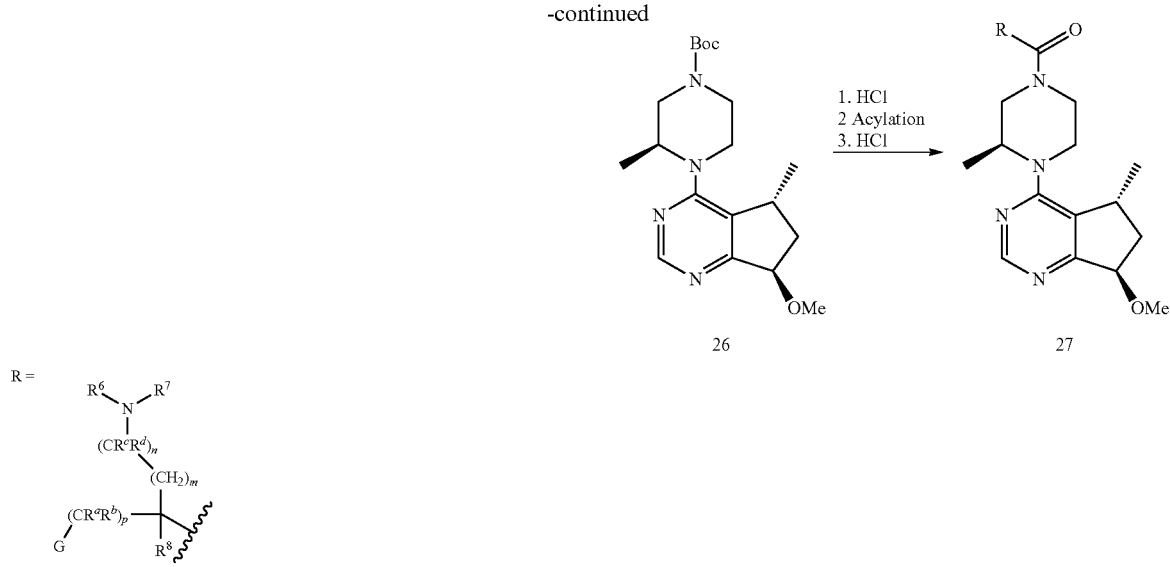

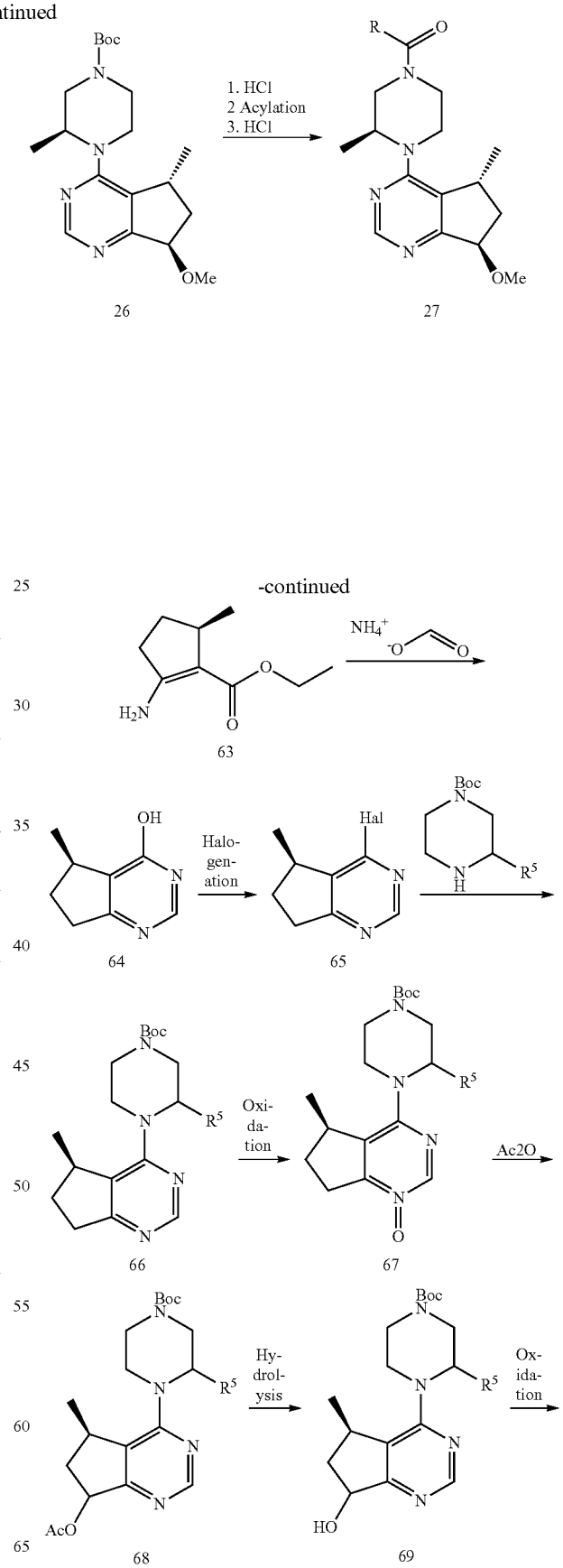

Scheme 2 shows a method of preparing compounds 22, 25 and 27 of Formula I wherein R', $R^2$ and $R^5$ are methyl. According to Scheme 2, bromination of (+)-pulegone 11 with bromine gives the dibromide 12. The treatment of the dibromide 12 with a base such as sodium ethoxide provides the pulegenate 13. Ozonolysis of the pulegenate 13 gives the ketoester 14. Treatment of the keto ester 14 with thiourea in the presence of a base such as KOH in ethanol, followed by reduction of the mercapto group under standard conditions (e.g., Raney Ni catalyst in ammonia) affords the hydroxypyrimidine 16. Chlorination of the hydroxypyrimidine 16 under standard conditions (e.g., $POCl_3$) provides the 4-chloropyrimidine 17. The oxidation of the 4-chloropyrimidine 17 with an oxidizing agent such as MCPBA or hydrogen peroxide provides the N-oxide 18. Rearrangement of the N-oxide 18 with acetic anhydride yields the intermediate 19. Compound 19 is reacted with the desired piperazine according to the procedure described in Scheme 1 to provide compound 20 where $R^5$ is H and 23 where $R^5$ is Me. Compounds 20 and 23 are subjected to chiral separation using HPLC with chiral stationary and then hydrolyzed upon treatment with a base such as lithium hydroxide to provide compounds 21 and 24, respectively. After deprotection, compounds 21 and 24 are then reacted with the appropriate amino acid to provide compounds 22 and 25, respectively.

Alternatively, the 7-hydroxy group of compound 24 may be alkylated with an alkylation reagent such as an alkyl halide in the presence of a base such as NaH or KOH to provide compound 26 where $R^2$ is Me. After deprotection, compound 26 is then reacted with the appropriate amino acid to provide compound 27.

Scheme 3

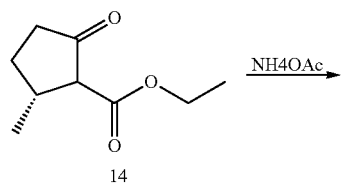

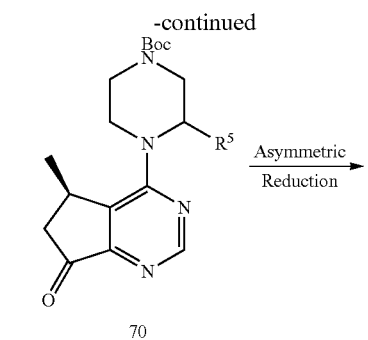

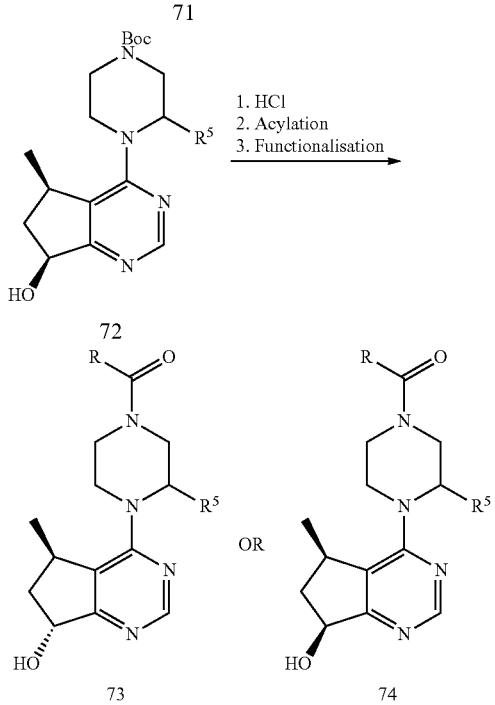

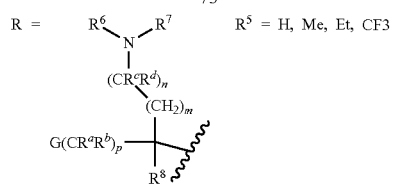

erazine at 0° C. to 150° C. gives the piperazine 66. Oxidation, using, for example, m-chloroperoxybenzoic acid ("MCPBA" or "m-CPBA") or Oxone® at −20° C. to 50° C. gives the N-oxide 67. Treatment with an acylating agent (e.g., acetic anhydride) followed by heating (40° C. to 200° C.) causes rearrangement to give 68. Hydrolysis, using, for example LiOH or NaOH at 0° C. to 50° C. gives the alcohol 69. Oxidation, using for example, Swern conditions, $MnO_4$ or pyridine-$SO_3$ complex at appropriate temperatures gives the ketone 70. Asymmetric reduction using, for example, a catalytic chiral catalyst in the presence of hydrogen, the CBS catalyst or a borohydride reducing agent in the presence of a chiral ligand gives rise to either the (R) or the (S) stereochemistry at the alcohol 71 or 72. Alternatively, a non-chiral reducing agent could be used (e.g., $H_2$, Pd/C), allowing the methyl group on the cyclopentane unit to provide facial selectivity and ultimately diastereoselectivity. If the reduction gives a lower diastereoselctivity, the diastereomers could be separated by (for example) chromatography, crystallization or derivitization. Finally deprotection of the Boc-group, using, for example, acid at 0° C. to 50° C., acylation using an appropriately functionalized amino acid and final functionalization of the amine of this amino acid (e.g., removal of any protecting group, alkylation, reductive amination or acylation to introduce new substituents) gives rise to the final compounds 73 and 74.

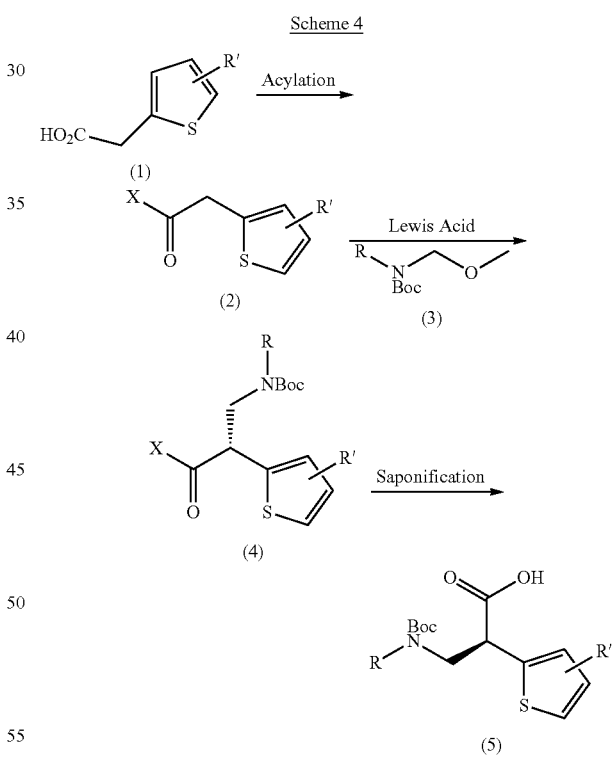

Scheme 3 shows an alternative method of preparing compounds 73 and 74. According to Scheme 3, amination of 14 using an ammonia synthon gives 63. Pyrimidine formation using, for example, ammonium formate in the presence of formamide at 50° C.-250° C. and/or at high pressure gives the bicyclic unit 64. Activation of 64 using, for example, $POCl_3$ or $SOCl_2$ gives the activated pyrimidine 65. Displacement of this leaving group, using a suitable protected/substituted pip- Introduction of a chiral auxiliary (e.g., Evans oxazolidinone, etc.) to compound 1 may be accomplished by standard acylation procedures to give the conjugate 2. For example, treatment of the acid with an activating agent (e.g., $COCl_2$) or mixed anhydride formation (e.g., 2,2-dimethylpropanoyl chloride) in the presence of an amine base at −20° C. to 100° C. followed by treatment with the appropriate chiral auxiliary (X)□ gives compound 2. The stereochemistry and choice of the chiral auxiliary may determine the stereochemistry of the newly created chiral center and the diastereoselectivity.

Treatment of compound 2 with a Lewis acid (e.g., TiCl$_4$) at low temperature (e.g., −20° C. to −100° C.) and an amine base (e.g., Hunig's base) followed by the use of an appropriately substituted imminium ion precursor 3 at low temperature then gives rise to compound 4. The temperature, Lewis acid and chiral auxiliary may all be expected to influence the diastereoselectivity of the addition adduct. Finally, saponification under mild conditions (e.g., LiOH/H$_2$O at −10° C. to 30° C.) gives rise to the desired acid 5.

According, another aspect of this invention provides a method of preparing a compound of Formula I, comprising:

reacting a compound having the formula:

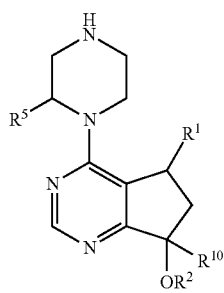

wherein R$^1$, R$^2$, R$^5$ and R$^{10}$ are as defined herein, with an amino acid having the formula:

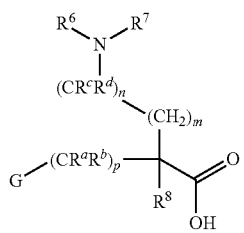

wherein R$^6$, R$^7$, R$^a$, R$^c$, R$^d$, G, m, n and p are as defined herein.

The amino acids used in the synthesis of compounds of Formula I as illustrated in Schemes 1-4 and in the Examples are either commercially available or may be prepared according to the methods disclosed herein. For example, in certain embodiments the amino acids used to prepare compounds of Formula I include β-phenylglycine amino acids having the Formula 1A, γ-phenylglycine amino acids having the Formula 2A, β-phenylalanine amino acids having the Formula 3A, and γ-phenylalanine amino acids having the Formula 4A.

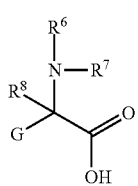

1A

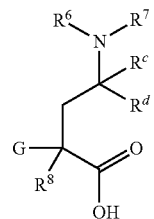

2A

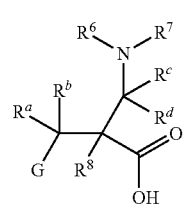

3A

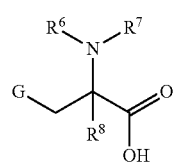

4A

Methods of preparing amino acids of Formulas 1A-4A are shown in Schemes A-J.

Scheme A

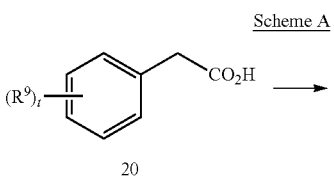

20

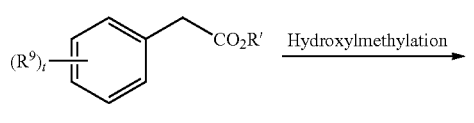

21

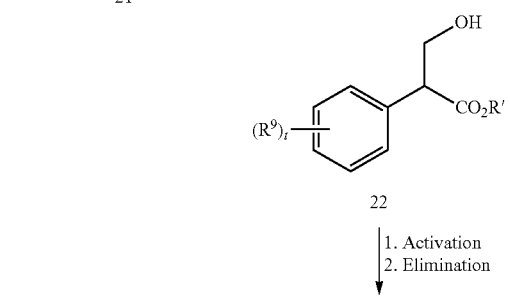

22

1. Activation
2. Elimination

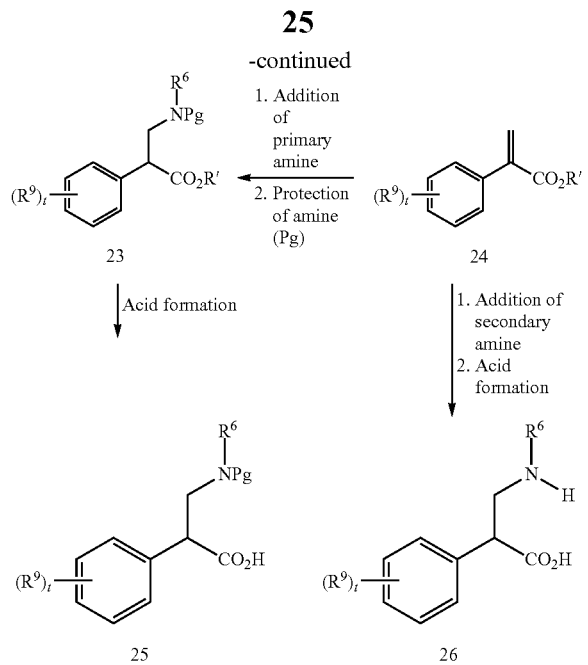

Scheme A illustrates a method of preparing optionally substituted β-phenylglycine amino acids 25 and 26 of the Formula 1A wherein $R^8$ is H, and $R^6$, and $R^9$ and are as defined herein, t is 0 to 4, and $R^7$ is H or an amine protecting group. According to Scheme A, the acid 20 is converted to an ester 21 wherein R' is alkyl using standard conditions such as treatment with an appropriate alcohol (e.g., MeOH) in the presence of a catalytic amount of an acid such as concentrated $H_2SO_4$ or a coupling agent such as DCC/DMAP; or alternatively by treatment with an appropriate electrophile (e.g., Me, EtBr, BnBr) in the presence of a base such as $NEt_3$/DMAP at an appropriate temperature (e.g., −20° C. to 100° C.). The appropriate choice of ester is determined by the conditions required to reform the acid at the end of the synthesis, with many appropriate examples and conditions being listed in 'Protective Groups in Organic Synthesis' by Greene and Wuts, Wiley-Interscience, third edition, Chapter 5. Introduction of the hydroxymethyl group to provide compound 22 may be performed by treatment with an appropriate aldehyde (e.g., formaldehyde) in the presence of base such as NaOEt at an appropriate temperature (e.g., −20° C. to room temperature). Activation of the alcohol group of compound 22 to form a leaving group (e.g., a mesylate, tosylate, halide) may be accomplished by treatment with, for example, methanesulphonyl chloride in the presence of excess base such as $NEt_3$, DIPEA, or DBU at an appropriate temperature (e.g., −20° C. to room temperature). In many cases the olefin 24 can be isolated directly from this procedure, in other cases warming (30° C. to 100° C.) or additional base (e.g., DBU in the case of halide) may be required to complete the elimination to provide compound 24. The activated olefin 24 may be treated with the desired primary amine (e.g., ethylamine) in a suitable solvent, such as THF, at an appropriate temperature (e.g., −20° C. to reflux) to generate the amino ester intermediate. In the case wherein compound 24 has an electron rich aromatic ring or electron poor/bulky primary amine, heating (e.g., 30-240° C. in a sealed tube) or microwave chemistry may be required. Protection of the amine group (for example as Boc-group) may be accomplished using $Boc_2O$ under standard conditions to provide compound 23 wherein Pg is a protecting group. Alternative protecting groups may be used, and many appropriate examples are listed in 'Protective Groups in Organic Synthesis' by Greene and Wuts, Wiley-Interscience, third edition, Chapter 7. Saponification of the ester 23 to form the protected amino acid 25 may be accomplished using conditions appropriate for the ester (e.g., aqueous LiOH for methyl esters, hydrogenation for benzyl esters, acid for t-butyl esters).

Alternatively, the activated olefin 24 may be treated with a secondary amine (e.g., diethylamine) in a suitable solvent such as THF at an appropriate temperature (e.g., −20° C. to reflux) to generate the aminoester intermediate (not shown). In the case wherein compound 24 has an electron rich aromatic ring or electron poor/bulky secondary amine, heating (e.g., 30-240° C. in a sealed tube) or microwave chemistry may be required. Saponification of the ester to form the amino acid 26 may be accomplished using conditions appropriate for the ester (e.g., aqueous LiOH for methyl esters, hydrogenation for benzyl esters, acid for t-butyl esters, etc.).

In an alternative to Scheme A, Pg may be substituted with $R^7$ in compounds 23 and 25.

Scheme A1

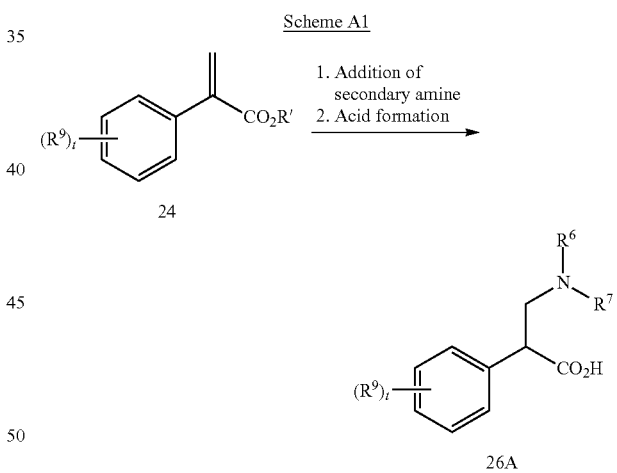

Scheme A1 shows an alternative to Scheme 1, wherein the activated olefin 24 is reacted to form the amino acid 26A.

Scheme B

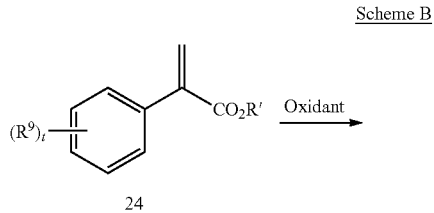

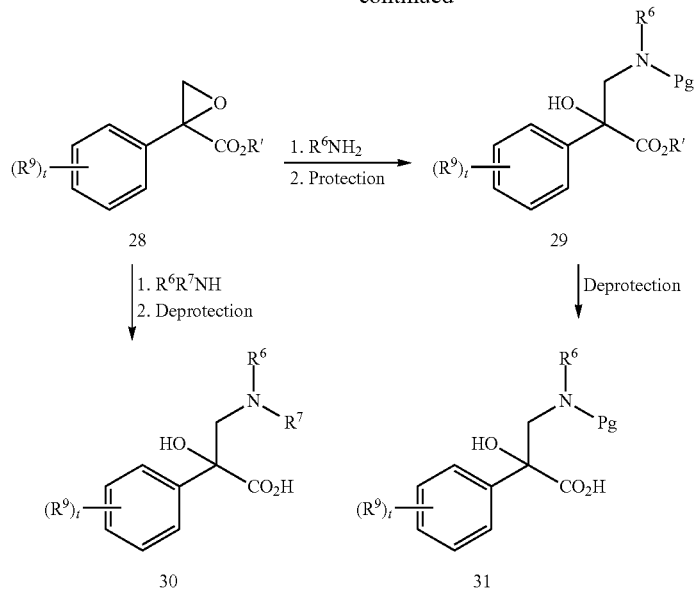

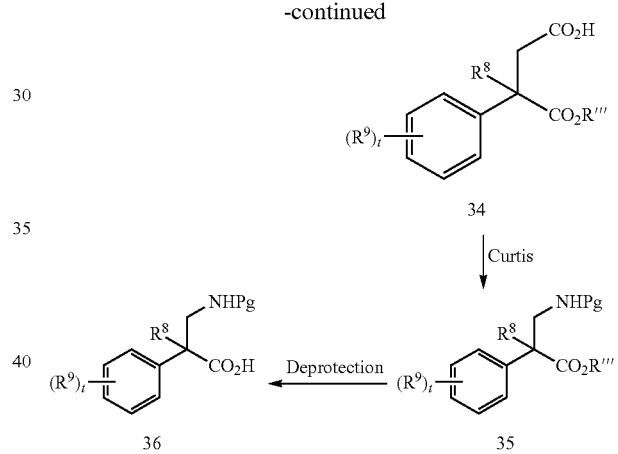

Scheme B shows a method of preparing optionally substituted β-phenylglycine amino acids 30 and 31 of Formula 1A wherein $R^8$ is OH, and $R^6$, and $R^9$ are as defined herein, t is 0 to 4, and $R^7$ is as defined herein or an amine protecting group. Oxidation of the unsaturated ester 24 (prepared according to Scheme A), wherein t is 0-4 and R' is alkyl, using a standard oxidizing agent such as MCPBA at an appropriate temperature (room temperature to reflux) provides the epoxide intermediate 28. Intermediate 28 may be treated with an appropriate amine, typically at high temperature (e.g., 50-300° C.) and high pressure (e.g., in a sealed tube or a bomb) to give the amino alcohol 29 or 30. If a secondary amine is used (such as in the preparation of compound 30), then deprotection of the ester using conditions listed in 'Protective Groups in Organic Synthesis' by Greene and Wuts, Wiley-Interscience, third edition, Chapter 5 may be used (e.g., LiOH for a methyl ester, hydrogenation for a benzyl ester, etc). When a primary amine is used (such as in the preparation of compound 29), protection of the amine (e.g., as a Boc-group using Boc anhydride) followed by deprotection of the ester (using the above conditions) provide the hydroxylated amino acid 31.

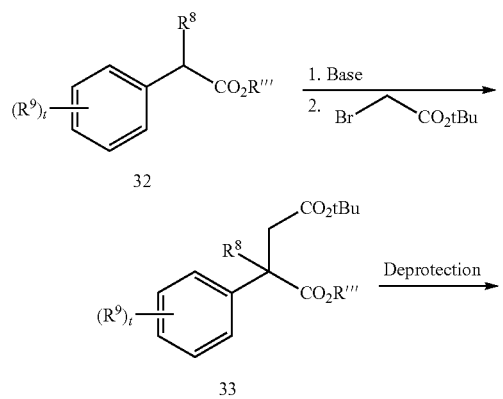

Scheme C shows a method of preparing optionally substituted β-phenylglycine amino acids 36 of the Formula 1A wherein $R^8$ is methyl, $R^6$ is H, $R^7$ is an amine protecting group t is 0 to 4, and $R^9$ is as defined herein. The ester 32, wherein R''' is alkyl, can be treated with a base (e.g., NaOtBu) at an appropriate temperature (e.g., 0° C. to reflux) to form the anion, followed by addition of an electrophile (e.g., tert-butyl 2-bromoacetate) at an appropriate temperature (e.g., −78° C. to room temperature) to give the homologated ester 33. Removal of the t-butyl ester of compound 33 using an appropriate acid such as TFA or HCl at an appropriate temperature (e.g, 0° C. to reflux) provides compound 34. A Curtius rearrangement of compound 34 using, for example, DPPA in the presence of mild base such as $NEt_3$ at an appropriate temperature (e.g., 0° C. to reflux), followed by treatment of the reactive intermediate with an alcohol (e.g., t-BuOH), optionally in the presence of a Lewis acid (e.g., $SnCl_2$) at higher temperature (e.g., 40-200° C.) provides compound 35 wherein Pg is an amine protecting group. The choice of alcohol used to prepare compound 35 determines the amine protecting group (e.g., t-BuOH provides the Boc-amine). Deprotection of the ester group of compound 35 using standard conditions (e.g., with LiOH when the protecting group is a methyl ester, hydrogenation for a benzyl ester, etc.) gives the acid compound 36.

In one alternative of Scheme C, $R^8$ may be methyl, H or F.

In another alternative of Scheme C, Pg may be substituted with $R^7$ in compounds 35 and 36.

Scheme D

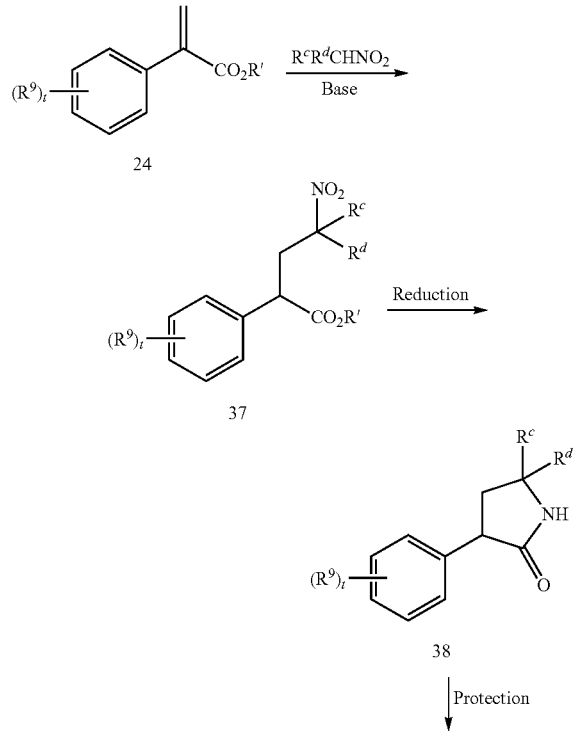

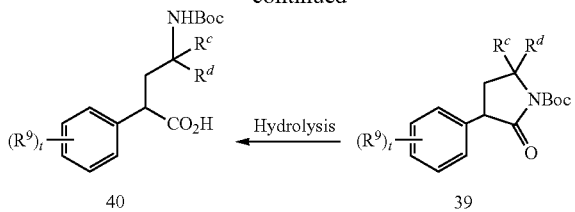

Scheme D shows a method of preparing optionally substituted γ-phenylglycine amino acids 40 of Formula 2A wherein $R^c$, $R^d$, and $R^9$ are as defined herein t is 0 to 4, $R^6$ is H, and $R^7$ is an amine protecting group such as Boc. The starting unsaturated ester 24, prepared according to Scheme A, can be treated with a substituted nitromethane derivative (e.g., nitroethane) in the presence of a base such as DBU at an appropriate temperature (e.g., 0° C. to room temperature) to give the homologated adduct 37. The nitro group of compound 37 can be reduced using standard conditions (e.g., hydrogenation, Zn/acid, etc.) at an appropriate temperature (e.g., room temperature to reflux), and the resulting intermediate can be cyclized to give the lactam intermediate 38. Protection of the amine, for example with a Boc-group to provide compound 39, may be accomplished using Boc$_2$O under standard conditions. Alternative protecting groups may be used, and many appropriate examples are listed in 'Protective Groups in Organic Synthesis' by Greene and Wuts, Wiley-Interscience, third edition, Chapter 7. Treatment of compound 39 with an aqueous base such as LiOH or KOH at an appropriate temperature (e.g., 0 to 100° C.) effects ring opening of the lactam to give the appropriately substituted protected amino acid compound 40.

In one alternative of Scheme D, Boc may be replaced with $R^7$ in compounds 39 and 40.

Scheme D1

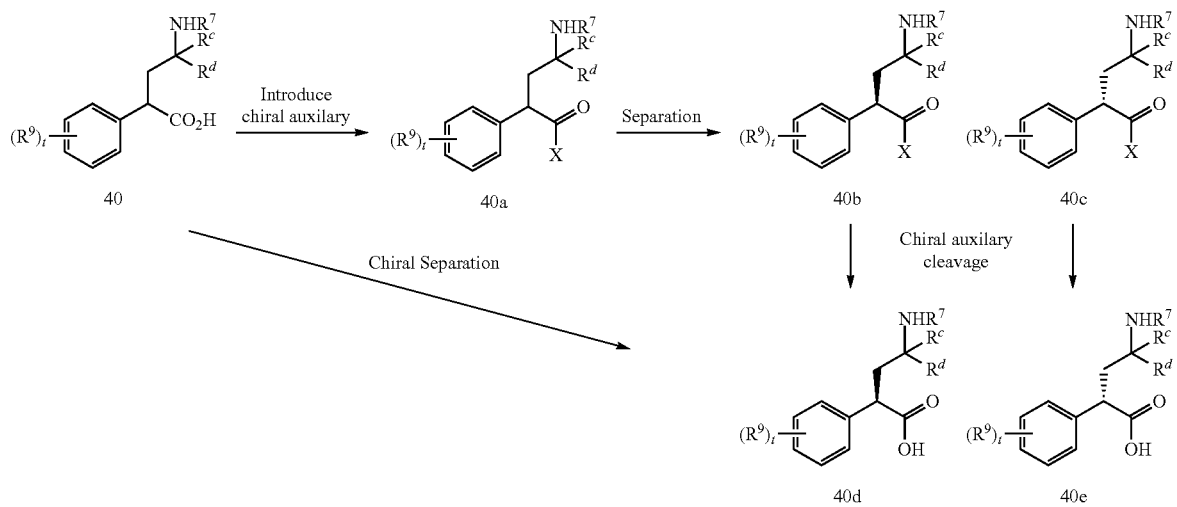

Scheme D1 shows representative methods of forming the single enantionmers of the gamma amino acids 40d and 40e, wherein $R^c$, $R^d$, and $R^9$ are as defined herein, t is 0 to 4, $R^6$ is H, and $R^7$ is an amine protecting group such as Boc. In one possible method, the racemic amino acid is subject to chiral chromatographic separation using a chiral stationary phase. Alternatively, a diastereomeric mixture may be prepared which could be separated by conventional chromatographic techniques. For example, activation of compound 40 (e.g., $COCl_2$, base) and introduction of a chiral auxiliary (e.g., an Evans' oxazolidinone) in the presence of a basic amine (e.g., Hunig's base) at −20° C. to 50° C. gives the diastereomeric mixture of compounds 40b and 40c. This mixture may be separated using standard conditions (e.g., column chromatography, HPLC, SFC, etc.) to give the individual diastereomers. These may be converted to the desired acids by cleavage of the chiral auxiliary (in the case of an Evans' auxiliary, by using (for example) LiOH/HOOH at −15° C. to room temperature) to give the compounds 40d and 40e. The temperature may need to be kept low so as to prevent racemisation of the newly separated chiral center.

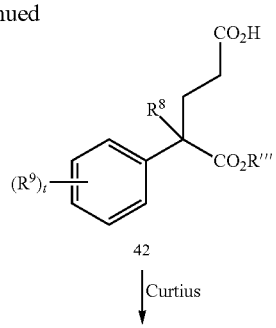

Scheme E shows a method of making optionally substituted γ-phenylglycine amino acids 44 of Formula 2A wherein $R^8$ is methyl, $R^6$ is H, $R^7$ is an amine protecting group, t is 0 to 4, and $R^9$ is as defined herein. The ester 32, wherein R''' is alkyl and t is 0-4, can be treated with a suitable base such as KOtBu at an appropriate temperature (e.g., 0° C. to reflux) to form the anion, followed by addition of an acrylate unit (e.g., t-butylacrylate) at a temperature ranging from −78° C. to room temperature to give the homologated ester 41. Saponification of the t-butyl ester of compound 41 by treatment with a suitable acid such as TFA or HCl at an appropriate temperature (e.g, 0° C. to reflux) provides compound 42. A Curtius rearrangement of compound 42 using, for example, DPPA in the presence of mild base such as $NEt_3$ at an appropriate temperature (e.g., 0° C. to reflux), followed by treatment of the reactive intermediate with an appropriate alcohol (e.g., tBuOH), optionally in the presence of a Lewis acid (e.g., $SnCl_2$) at elevated temperatures (e.g., 40-200° C.) provides compound 43. The choice of alcohol determines the amine protecting group of compound 43 (e.g., tBuOH provides the Boc-amine). Deprotection of the ester of compound 43 under standard conditions (e.g., LiOH for a methyl ester, hydrogenation for a benzyl ester, etc.) gives the acid 44.

In one alternative to Scheme E, Pg may be substituted with $R^7$ in compounds 43 and 44.

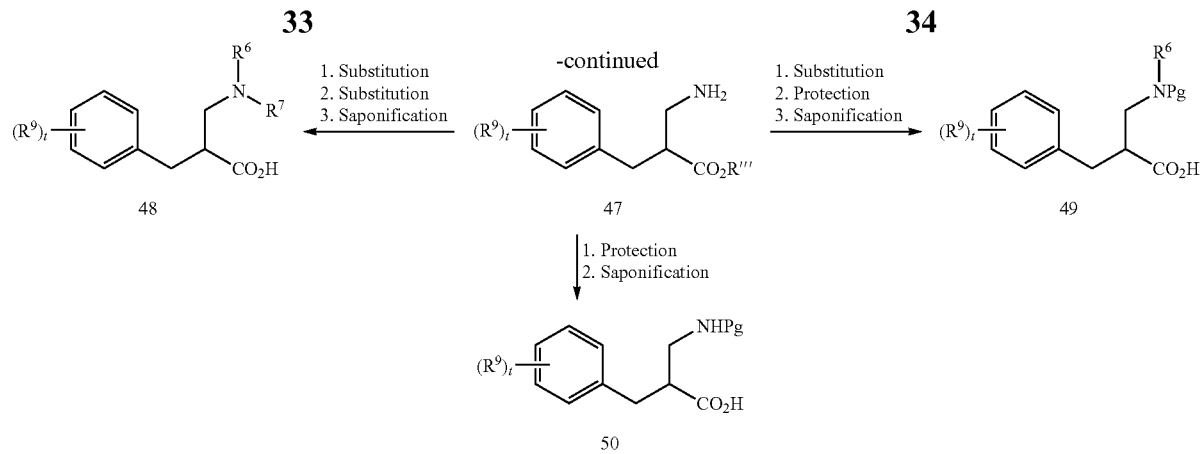

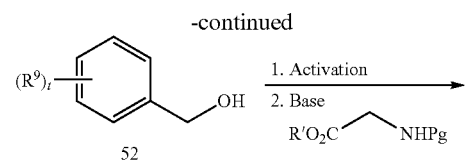

Scheme F shows a method of preparing optionally substituted β-phenylalanine amino acids 48, 49 and 50 of Formula 3A wherein $R^6$ is H, $R^7$ is an amine protecting group, t is 0 to 4, and $R^9$ is as defined herein. An appropriately substituted aldehyde 45 can be treated with a cyanoacetate of the formula CN—$CH_2CO_2R'''$ wherein R''' is alkyl (e.g., ethyl 2-cyanoacetate) in the presence of a suitable base such as piperidine at an appropriate temperature (e.g., room temperature to reflux) to give the unsaturated ester 46. Reduction of the olefin and the nitrile groups of compound 46 to provide compound 47 may be accomplished in a number of ways. For example, the olefin may be reduced with any agent known to effect 1,4-reductions, such as $NaBH_4$. The nitrile may be reduced using agents such as $LiAlH_4$ or $NaBH_4$ in the presence of a Lewis acid such as $BF_3.OEt_2$ or TFA. A number of alternative reducing agents may be used, such as those listed in 'Reductions in Organic Chemistry' by Hudlicky, ACS monograph, $2^{nd}$ edition, Chapter 18. If desired, the primary amine 47 can be monoalkylated or bisalkylated at this stage using standard conditions (e.g., reductive amination using an appropriate aldehyde, Lewis acid and reducing agent) to provide intermediates (not shown) en route to compounds 48 and 49. To prepare primary and secondary amines, protection may be accomplished using any number of protecting groups (e.g., 'Protective Groups in Organic Synthesis' by Greene and Wuts, Wiley-Interscience, third edition, Chapter 7), for example as a Boc-group using Boc anhydride at 0° C. to room temperature. Cleavage of the ester group to form the amino acid 48, 49 or 50 may be accomplished using an aqueous bases such as LiOH or KOH, or any of the alternative reagents listed in the aforementioned 'Protecting Groups' text (e.g., hydrogenation for a benzyl ester).

In one alternative to Scheme F, Pg may be substituted with $R^7$ in compounds 49 or 50.

Scheme G

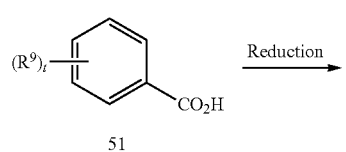

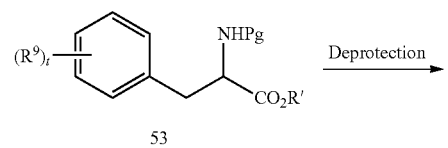

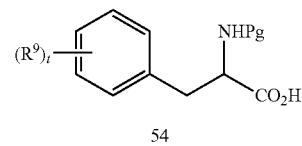

Scheme G shows a method of preparing optionally substituted α-phenylalanine amino acids 54 of Formula 4A, wherein $R^6$ is H, $R^7$ is an amine protecting group, t is 0 to 4, and $R^9$ is as defined herein. An appropriately substituted acid 51 may be reduced to the benzyl alcohol 52 using for example $LiAlH_4$ at a temperature ranging from room temperature to reflux. The alcohol group of compound 52 can be activated as a leaving group (e.g., halide, mesylate, etc.) using, for example, $PBr_3$, MsCl/$NEt_3$, etc. Displacement of this leaving group using a protected glycine derivative such as ethyl 2-(diphenylmethyleneamino)acetate in the presence of strong base such as LDA, nBuLi provides the amino ester intermediate 53 wherein $R^1$ is alkyl and Pg is a protecting group. Appropriate protecting groups are listed in 'Protective Groups in Organic Synthesis' by Greene and Wuts, Wiley-Interscience). The amine protecting group may be changed at this stage, for example to introduce a Boc-group. Subsequent deprotection of the ester 53 (e.g., using 3N HCl, LiOH, hydrogenation for a benzyl ester, etc.) at an appropriate temperature (e.g., 0° C. to reflux) provides the desired N-protected amino acid 54.

In one alternative to Scheme G, Pg may be substituted with $R^7$ in compound 54 after the deprotection of compound 53.

Scheme H

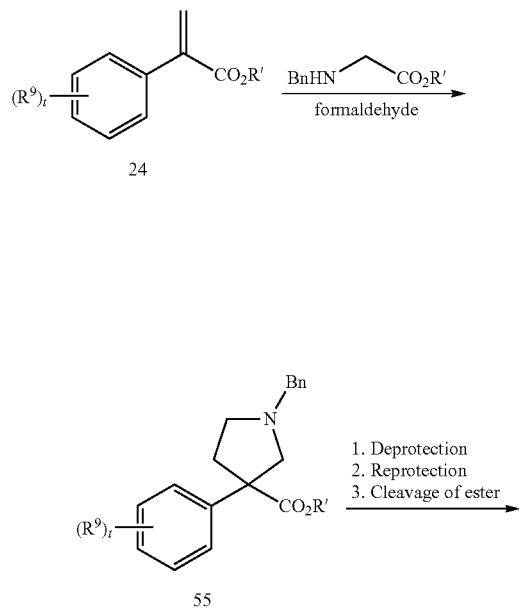

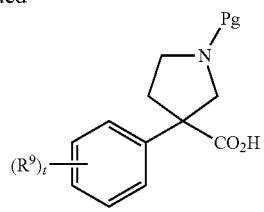

Scheme H shows a method of preparing optionally substituted γ-phenylglycine amino acids 56 of Formula 2A wherein $R^6$ and $R^8$ together with the atoms to which they are attached form a spirocyclic heterocyclic ring, $R^7$ is an amine protecting group, t is 0 to 4, and $R^9$ is as defined herein. According to Scheme H, the unsaturated ester 24 can be treated with a suitably protected glycine derivative (e.g., benzylglycine) and formaldehyde under dry conditions (e.g., with addition of molecular sieves) at an appropriate temperature (e.g., room temperature to reflux) to generate compound 55. Cleavage of the benzyl group using standard conditions (e.g., via hydrogenation, 1-chloroethylformate, etc.) followed by addition of an amine protecting group such as a Boc-group and cleavage of the ester under standard conditions (e.g., LiOH for a methyl ester, acid for a t-butyl ester, etc., at 0° C. to reflux) provides the N-protected amino acid 56.

In one alternative to Scheme H, Pg may be substituted with $R^7$ in compound 56.

Scheme I

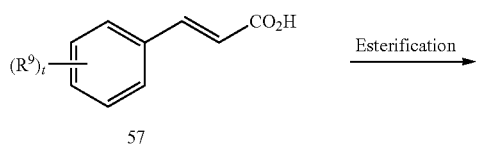

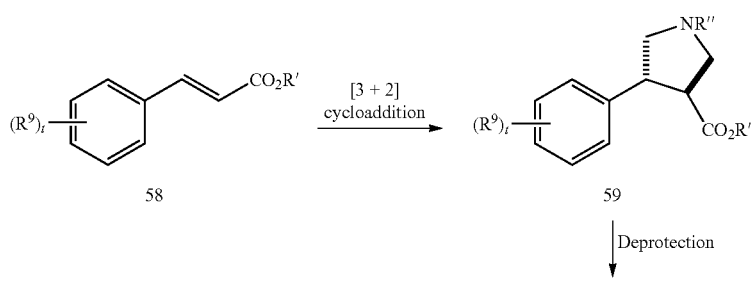

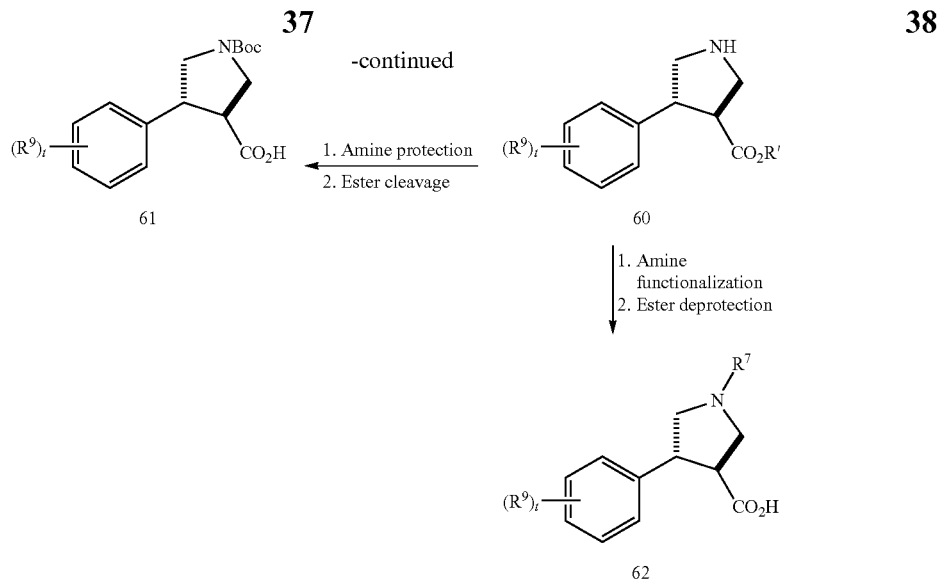

Scheme I shows a method of preparing optionally substituted β-phenylalanine amino acids 61 and 62 of Formula 3A wherein $R^6$ and $R^b$ together with the atoms to which they are attached form a heterocyclic ring, and $R^7$ and $R^9$ are as defined herein and t is 0 to 4. The acid 57 is converted to an ester 58 using standard conditions such as treatment with an appropriate alcohol (e.g., MeOH) in the presence of either catalytic acid (e.g., concentrated $H_2SO_4$ or TMSCl) or a coupling agent (e.g., DCC/DMAP); or alternatively by treatment with an appropriate electrophile (e.g., MeI, EtBr, BnBr) in the presence of a suitable base such as $NEt_3$/DMAP at appropriate temperatures (e.g., −20° C. to 100° C.). The appropriate choice of ester is determined by the conditions required to reform the acid at the end of the synthesis, such as described in 'Protective Groups in Organic Synthesis' by Greene and Wuts, Wiley-Interscience, third edition, Chapter 5. Cyclization of compound 58 to provide compound 59 may be achieved using, for example, N-(methoxymethyl)(phenyl)-N-((trimethylsilyl)methyl)methanamine in the presence of TFA. This particular set of reagents generates the benzylamine, which can be cleaved to provide compound 60 under standard conditions such as such as hydrogenation at −20° C. to 50° C. or any other standard conditions such as those listed in 'Protective Groups in Organic Synthesis' by Greene and Wuts, Wiley-Interscience, third edition, Chapter 7. Protection of the free amine of compound 60 with an alternative protecting group (e.g., Boc) using reagents listed in the aforementioned text, such as Boc-anhydride, followed by cleavage of the ester using standard conditions appropriate for the ester (e.g., aqueous LiOH for methyl esters, hydrogenation for benzyl esters, acid for t-butyl esters) provides the acid compound 61. Alternatively, the free amine can be functionalized further (e.g., using alkylation, reductive amination, or acylation conditions), followed by ester cleavage to generate the tertiary amino acid compound 62.

Scheme J

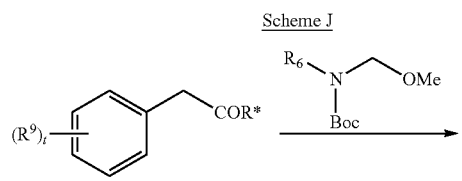

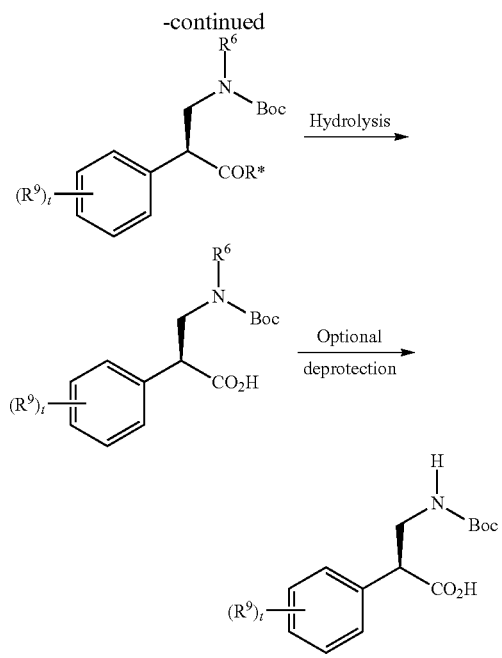

Either enantiomer of the b-amino acids may be prepared using a procedure such as that shown in Scheme J. A 2-phenylacetate coupled with an appropriate chiral auxiliary (R*) (for example, an Evans' auxiliary or a Sultam) with the appropriate stereochemistry to generate the desired chemistry at the b-position of the amino acid may be treated with an imine or iminium ion synthon (e.g., prepared in situ by the presence of a Lewis acid (e.g., $TiCl_4$) and an appropriately substituted alkoxymethanamine or N-(alkoxymethyl)amide/carbamate at −100° C. to 50° C.). The asymmetric addition may require the presence of Lewis acids (e.g., $TiCl_4$), amine bases (e.g., Hunig's base) and lower temperatures (e.g., −100° C. to 0° C.) to generate the best levels of stereochemical induction. If the de is lower than required, the separate diastereomers may be separated at this stage by (for example) chromatography or crystallization. Cleavage of the chiral auxiliary, using methods known to cleave the chosen auxiliary (e.g., $LiOH/H_2O_2$ at −50° C. to 50° C. for the Evans auxiliary) then leads to the desired N-protected b-amino acid with the desired stereochemistry at the b-position. Additionally, if $R^6$ is also a protecting group (e.g., 2,4-dimethoxybenzyl), it may be removed in the presence of the Boc-group (e.g., hydrogenation or DDQ, etc.) to give the Boc-amino acid, which upon removal of the Boc-group would provide the primary amine, which may be further functionalized by alkylation, acylation or reductive amination (either prior to or after coupling with the pyrimidine-piperazine unit).

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. of Chromatogr., (1990) 513: 375-378). Enriched or purified enantiomers can be distinguished by methods used to distinguish other chiral molecules with asymmetric carbon atoms, such as optical rotation and circular dichroism.

Chemotherapeutic Agents

Certain chemotherapeutic agents have demonstrated surprising and unexpected properties in combination with a compound of formula I or a pharmaceutically acceptable salt thereof in inhibiting cellular proliferation in vitro and in vivo. Such chemotherapeutic agents include: 5-FU, a platinum agent, irinotecan, docetaxel, doxorubicin, gemcitabine, SN-38, capecitabine, temozolomide, erlotinib, PD-0325901, paclitaxel, bevacizumab, pertuzumab, tamoxifen, rapamycin, lapatinib, vemurafenib, MDV3100, abiraterone, and GDC-0973.

5-FU (fluorouracil, 5-fluorouracil, CAS Reg. No. 51-21-8) is a thymidylate synthase inhibitor and has been used for decades in the treatment of cancer, including colorectal and pancreatic cancer (U.S. Pat. No. 2,802,005; U.S. Pat. No. 2,885,396; Duschinsky et al (1957) J. Am. chem. Soc. 79:4559; Hansen, R. M. (1991) Cancer Invest. 9:637-642). 5-FU is named as 5-fluoro-1H-pyrimidine-2,4-dione.

Carboplatin (CAS Reg. No. 41575-94-4) is a chemotherapeutic drug used against ovarian carcinoma, lung, head and neck cancers (U.S. Pat. No. 4,140,707; Calvert et al (1982) Cancer Chemother. Pharmacol. 9:140; Harland et al (1984) Cancer Res. 44:1693). Carboplatin is named as azanide; cyclobutane-1,1-dicarboxylic acid; platinum.

Cisplatin, cisplatinum, or cis-diamminedichloroplatinum (II) (CAS Reg. No. 15663-27-1) is a chemotherapeutic drug used to treat various types of cancers, including sarcomas, some carcinomas (e.g., small cell lung cancer, and ovarian cancer), lymphomas, and germ cell tumors. It was the first member of a class of platinum-containing anti-cancer drugs, which now also includes carboplatin and oxaliplatin. Cisplatin has the structure cis-$PtCl_2(NH_3)_2$.

Oxaliplatin (CAS Reg. No. 63121-00-6) is a coordination complex that is used in cancer chemotherapy (U.S. Pat. No. 4,169,846). Oxaliplatin has been compared with other platinum compounds (Cisplatin, Carboplatin) in advanced cancers (gastric, ovarian). Oxaliplatin is typically administered with fluorouracil and leucovorin in a combination known as FOLFOX for the treatment of colorectal cancer.

Irinotecan (CAS Reg. No. 97682-44-5) is a topoisomerase 1 inhibitor, which prevents DNA from unwinding. Irinotecan is activated by hydrolysis to SN-38, an inhibitor of topoisomerase I. The inhibition of topoisomerase I by the active metabolite SN-38 eventually leads to inhibition of both DNA replication and transcription. Its main use is in colon cancer, in particular, in combination with other chemotherapy agents. This includes the regimen FOLFIRI, which consists of infusional 5-fluorouracil, leucovorin, and irinotecan.

Doxorubicin (CAS Reg. No. 23214-92-8) is an anthracycline antibiotic. Like all anthracyclines, it works by intercalating DNA. Doxorubicin is commonly used in the treatment of a wide range of cancers, including hematological malignancies, many types of carcinoma, and soft tissue sarcomas. Doxorubicin is named as (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione.

Docetaxel (CAS Reg. No. 114977-28-5) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561; Mangatal et al (1989) Tetrahedron 45:4177; Ringel et al (1991) J. Natl. Cancer Inst. 83:288; Bissery et al (1991) Cancer Res. 51:4845; Herbst et al (2003) Cancer. Treat. Rev. 29:407-415; Davies et al (2003) Expert. Opin. Pharmacother. 4:553-565). Docetaxel is named as (2R,3S)—N-carboxy-3-phenylisoserine, N-tert-butyl ester, 13-ester with 5, 20-epoxy-1,2,4,7,10,13-hexahydroxytax-11-en-9-one 4-acetate 2-benzoate, trihydrate (U.S. Pat. No. 4,814,470; EP 253738; CAS Reg. No. 114977-28-5).

Folinic acid (INN) or leucovorin (USAN) ((2S)-2-{[4-[(2-amino-5-formyl-4-oxo-5,6,7,8-tetrahydro-1H-pteridin-6-yl)methylamino]benzoyl]amino}pentanedioic acid, CAS Reg. No. 1492-18-8), generally administered as calcium or sodium folinate (or leucovorin calcium/sodium), is used in cancer chemotherapy involving the synergistic combination with the chemotherapy agent 5-fluorouracil, and in certain embodiments with oxaliplatin as part of the regimen FOLFOX. It has the structure:

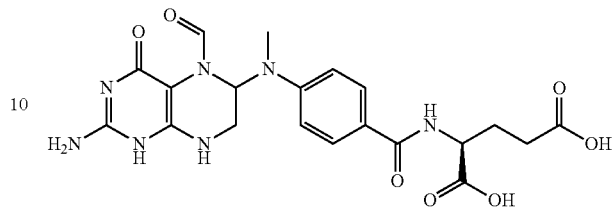

Gemcitabine (CAS Reg. No. 95058-81-4) is a nucleoside analog which blocks DNA replication, is used to treat various carcinomas including pancreatic, breast, NSCLC, and lymphomas (U.S. Pat. No. 4,808,614; U.S. Pat. No. 5,464,826; Hertel et al (1988) J. Org. Chem. 53:2406; Hertel et al (1990) Cancer Res. 50:4417; Lund et al (1993) Cancer Treat. Rev. 19:45-55). Gemcitabine is named as 4-amino-1-[3,3-difluoro-4-hydroxy-5-(hydroxymethyl)tetrahydrofuran-2-yl]-1H-pyrimidin-2-one.

SN-38 (CAS Reg. No. 86639-52-3) is the active metabolite of irinotecan (see above). It is 200 times more active than irinotecan itself. It has the name 7-ethyl-10-hydroxy-camptothecin.

Capecitabine (CAS Reg. No. 154361-50-9) is an orally-administered chemotherapeutic agent used in the treatment of metastatic breast and colorectal cancers. Capecitabine is a prodrug, that is enzymatically converted to 5-fluorouracil in the tumor, where it inhibits DNA synthesis and slows growth of tumor tissue. The activation of capecitabine follows a pathway with three enzymatic steps and two intermediary metabolites, 5'-deoxy-5-fluorocytidine (5'-DFCR) and 5'-deoxy-5-fluorouridine (5'-DFUR), to form 5-fluorouracil. Capecitabine has the name pentyl[1-(3,4-dihydroxy-5-methyl-tetrahydrofuran-2-yl)-5-fluoro-2-oxo-1H-pyrimidin-4-yl]aminomethanoate.

Temozolomide (CAS Reg. No. 85622-93-1) is an alkylating agent which can be used for the treatment of Grade IV astrocytoma, also known as glioblastoma multiforme as well as Melanoma, a form of skin cancer. Temozolomide has the name 4-methyl-5-oxo-2,3,4,6,8-pentazabicyclo[4.3.0]nona-2,7,9-triene-9-carboxamide.

Erlotinib (CAS Reg. No. 183321-74-6, TARCEVA®, OSI-774, Genentech) is used to treat non-small cell lung cancer (NSCLC), lung cancer, pancreatic cancer and several other types of cancer by specifically targeting the epidermal growth factor receptor (EGFR) tyrosine kinase (U.S. Pat. No. 5,747,498; U.S. Pat. No. 6,900,221; Moyer et al (1997) Cancer Res. 57:4838; Pollack et al (1999) J. Pharmcol. Exp. Ther. 291: 739; Perez-Soler et al (2004) J. Clin. Oncol. 22:3238; Kim et al (2002) Curr. Opin. Invest. Drugs 3:1385-1395; Blackhall et al (2005) Expert Opin. Pharmacother. 6:995-1002). Erlotinib is named as N-(3-ethynylphenyl)-6,7-bis(methoxymethoxy) quinazolin-4-amine (CAS Reg. No. 183321-74-6) and has the structure:

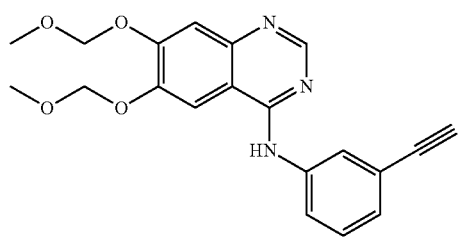 [SMILES: C#Cc1cccc(Nc2ncnc3cc(OCOC)c(OCOC)cc23)c1]

PD-0325901 (CAS Reg. No. 391210-10-9, Pfizer) is a second-generation, non-ATP competitive, allosteric MEK inhibitor for the potential oral tablet treatment of cancer (U.S. Pat. No. 6,960,614; U.S. Pat. No. 6,972,298; US 2004/147478; US 2005/085550). Phase II clinical trials have been conducted for the potential treatment of breast tumors, colon tumors, and melanoma. PD-0325901 is named as (R)—N-(2,3-dihydroxypropoxy)-3,4-difluoro-2-(2-fluoro-4-iodophenylamino)benzamide, and has the structure:

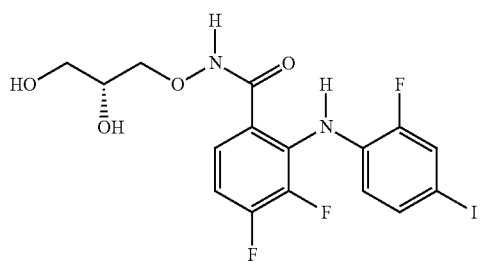 [SMILES: O=C(NOC[C@H](O)CO)c1ccc(F)c(F)c1Nc1ccc(I)cc1F]

Paclitaxel (CAS Reg. No. 33069-62-4, TAXOL®, Bristol-Myers Squibb Oncology, Princeton N.J.) is isolated the compound from the bark of the Pacific yew tree, *Taxus brevifolia*, and used to treat lung, ovarian, breast cancer, and advanced forms of Kaposi's sarcoma (Wani et al (1971) J. Am. Chem. Soc. 93:2325; Mekhail et al (2002) Expert. Opin. Pharmacother. 3:755-766). Paclitaxel is named as β-(benzoylamino)-α-hydroxy-,6,12b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b) oxet-9-ylester,(2aR-(2a-α,4-β,4a-β,6-β,9-α (α-R*,β-S*),11-α,12-α,12a-α,2b-α))benzenepropanoic acid, and has the structure:

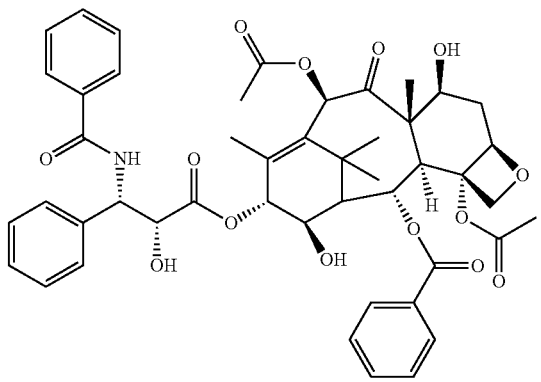 [SMILES: CC(=O)O[C@H]1C(=O)[C@@]2(C)[C@H]([C@H](OC(=O)c3ccccc3)C3[C@@H](O)[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Bevacizumab (CAS Reg. No. 216974-75-3, AVASTIN®, Genentech) is a recombinant humanized monoclonal antibody against VEGF, vascular endothelial growth factor (U.S. Pat. No. 6,054,297; Presta et al (1997) Cancer Res. 57:4593-4599). It is used in the treatment of cancer, where it inhibits tumor growth by blocking the formation of new blood vessels. Bevacizumab was the first clinically available angiogenesis inhibitor in the United States, approved by the FDA in 2004 for use in combination with standard chemotherapy in the treatment of metastatic colon cancer and most forms of metastatic non-small cell lung cancer. Several late-stage clinical studies are underway to determine its safety and effectiveness for patients with: adjuvant/non-metastatic colon cancer, metastatic breast cancer, metastatic renal cell carcinoma, metastatic glioblastoma multiforme, metastatic ovarian cancer, metastatic hormone-refractory prostate cancer, and metastatic or unresectable locally advanced pancreatic cancer (Ferrara et al (2004) Nat. Rev. Drug Disc. 3:391-400). Bevacizumab includes mutated human IgG1 framework regions and antigen-binding complementarity-determining regions from the murine anti-hVEGF monoclonal antibody A.4.6.1 that blocks binding of human VEGF to its receptors. Bevacizumab has a molecular mass of about 149,000 daltons and is glycosylated.

Bevacizumab and other humanized anti-VEGF antibodies are further described in U.S. Pat. No. 6,884,879. Additional anti-VEGF antibodies include the G6 or B20 series antibodies, e.g., G6-31, B20-4.1, (WO 2005/012359; WO 2005/044853; U.S. Pat. No. 7,060,269; U.S. Pat. No. 6,582,959; U.S. Pat. No. 6,703,020; U.S. Pat. No. 6,054,297; WO 98/45332; WO 96/30046; WO 94/10202; EP 0666868B1; US 2006/009360; US 2005/0186208; US 2003/0206899; US 2003/0190317; US 2003/0203409; 20050112126; Popkov et al (2004) Journal of Immunological Methods 288:149-164. A "B20 series antibody" is an anti-VEGF antibody that is derived from a sequence of the B20 antibody or a B20-derived antibody according to any one of FIGS. 27-29 of WO 2005/012359, the entire disclosure of which is expressly incorporated herein by reference. In one embodiment, the B20 series antibody binds to a functional epitope on human VEGF comprising residues F17, M18, D19, Y21, Y25, Q89, 191, K101, E103, and C104. Other anti-VEGF antibodies include those that bind to a functional epitope on human VEGF comprising residues F17, M18, D19, Y21, Y25, Q89, 191, K101, E103, and C104 or, alternatively, comprising residues F17, Y21, Q22, Y25, D63, 183 and Q89.

Trastuzumab (HERCEPTIN®, huMAb4D5-8, rhuMAb HER2, Genentech) is a recombinant DNA-derived humanized, IgG1 kappa, monoclonal antibody version of the murine HER2 antibody which selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al (1985) Science 230:1132-9; Slamon D J, et al (1989) Science 244:707-12). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137). HERCEPTIN® was approved in 1998 for the treatment of patients with ErbB2-overexpressing metastatic breast cancers (Baselga et al, (1996) J. Clin. Oncol. 14:737-744). The FDA approved HERCEPTIN® in 2006 as part of a treatment regimen containing doxorubicin, cyclophosphamide and paclitaxel for the adjuvant treatment of patients with HER2-positive, node-positive breast cancer. There is a significant clinical need for developing further HER2-directed cancer therapies for those patients with HER2-overexpressing tumors, or other diseases associated with HER2 expression that do not respond, or respond poorly, to HERCEPTIN® treatment.

Pertuzumab (OMNITARG™, rhuMab 2C4, Genentech) is a clinical stage, humanized antibody and the first in a new class of agents known as HER dimerization inhibitors (HDIs) which block the ability of the HER2 receptor to collaborate with other HER receptor family members, i.e. HER1/EGFR, HER3, and HER4 (U.S. Pat. No. 6,949,245; Agus et al (2002) Cancer Cell 2:127-37; Jackson et al (2004) Cancer Res 64:2601-9; Takai et al (2005) Cancer 104:2701-8). In cancer cells, interfering with HER2's ability to collaborate with other HER family receptors blocks cell signaling and may ultimately lead to cancer cell growth inhibition and death of the cancer cell. HDIs, because of their unique mode of action, have the potential to work in a wide variety of tumors, including those that do not overexpress HER2 (Mullen et al (2007) Molecular Cancer Therapeutics 6:93-100).

Temozolomide, (CAS Reg. No. 85622-93-1, TEMO-DAR®, TEMODAL®, Schering Plough) is a oral chemotherapy drug approved by the FDA for the treatment of anaplastic astrocytoma, and has been studied for other brain tumor types such as glioblastoma multiforme (U.S. Pat. No. 5,260,291; Stevens et al (1984) J. Med. Chem. 27:196; Newlands et al (1997) Cancer Treat. Rev. 23:35-61; Danson et al (2001) Expert Rev. Anticancer Ther. 1:13-19). Temozolomide is named as (4-methyl-5-oxo-2,3,4,6,8-pentazabicyclo [4.3.0]nona-2,7,9-triene-9-carboxamide or 3,4-dihydro-3-methyl-4-oxohnidazo[5,1-d]-as-tetrazine-8-carboxamide (U.S. Pat. No. 5,260,291, CAS No. 85622-93-1), and has the structure:

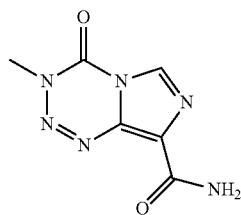

Tamoxifen (CAS Reg. No. 10540-29-1, NOLVADEX®, ISTUBAL®, VALODEX®) is an orally active, selective estrogen receptor modulator (SERM) which is used in the treatment of breast cancer and is currently the world's largest selling drug for this indication. Tamoxifen (Nolvadex®) was first approved by the FDA (ICI Pharmaceuticals, now Astra-Zeneca) in 1977 for treatment of metastatic breast cancer (Jordan V C (2006) Br J Pharmacol 147 (Suppl 1): S269-76). Tamoxifen is currently used for the treatment of both early and advanced estrogen receptor (ER) positive breast cancer in pre- and post-menopausal women (Jordan V C (1993) Br J Pharmacol 110 (2): 507-17). It is also approved by the FDA for the prevention of breast cancer in women at high risk of developing the disease and for the reduction of contralateral (in the opposite breast) breast cancer. Tamoxifen is named as (Z)-2-[4-(1,2-diphenylbut-1-enyl)phenoxy]-N,N-dimethyl-ethanamine, (CAS Reg. No. 10540-29-1) and has the structure:

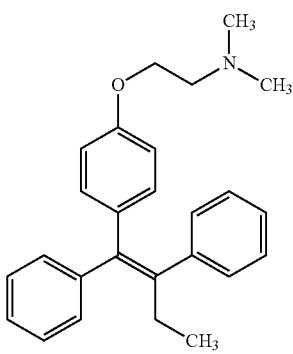 [SMILES: CC/C(=C(\c1ccccc1)c1ccc(OCCN(C)C)cc1)c1ccccc1]

Rapamycin (CAS Reg. No. 53123-88-9, sirolimus, RAPA-MUNE®) is an immunosuppressant drug used to prevent rejection in organ transplantation, and is especially useful in kidney transplants. Rapamycin is a macrolide antibiotic ("-mycin") first discovered as a product of the bacterium *Streptomyces hygroscopicus* in a soil sample from an island called Rapa Nui, better known as Easter Island (Pritchard D I (2005). Drug Discovery Today 10 (10): 688-691). Rapamycin inhibits the response to interleukin-2 (IL-2) and thereby blocks activation of T- and B-cells. The mode of action of rapamycin is to bind the cytosolic protein FK-binding protein 12 (FKBP12). The rapamycin-FKBP12 complex inhibits the mammalian target of rapamycin (mTOR) pathway through directly binding the mTOR Complex1 (mTORC1). mTOR is also called FRAP (FKBP-rapamycin associated protein) or RAFT (rapamycin and FKBP target). Rapamycin is named as (3S,6R,7E,9R,10R,12R,14S,15E,17E,19E,21S,23S,26R, 27R,34aS)-9,10,12,13,14,21,22,23,24,25,26,27,32,33,34, 34a-hexadecahydro-9,27-dihydroxy-3-[(1R)-2-[(1S,3R, 4R)-4-hydroxy-3-methoxycyclohexyl]-1-methylethyl]-10, 21-dimethoxy-6,8,12,14,20,26-hexamethyl-23,27-epoxy-3H-pyrido[2,1-c][1,4]-oxaazacyclohentriacontine-1,5,11, 28,29(4H,6H,31H)-pentone (CAS Reg. No. 53123-88-9), and has the structure:

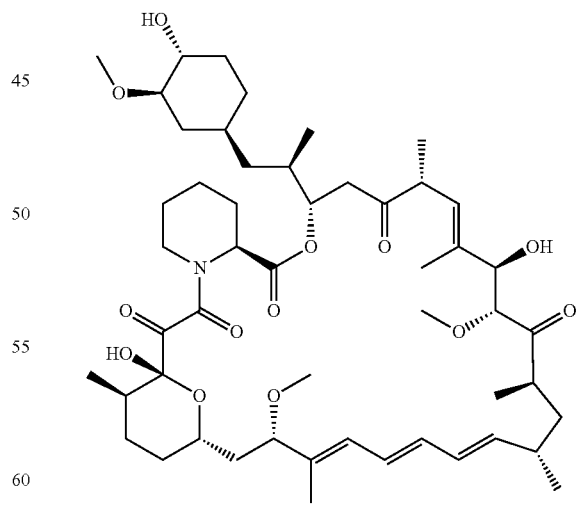

Lapatinib (CAS Reg. No. 388082-78-8, TYKERB®, GW572016, Glaxo SmithKline) has been approved for use in combination with capecitabine (XELODA®, Roche) for the treatment of patients with advanced or metastatic breast cancer whose tumors over-express HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. No. 6,727,256; U.S. Pat. No. 6,713,485; U.S. Pat. No. 7,109,333; U.S. Pat. No. 6,933,299; U.S. Pat. No. 7,084,147; U.S. Pat. No. 7,157,466; U.S. Pat. No. 7,141,576) which inhibits receptor autophosphorylation and activation by binding to the ATP-binding pocket of the EGFR/HER2 protein kinase domain. Lapatinib is named as N-(3-chloro-4-(3-fluorobenzyloxy)phenyl)-6-(5-((2-(methylsulfonyl)ethylamino)methyl)furan-2-yl)quinazolin-4-amine, and has the structure:

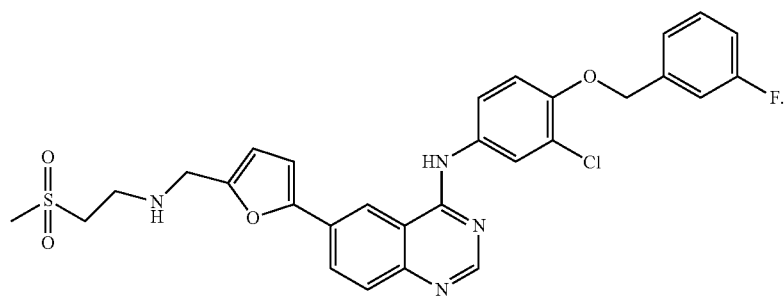 [SMILES: CS(=O)(=O)CCNCc1ccc(-c2ccc3ncnc(Nc4ccc(OCc5cccc(F)c5)c(Cl)c4)c3c2)o1]

Vemurafenib (RG7204, PLX-4032, CAS Reg. No. 1029872-55-5) has been shown to cause programmed cell death in various cancer call lines, for example melanoma cell lines. Vemurafenib interrupts the B-Raf/MEK step on the B-Raf/MEK/ERK pathway—if the B-Raf has the common V600E mutation. Vemurafenib works in patients, for example in melanoma patients as approved by the FDA, whose cancer has a V600E BRAF mutation (that is, at amino acid position number 600 on the B-RAF protein, the normal valine is replaced by glutamic acid). About 60% of melanomas have the V600E BRAF mutation. The V600E mutation is present in a variety of other cancers, including lymphoma, colon cancer, melanoma, thyroid cancer and lung cancer. Vemurafenib has the following structure:

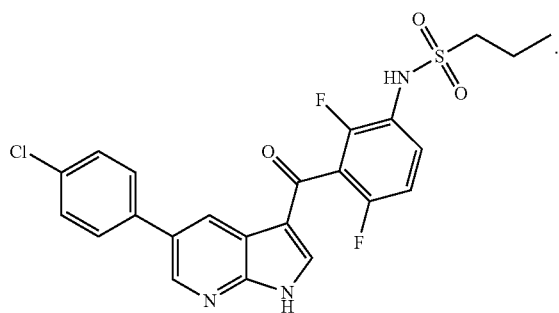 [SMILES: CCCS(=O)(=O)Nc1ccc(F)c(C(=O)c2c[nH]c3ncc(-c4ccc(Cl)cc4)cc23)c1F]

ZELBORAF® (vemurafenib) (Genentech, Inc.) is a drug product approved in the U.S. and indicated for treatment of patients with unresectable or metastatic melanoma with BRAF V600E mutation as detected by an FDA-approved test. ZELBORAF® (vemurafenib) is not recommended for use in melanoma patients who lack the BRAF V600E mutation (wild-type BRAF melanoma).

MDV3100 (CAS Reg. No. 915087-33-1) is an androgen receptor antagonist drug developed for the treatment of hormone-refractory prostate cancer. Up to an 89% decrease in prostate specific antigen serum levels has been reported after a month of taking the medicine. As opposed to bicalutamide, MDV3100 does not promote translocation of AR to the nucleus and in addition prevents binding of AR to DNA and AR to coactivator proteins. MDV 3100 was found clinically active for metastatic castration-resistant prostate cancer patients in ongoing phase I and II trials. MDV3100 has the name 4-(3-(4-cyano-3-(trifluoromethyl)phenyl)-5,5-dimethyl-4-oxo-2-thioxoimidazolidin-1-yl)-2-fluoro-N-methylbenzamide.

Abiraterone (CAS Reg. No. 154229-19-3; see U.S. Pat. Nos. 5,604,213 and 5,618,807) is a drug currently under investigation for use in castration-resistant prostate cancer. It blocks the formation of testosterone by inhibiting CYP17A1 (CYP450c17), an enzyme also known as 17α-hydroxylase/17,20 lyase. This enzyme is involved in the formation of DHEA and androstenedione, which may ultimately be metabolized into testosterone. Abiraterone has the name (3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-ol. It may also be administered as the acetate prodrug (3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl acetate.

ZYTIGA® (abiraterone acetate) (JOHNSON & JOHNSON Corp) is a drug product approved in the U.S. and indicated for use in combination with prednisone for the treatment of patients with metastatic castration-resistant prostate cancer who have received prior chemotherapy containing docetaxel.

GDC-0973 is a selective inhibitor of MEK, also known as mitogen activated protein kinase kinase (MAPKK), which is a key component of the RAS/RAF/MEK/ERK pathway that is frequently activated in human tumors. Inappropriate activation of the MEK/ERK pathway promotes cell growth in the absence of exogenous growth factors. A Phase I clinical trial evaluating GDC-0973 for solid tumors is ongoing. GDC-0973 can be prepared as described in International Patent Application Publication Number WO2007044515(A1). GDC-0973 has the name: (S)-(3,4-difluoro-2-(2-fluoro-4-iodophenylamino)phenyl)(3-hydroxy-3-(piperidin-2-yl)azetidin-1-yl)methanone, and the following structure:

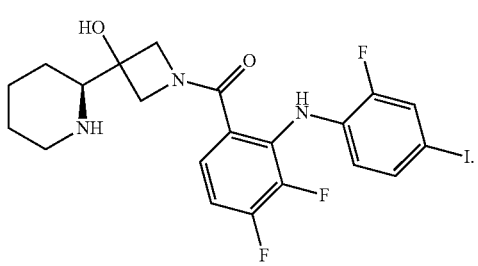 [SMILES: O=C(c1ccc(F)c(F)c1Nc1ccc(I)cc1F)N1CC(O)([C@@H]2CCCCN2)C1]

Pharmaceutical Compositions

Pharmaceutical compositions or formulations of the present invention include combinations of Formula I compounds, a chemotherapeutic agent, and one or more pharmaceutically acceptable carrier, glidant, diluent, or excipient.

One example includes a first formulation for oral delivery of a compound of formula I, or a salt thereof, and one or more pharmaceutically acceptable carrier, glidant, diluent, or excipient, and a second formulation for oral delivery of vemerafenib, or a salt thereof, and one or more pharmaceutically acceptable carrier, glidant, diluent, or excipient. In one example, the first formulation comprises GDC-0068 or a salt thereof.

The Formula I compounds, and chemotherapeutic agents of the present invention may exist in unsolvated as well as solvated forms with pharmaceutically acceptable solvents such as water, ethanol, and the like, and it is intended that the invention embrace both solvated and unsolvated forms.

The Formula I compounds, and chemotherapeutic agents of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including a Formula I compound and a chemotherapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium ($^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Formula I compounds and chemotherapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising a Formula I compound in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a Formula I compound having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered orally or parenterally per dose will be in the range of about 0.01-1000 mg/kg, namely about 0.1 to 20 mg/kg of patient body weight per day, with, in one example, the typical initial range of compound used being 0.3 to 15 mg/kg/day. The dose of the Formula I compound and the dose of the chemotherapeutic agent to be administered may range for each from about 1 mg to about 1000 mg per unit dosage form, or, in one example, from about 10 mg to about 100 mg per unit dosage form, and in another example from about 100 to about 1000 mg. The doses of Formula I compound and the chemotherapeutic agent may administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I and/or chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound of Formula I and/or a chemotherapeutic agent. The amount of compound of Formula I and the amount of chemotherapeutic agent may be formulated in a pill, capsule, solution or suspension as a combined formulation. Alternatively, the Formula I compound and the chemotherapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation include Tween® 60, Span® 80, cetostearyl alcohol, benzyl alcohol, myristyl alcohol, glyceryl monostearate and sodium lauryl sulfate.

Aqueous suspensions of the pharmaceutical formulations contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compound of formula I or a pharmaceutically acceptable salt thereof may be employed in combination with other chemotherapeutic agents or a pharmaceutically acceptable salt thereof for the treatment of a hyperproliferative disease or disorder, including tumors, cancers, and neoplastic tissue, along with pre-malignant and non-neoplastic or non-malignant hyperproliferative disorders. In certain embodiments, a compound of Formula I or a pharmaceutically acceptable salt thereof is combined in a dosing regimen as combination therapy, with a second compound or a pharmaceutically acceptable salt thereof that has anti-hyperproliferative properties or that is useful for treating the hyperproliferative disorder. The second compound of the dosing regimen preferably has complementary activities to the compound of formula I or a pharmaceutically acceptable salt thereof, and such that they do not adversely affect each other. Such compounds may be administered in amounts that are effective for the purpose intended. In one embodiment, the therapeutic combination is administered by a dosing regimen wherein the therapeutically effective amount of a compound of formula I, or a pharmaceutically acceptable salt thereof is administered in a range from twice daily to once every three weeks (q3wk), and the therapeutically effective amount of the chemotherapeutic agent is administered in a range from twice daily to once every three weeks.

The combination therapy may be administered as a simultaneous or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities.

In one specific aspect of the invention, the compound of formula I or the pharmaceutically acceptable salt thereof can be administered for a time period of about 1 to about 10 days after administration of the one or more agents begins. In another specific aspect of the invention, the compound of formula I or the pharmaceutically acceptable salt thereof can be administered for a time period of about 1 to 10 days before administration of the combination begins. In another specific aspect of the invention, administration of the compound of formula I or the pharmaceutically acceptable salt thereof and administration of the chemotherapeutic agent begin on the same day.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, a compound of formula I, or pharmaceutically acceptable salt thereof, may be combined with a chemotherapeutic agent, as well as combined with surgical therapy and radiotherapy. The amounts of the compound of formula I or a pharmaceutically acceptable salt thereof and the other pharmaceutically active chemotherapeutic agent(s) and the relative timings of administration will be selected in order to achieve the desired combined therapeutic effect.

Administration of Pharmaceutical Compositions

The compounds may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices.

Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 20 mg to about 1600 mg per day of the compound of formula I or a pharmaceutically acceptable salt thereof. A typical dose may be about 50 mg to about 800 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

Therapeutic combinations of: (1) a compound of formula I or a pharmaceutically acceptable salt thereof, and (2) a chemotherapeutic agent or a pharmaceutically acceptable salt thereof are useful for treating diseases, conditions and/or disorders including, but not limited to, those modulated by AKT kinase in a mammal. In one example, cancers which can be treated according to the methods of this invention include, but are not limited to, mesothelioma, endometrial, breast, lung, ovarian, prostate (including castration resistant prostace cancer "CRPC"), pancreatic, melanoma, gastric, colon, glioma, head and neck.

Therapeutic combinations of: (1) a compound of formula I or a pharmaceutically acceptable salt thereof, and (2) a chemotherapeutic agent or a pharmaceutically acceptable salt thereof are useful for treating diseases, conditions and/or disorders including, but not limited to, those modulated by BRAF kinase comprising the V600E mutation, and in one example further modulated by high pAKT expression or activation levels, in a mammal. Cancers which can be treated according to the methods of this invention include, but are not limited to, lymphoma (including non-Hodgkin's lymphoma), colon cancer, metastatic melanoma, thyroid cancer (including papillary thyroid carcinoma) or lung cancer (including non-small cell lung cancer). In one example, the cancer to be treated is unresectable or metastatic melanoma.

Kits for testing whether a patient comprises the BRAF V600E mutation are commercially available. One example is the COBAS® 4800 BRAF V600 Mutation Test (Roche Molecular Systems Inc.), which detects the BRAF V600E mutation in formalin-fixed, paraffin-embedded (FFPET) human melanoma tissue. It is approved in the U.S. as a companion diagnostic for treatment with vemurafenib or a pharmaceutically acceptable salt thereof, designed to treat patients whose melanoma tumors harbor the mutated form of the BRAF gene. In pre-clinical and clinical investigations, the Cobas® BRAF Mutation Test had 97.3% positive agreement in detecting the BRAF V600E (1799 T>A) mutation, which represents >~85% of all BRAF mutations reported in the COSMIC database.

In formalin-fixed, paraffin-embedded tissue (FFPET), the Cobas® BRAF Mutation Test can detect V600E mutations at >5% mutation level. The test may also detect other V600 mutations such as V600D and V600K. The Cobas® BRAF Mutation Test can be performed in <8 hours from receipt of specimen, such as tissue sample or tumor cells obtained from the patient. The Cobas® 4800 BRAF V600 Mutation Test is a real-time PCR test on the Cobas® 4800 System, v2.0, and is intended to be used as an aid in selecting melanoma patients whose tumors carry the BRAF V600E mutation for treatment with vemurafenib, and in certain embodiment, vemurafenib in combination with a compound of formula I or a salt thereof, such as GDC-0068.

One aspect includes a method of tumor growth inhibition (TGI) in a patient suffering from a cancer comprising a BRAF V600E mutation, and in one example further comprising high pAKT expression or activation levels, comprising administering GDC-0068 or a pharmaceutically acceptable salt thereof and vemurafenib or a pharmaceutically acceptable salt thereof to the patient. In certain embodiments, the combination is synergistic. In certain embodiments, the TGI of the combination is greater than the TGI of either GDC-0068 or vemurafenib alone. In certain embodiments, the TGI of the combination is about 10, 15, 20, 25, 30, 35, 40, 45, 50, 55, 60, 65, 70 or 75 percent greater than the TGI of either GDC-0068 or vemurafenib alone.

Methods of measuring TGI are known in the art. In one example method, average tumor volumes are determined and compared from the patient before and after treatment. Tumor volumes can be measured in two dimensions (length and width) using any method in the art, for example UltraCal IV calipers (Fred V. Fowler Company) or by PET (positron emission tomography), or by some other method. The formula tumor volume $(mm^3)=(length \times width^2) \times 0.5$ can be used. Measuring tumor volumes over multiple time periods can be done using a mixed-modeling Linear Mixed Effects (LME) approach (Pinheiro et al. 2009). This approach can address both repeated measurements (and multiple patients). Cubic regression splines can be used to fit a non-linear profile to the time courses of tumor volume at each dose level. These non-linear profiles can then be related to dose within the mixed model. Tumor growth inhibition as a percent of vehicle can be calculated as a percent area under the fitted curve (AUC) per day in relation to the vehicle, using the following formula:

$$\% \ TGI = 100 \left[ 1 - \left( \frac{AUC_{treatment}/\text{day}}{AUC_{vehicle}/\text{day}} \right) \right]$$

Using this formula, a TGI value of 100% indicates tumor stasis, greater than about 1% but less than about 100% indicates tumor growth inhibition, and greater than about 100% indicates tumor regression.

In certain embodiments, the patient being treated with the combination has been treated previously with vemurafenib or a pharmaceutically acceptable salt thereof. In certain embodiments, the patient has been previously treated with vemurafenib and has developed resistance to vemurafenib. In certain embodiments, the cancer has regressed or returned during or after single agent vemurafenib treatment. In certain embodiments, the cancer comprises a BRAF V600E mutation but has become resistant to the vemurafenib treatment and further comprises high pAKT expression or activation levels. In certain embodiments, the combination treatment of a compound of formula I or a pharmaceutically acceptable salt thereof and vemurafenib and a pharmaceutically acceptable salt thereof act to overcome vemurafenib resistance and treat the regressed cancer. In certain embodiments, the cancer is vemurafenib resistant cancer, for example, vemurafenib resistant lymphoma (including non-Hodgkin's lymphoma), colon cancer, metastatic melanoma, thyroid cancer (including papillary thyroid carcinoma) or lung cancer (including non-small cell lung cancer). In one example, the cancer to be treated is vemurafenib resistant unresectable or metastatic melanoma. In certain embodiments, the patient has previously received, and in one example failed or regressed from, vemurafenib single agent therapy before being treated with the combinations described herein (e.g., GDC-0068 or a salt thereof plus vemurafenib or a salt thereof).

In certain embodiments, the cancer comprises BRAF V600E mutation and one of AKT, PI3k or PTEN mutations or AKT, PI3k or PTEN abberant signaling. In one example, the patient or tumor to be treated comprises BRAF V600E mutation and high pAKT levels.

One aspect includes the use of a compound of formula I or a pharmaceutically acceptable salt thereof in combination with vemurafenib or a pharmaceutically acceptable salt thereof in therapy. In one embodiment, the therapy is of a hyperproliferative disease including those mediated by the BRAF V600E, AKT, PTEN or PI3k mutations, which include, but are not limited to, lymphoma (including non-Hodgkin's lymphoma), colon cancer, metastatic melanoma, thyroid cancer (including papillary thyroid carcinoma) or lung cancer (including non-small cell lung cancer). In one example, the cancer to be treated is unresectable or metastatic melanoma.

One aspect includes the use of a compound of formula I or a pharmaceutically acceptable salt thereof in combination with vemurafenib or a pharmaceutically acceptable salt thereof in the manufacture of a medicament. In one embodiment, the medicament is for treatment of a hyperproliferative disease including those mediated by the BRAF V600E, AKT, PTEN or PI3k mutations, which include, but are not limited to, lymphoma (including non-Hodgkin's lymphoma), colon cancer, metastatic melanoma, thyroid cancer (including papillary thyroid carcinoma) or lung cancer (including non-small cell lung cancer). In one example, the cancer to be treated is unresectable or metastatic melanoma. In certain embodiments, the medicament is for treating a patient who has previously received, and in one example failed or regressed from, vemurafenib single agent therapy.

Articles of Manufacture

In another embodiment of the invention, an article of manufacture, or "kit", containing a compound of formula I or pharmaceutically acceptable salt thereof useful for the treatment of the diseases and disorders described above is provided. In one embodiment, the kit comprises a container and a compound of formula I or pharmaceutically acceptable salt thereof.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or pharmaceutically acceptable salt thereof, or a formulation thereof which is effective for treating the condition and may have a sterile access port (for example, the container may be an intravenous solution bag or a vial having a stopper pierceable by a hypodermic injection needle). At least one active agent in the composition is a compound of formula I or a pharmaceutically acceptable salt thereof. The label or package insert indicates that the composition is used for treating the condition of choice, such as cancer. In one embodiment, the label or package inserts indicates that the composition comprising a compound of formula I or pharmaceutically acceptable salt thereof can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of a compound of formula I or pharmaceutically acceptable salt thereof, and, if present, the second pharmaceutical formulation. For example, if the kit comprises a first composition comprising a compound of formula I or pharmaceutically acceptable salt thereof and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of formula I or pharmaceutically acceptable salt thereof, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of formula I or pharmaceutically acceptable salt thereof contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of a compound of formula I or pharmaceutically acceptable salt thereof and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Specific Aspects of the Invention

In one specific aspect of the invention the hyperproliferative disorder is cancer. In another specific aspect, the cancer is metastatic melanoma.

In one specific aspect of the invention the cancer is associated with PTEN mutation.

In one specific aspect of the invention the cancer is associated with PTEN low or null status.

In one specific aspect of the invention the cancer is associated with AKT mutation, overexpression or amplification.

In one specific aspect of the invention the cancer is associated with high pAKT expression or activation levels.

In one specific aspect of the invention the cancer is associated with PI3K mutation.

In one specific aspect of the invention the cancer is selected from, breast, lung, ovarian, prostate (e.g., castration resistant prostate cancer), melanoma, gastric, colon, renal, head and neck, and giloma.

In one specific aspect of the invention the compound of formula I or a pharmaceutically acceptable salt thereof and 5-FU are administered to the mammal.

In one specific aspect of the invention the compound of formula I or a pharmaceutically acceptable salt thereof, 5-FU, and oxaliplatin are administered to the mammal and the cancer is gastric, ovarian, or colon.

In one specific aspect of the invention the compound of formula I or a pharmaceutically acceptable salt thereof, 5-FU, and oxaliplatin are administered to the mammal and the cancer is gastric, prostate, head or neck.

In one specific aspect of the invention the compound of formula I or a pharmaceutically acceptable salt thereof, 5-FU, oxaliplatin, and folinic acid are administered to the mammal and the cancer is gastric, ovarian, or colon.

In one specific aspect of the invention the compound of formula I or a pharmaceutically acceptable salt thereof, 5-FU, oxaliplatin, and folinic acid are administered to the mammal and the cancer is gastric, prostate, head or neck.

In one specific aspect of the invention the compound of formula I or a pharmaceutically acceptable salt thereof, 5-FU, oxaliplatin, and folinic acid are administered to the mammal and the cancer is gastric, prostate, head or neck, and the mammal has PTEN low or null status, a PI3k mutation, a AKT mutation or high pAKT.

In one specific aspect of the invention the compound of formula I or a pharmaceutically acceptable salt thereof and carboplatin are administered to the mammal.

In one specific aspect of the invention the compound of formula I or a pharmaceutically acceptable salt thereof and carboplatin are administered to the mammal and the cancer is breast, lung, or prostate.

In one specific aspect of the invention the compound of formula I or a pharmaceutically acceptable salt thereof and carboplatin are administered to the mammal and the cancer is breast, lung, prostate, head or neck.

In one specific aspect of the invention the compound of formula I or a pharmaceutically acceptable salt thereof and irinotecan are administered to the mammal.

In one specific aspect of the invention the compound of formula I or a pharmaceutically acceptable salt thereof and irinotecan are administered to the mammal and the cancer is colon.

In one specific aspect of the invention the compound of formula I or a pharmaceutically acceptable salt thereof docetaxel are administered to the mammal.

In one specific aspect of the invention the compound of formula I or a pharmaceutically acceptable salt thereof and docetaxel are administered to the mammal and the cancer is breast, giloma, lung, melanoma, ovarian, or prostate.

In one specific aspect of the invention the compound of formula I or a pharmaceutically acceptable salt thereof and docetaxel are administered to the mammal and the cancer is breast, ovarian, or prostate.

In one specific aspect of the invention the compound of formula I or a pharmaceutically acceptable salt thereof and doxorubicin are administered to the mammal.

In one specific aspect of the invention the compound of formula I or a pharmaceutically acceptable salt thereof and doxorubicin are administered to the mammal and the cancer is breast, lung, ovarian, giloma, or prostate.

In one specific aspect of the invention the compound of formula I or a pharmaceutically acceptable salt thereof and SN-38 are administered to the mammal.

In one specific aspect of the invention the compound of formula I or a pharmaceutically acceptable salt thereof and SN-38 are administered to the mammal and the cancer is colon.

In one specific aspect of the invention the compound of formula I or a pharmaceutically acceptable salt thereof and temozolomide are administered to the mammal.

In one specific aspect of the invention the compound of formula I or a pharmaceutically acceptable salt thereof and temozolomide are administered to the mammal and the cancer is giloma.

In one specific aspect of the invention the compound of formula I or a pharmaceutically acceptable salt thereof and a platinum agent are administered to the mammal.

In one specific aspect of the invention the compound of formula I or a pharmaceutically acceptable salt thereof and a platinum agent are administered to the mammal and the cancer is ovarian.

In one specific aspect of the invention the compound of formula I or a pharmaceutically acceptable salt thereof and GDC-0973 or a pharmaceutically acceptable salt thereof are administered to the mammal.

In one specific aspect of the invention the compound of formula I or a pharmaceutically acceptable salt thereof and GDC-0973 or a pharmaceutically acceptable salt thereof are administered to the mammal and the cancer is pancreatic, prostate, melanoma or breast.

In one specific aspect of the invention the compound of formula I or a pharmaceutically acceptable salt thereof and vemurafenib or a pharmaceutically acceptable salt thereof are administered to the mammal.

In one specific aspect of the invention the compound of formula I or a pharmaceutically acceptable salt thereof and vemurafenib or a pharmaceutically acceptable salt thereof are administered to the mammal and the cancer is melanoma.

In one specific aspect of the invention the compound of formula I or a pharmaceutically acceptable salt thereof and vemurafenib or a pharmaceutically acceptable salt thereof are administered to the mammal and the cancer is melanoma, and the mammal comprises BRAF V600E mutation and high pAKT expression or activation levels.

In one specific aspect of the GDC-0068 or a pharmaceutically acceptable salt thereof and vemurafenib or a pharmaceutically acceptable salt thereof are administered to the mammal and the cancer is melanoma, and the mammal comprises BRAF V600E mutation and high pAKT expression or activation levels.

In one specific aspect of the GDC-0068 or a pharmaceutically acceptable salt thereof and vemurafenib or a pharmaceutically acceptable salt thereof are administered to the mammal and the cancer is melanoma, wherein the mammal comprises BRAF V600E mutation and is resistant to vemurafenib single agent therapy.

In one specific aspect of the invention the compound of formula I or a pharmaceutically acceptable salt thereof is administered orally.

In one specific aspect of the invention the compound of formula I or a pharmaceutically acceptable salt thereof is formulated as a tablet.

General Preparative Procedures

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other AKT inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1

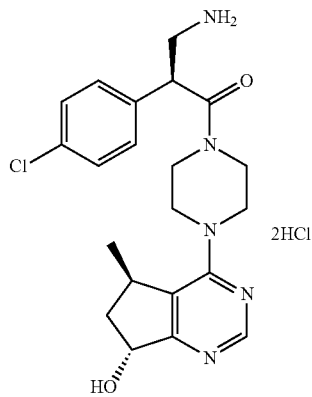 [SMILES: C[C@@H]1C[C@@H](O)c2ncnc(N3CCN(C(=O)[C@H](CN)c4ccc(Cl)cc4)CC3)c21]

Preparation of (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one dihydrochloride Step 1: To a 1 L round-bottom flask were added (R)-(+)-Pulegone (76.12 g, 0.5 mmol), anhydrous NaHCO$_3$ (12.5 g) and anhydrous ether (500 mL) The reaction mixture was cooled with ice-bath under nitrogen. The bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight and then 1 L of 5% HCl and 300 mL of ether were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL), and then boiling ethanol (300 mL) was added to give a clear solution. The mixture was refluxed for 2.5 hours and then stirred at room temperature overnight. The mixture was treated with 1 L of water and 300 mL of ether. The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene) cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 2: (2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft$^3$h$^{-1}$ of O$_2$) was bubbled through the solution for 3.5 hours. The reaction mixture was flushed with nitrogen at room temperature until the color disappeared. The ethyl acetate was removed under vacuum and the residue was dissolved in 150 mL of acetic acid and cooled by ice water, and zinc powder (45 g) was added. The solution was stirred for 30 minutes and then filtered. The filtrate was neutralized with 2N NaOH (1.3 L) and NaHCO$_3$. The aqueous phase was extracted with ether (3×200 mL). The organic phase was combined, washed with water, dried and concentrated to afford (2R)-ethyl 2-methyl-5-oxocyclopentanecarboxylate (20 g, 96%). $^1$H NMR (CDCl$_3$, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 3: To a solution of a mixture of (2R)-ethyl 2-methyl-5-oxocyclopentanecarboxylate (20 g, 117.5 mmol) and thiourea (9.2 g, 120.9 mmol) in ethanol (100 mL) was added KOH (8.3 g, 147.9 mmol) in water (60 mL). The mixture was refluxed for 10 hours. After cooling, the solvent was removed and the residue was neutralized with concentrated HCl (12 mL) at 0° C. and then extracted with DCM (3×150 mL) The solvent was removed and the residue was purified by silica gel chromatography, eluting with Hexane/ethyl acetate (2:1) to give (R)-2-mercapto-5-methyl-6,7-dihydro-5H-cyclopenta [d]pyrimidin-4-ol (12 g, 56%). MS (APCI+) [M+H]+183.

Step 4: To a suspension of (R)-2-mercapto-5-methyl-6,7-dihydro-5H-cyclopenta[d]pyrimidin-4-ol (12 g, 65.8 mmol) in distilled water (100 mL) was added Raney Nickel (15 g) and NH4OH (20 mL). The mixture was refluxed for 3 hours then filtered, and the filtrate was concentrated to afford (R)-5-methyl-6,7-dihydro-5H-cyclopenta[d]pyrimidin-4-ol (9.89 g, 99%). MS (APCI+) [M+H]+151.

Step 5: A mixture of (R)-5-methyl-6,7-dihydro-5H-cyclopenta[d]pyrimidin-4-ol (5.8 g, 38.62 mmol) in POCl3 (20 mL) was refluxed for 5 minutes. Excess POCl3 was removed under vacuum and the residue was dissolved in DCM (50 mL). The mixture was then added to saturated NaHCO3 (200 mL). The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). 1H NMR (CDCl3, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 6: To a solution of (R)-4-chloro-5-methyl-6,7-dihydro-5H-cyclopenta[d]pyrimidine (2.5 g, 14.8 mmol) in CHCl3 (60 mL) was added MCPBA (8.30 g, 37.0 mmol) in three portions. The mixture was stirred at room temperature for 2 days. The mixture was cooled to 0° C. and to this was added dropwise Na2S2O3 (10 g) in water (60 mL), followed by Na2CO3 (6 g) in water (20 mL). The reaction mixture was stirred for 20 minutes. The aqueous phase was extracted with CHCl3 (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). 1H NMR (CDCl3, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 7: A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). 1H NMR (CDCl3, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H]+227.

Step 8: To a solution of (5R)-4-chloro-5-methyl-6,7-dihydro-5H-cyclopenta[d]pyrimidin-7-yl acetate (0.5 g, 2.2 mmol) in NMP (10 mL) was added 1-Boc-piperazine (0.9 g, 4.8 mmol). The reaction mixture was heated to 110° C. for 12 hours. After cooling, the reaction mixture was diluted with ethyl acetate (200 mL) and washed with water (6×100 mL). The organic phase was dried and concentrated. The residue was purified by silica gel chromatography, eluting with ethyl acetate to give tert-butyl 4-((5R)-7-acetoxy-5-methyl-6,7-dihydro-5H-cyclopenta[d]pyrimidin-4-yl)piperazine-1-carboxylate (0.6 g, 72%). 1H NMR (CDCl3, 400 MHz) δ 8.60 (d, 1H), 6.05-5.90 (m, 1H), 3.80-3.30 (m, 9H), 2.84 (m, 1H), 2.20-(m, 1H), 1.49 (s, 9H), 1.29-1.20 (m, 3H). MS (APCI+) [M+H]+377. The resulting mixture of the diastereomers was purified by chiral separation HPLC (Chiralcel ODH column, 250×20 mm, Hexane/EtOH 60:40, 21 mL/min). The first peak (RT=3.73 min) gave the tert-butyl 4-((5R,7R)-7-acetoxy-5-methyl-6,7-dihydro-5H-cyclopenta[d]pyrimidin-4-yl)piperazine-1-carboxylate (0.144 g, 24%). The second peak (RT=5.66 min) gave the tert-butyl 4-((5R,7S)-7-acetoxy-5-methyl-6,7-dihydro-5H-cyclopenta[d]pyrimidin-4-yl)piperazine-1-carboxylate (0.172 g, 29%). MS (APCI+) [M+H]+ 377.

Step 9: To a solution of tert-butyl 4-((5R,7R)-7-acetoxy-5-methyl-6,7-dihydro-5H-cyclopenta[d]pyrimidin-4-yl)piperazine-1-carboxylate (0.144 g, 0.383 mmol) in THF (4 mL) was added LiOH (3M, 2 mL). The mixture was stirred at room temperature for 6 hours and then quenched with 2N HCl (3 mL) The solvent was removed and the residue was purified by silica gel chromatography, eluting with ethyl acetate to give tert-butyl 4-((5R,7R)-7-hydroxy-5-methyl-6,7-dihydro-5H-cyclopenta[d]pyrimidin-4-yl)piperazine-1-carboxylate (89 mg, 70%). %). 1H NMR (CDCl3, 400 MHz) δ 8.52 (s, 1H), 5.48 (br, 1H), 5.14 (m, 1H), 3.82-3.40 (m, 9H), 2.20 (m, 2H), 1.49 (s, 9H), 1.19 (d, J=6.8 Hz, 3H). MS (APCI+) [M+H]+ 335.

Step 10: tert-Butyl 4-((5R,7R)-7-hydroxy-5-methyl-6,7-dihydro-5H-cyclopenta[d]pyrimidin-4-yl)piperazine-1-carboxylate was treated with HCl (4M in dioxane, 2 mL) in DCM (5 mL) for 6 hours to give (5R,7R)-5-methyl-4-(piperazin-1-yl)-6,7-dihydro-5H-cyclopenta[d]pyrimidin-7-ol dihydrochloride. MS (APCI+) [M+H]+235.

Step 11: Tert-butyl 2,4-dimethoxybenzylcarbamate (3.96 g, 14.8 mmol) was dissolved in THF (74 mL) and cooled to −78° C. The solution was treated with butyl lithium (7.44 mL, 16.3 mmol) dropwise over a five minute period to afford a pale-yellow solution. The solution was allowed to stir for 15 minutes before the chloro(methoxy)methane (1.35 mL, 17.8 mmol) was added dropwise (neat). The reaction was stirred at −78° C. for 10 minutes, then allowed to warm slowly to ambient temperature overnight. The reaction was concentrated in vacuo to afford a yellow gel which was partitioned between half-saturated NH4Cl solution and ether. The aqueous layer was extracted once, and the organics were combined. The organic layer was washed with water, then brine, separated, dried over Na2SO4, filtered, and concentrated in vacuo. 1H NMR supports the desired near-pure (>90%) tert-butyl 2,4-dimethoxybenzyl(methoxymethyl)carbamate (4.81 g, 104% yield) as a pale-yellow oil which was used without purification.

Step 12: (R)-4-benzyl-3-(2-(4-chlorophenyl)acetyl)oxazolidin-2-one (3.00 g, 9.10 mmol) was dissolved in DCM (91 mL) and cooled to −78° C. A 1M toluene solution of TiCl4 (11.4 mL, 11.4 mmol) was added to the solution followed by DIEA (1.66 mL, 9.55 mmol) to afford a dark purple reaction. This was allowed to stir for 15 minutes before the tert-butyl 2,4-dimethoxybenzyl(methoxymethyl)carbamate (3.40 g, 10.9 mmol) was added as a solution in DCM (10 mL) dropwise. The reaction was allowed to stir for 15 minutes at −78° C., then allowed to warm to −18° C. in a brine-ice bath for one hour. This reaction was allowed to warm slowly to 0° C. over a 2.5 hour period. The reaction was then quenched with the addition of saturated NH4Cl solution (100 mL). The layers were separated, and the organic layers was extracted once with DCM. The combined organic layers were dried over MgSO4, filtered, and concentrated in vacuo to afford a yellow oil. The residue was purified by chromatography (silica gel eluted with 4:1 hexanes:ethyl acetate) to afford the pure material as a colorless oil tert-butyl 2,4-dimethoxybenzyl((S)-3-((R)-4-benzyl-2-oxooxazolidin-3-yl)-2-(4-chlorophenyl)-3-oxopropyl)carbamate (4.07 g, 73.5% yield). This tert-butyl 2,4-dimethoxybenzyl(S)-3-((R)-4-benzyl-2-oxooxazolidin-3-yl)-2-(4-chlorophenyl)-3-oxopropyl)carbamate (680 mg, 1.12 mmol) was dissolved in DCM (10.6 mL) and water (560 uL; 19:1 DCM:water) at ambient temperature. The solution was treated with DDQ (380 mg, 1.67 mmol), and the reaction was allowed to stir for one day to afford reaction completion by TLC and LCMS analysis. The reaction was diluted with DCM and washed twice with half saturated NaHCO3 solution. The organic layer was dried over MgSO4, filtered, and concentrated in vacuo to afford a yellow-orange oil. The residue was purified by chromatography (silica gel eluted with 9:1 hexanes:ethyl acetate) to afford a mixture of the aldehyde by-product and tert-butyl(S)-3-((R)-4-benzyl-2-oxooxazolidin-3-yl)-2-(4-chlorophenyl)-3-oxopropylcarbamate (not separable) as a pale-yellow oil (729 mg combined mass). LC/MS (APCI+) m/z 359.1 [M-BOC+H]+.

Step 13: 35% H2O2 (0.240 mL, 2.91 mmol) was added to a solution of LiOH—H2O (0.0978 g, 2.33 mmol) in 2:1 THF:H2O (33 mL). The reaction mixture was stirred at room temperature for 35 minutes, and then cooled to 0° C. A solution containing a mixture of tert-butyl(S)-3-((R)-4-benzyl-2-oxooxazolidin-3-yl)-2-(4-chlorophenyl)-3-oxopropylcarbamate (0.535 g, 1.17 mmol) and 2,4-dimethoxybenzaldehyde (0.194 g, 1.17 mmol) in THF (7 mL) was added dropwise by addition funnel. The ice bath was allowed to slowly warm, and the reaction mixture was stirred overnight. The reaction mixture was then cooled to 0° C., and 1M Na2SO3 (7 mL) was added. The mixture was stirred for 5 minutes, and then warmed to room temperature and stirred an additional 20 minutes. The reaction mixture was then transferred to a separatory funnel and washed with ether (3×). The aqueous layer was acidified with KHSO4(s), and the mixture was extracted with DCM (2×). The combined extracts were dried (Na2SO4), filtered, and concentrated to give (S)-3-(tert-butoxycarbonylamino)-2-(4-chlorophenyl)propanoic acid (0.329 g, 94.2% yield) as a white residue. LC/MS (APCI+) m/z 200 [M-BOC+H]+.

Step 14: 4M HCl/dioxane (5.49 ml, 22.0 mmol) was added to a solution of (S)-3-(tert-butoxycarbonylamino)-2-(4-chlorophenyl)propanoic acid (0.329 g, 1.10 mmol) in 2:1 dioxane: DCM (10 mL). The reaction mixture was stirred at room temperature overnight (16 hours), after which it was concentrated to ⅓ volume. The resulting cloudy mixture was diluted with ether, and the mixture was concentrated again to ⅓ volume. The mixture was diluted again with ether (20 mL), and the solids were isolated by filtration through a medium frit funnel with nitrogen pressure, rinsed with ether (5×10 mL), dried under nitrogen pressure, and dried in vacuo to give (S)-3-amino-2-(4-chlorophenyl)propanoic acid hydrochloride (0.199 g, 76.8% yield) as a white powder. HPLC>99 area % pure. LC/MS (APCI+) m/z 200.

Step 15: Boc2O (0.368 g, 1.69 mmol) was added to a solution of (S)-3-amino-2-(4-chlorophenyl)propanoic acid hydrochloride (0.199 g, 0.843 mmol) and tetramethylammonium hydroxide pentahydrate (0.382 g, 2.11 mmol) in 10:1 MeCN:H2O (7.7 mL). The reaction mixture was stirred overnight at room temperature (12 hours), after which the MeCN was removed on a rotary evaporator. The mixture was diluted with water and washed with ether (2×). The aqeuous layer was acidified with KHSO4(s), the mixture was extracted with DCM, and the combined extracts were dried (Na2SO4), filtered, and concentrated to give (S)-3-(tert-butoxycarbonylamino)-2-(4-chlorophenyl)propanoic acid (0.229 g, 90.6% yield) as a foam. HPLC>99 area % pure. LC/MS (APCI+) m/z 200 [M-BOC+H]+.

Step 16: To a solution of (5R,7R)-5-methyl-4-(piperazin-1-yl)-6,7-dihydro-5H-cyclopenta[d]pyrimidin-7-ol dihydrochloride (88 mg, 0.29 mmol) and (S)-3-(tert-butoxycarbonylamino)-2-(4-chlorophenyl)propanoic acid (86 mg, 0.29 mmol) in DCM (10 mL) and Diisopropylethylamine (0.22 mL, 1.3 mmol) was added HBTU (110 mg, 0.29 mmol). The reaction mixture was stirred at room temperature for 1 hour. The solvent was removed and the residue was dissolved in ethyl acetate (100 mL), washed with water (6×50 ml). The organic phase was dried and concentrated to give tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylcarbamate (116 mg, 78%). 1H NMR (CDCl3, 400 MHz) δ 8.51 (s, 1H), 7.34-7.20 (m, 4H), 5.15-5.09 (m, 2H), 4.15-4.05 (m, 1H), 3.87-3.85 (m, 2H), 3.78-3.38 (m, 7H), 3.22-3.19 (m, 1H), 2.20-2.10 (m, 2H), 1.48 (s, 9H), 1.41 (s, 9H), 1.14-1.12 (d, J=7.2 Hz, 3H). MS (APCI+) [M+H]+516.

Step 17: Treatment of tert-butyl(S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylcarbamate with HCl (4M in dioxane, 2 mL) in DCM (5 mL) for 6 hours to give (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one dihydrochloride. 1H NMR (D2O, 400 MHz) δ 8.38 (s, 1H), 7.37-7.35 (d, J=8.4 Hz, 2H), 7.23-7.21 (d, J=8.4 Hz, 2H), 5.29-5.25 (m, 1H), 4.64 (s, 9H), 4.31-4.28 (m, 1H), 4.11 (m, 1H), 3.88-3.79 (m, 2H), 3.70-3.20 (m, 10H), 2.23-2.17 (m, 1H), 2.07-1.99 (m, 1H), 1.22-1.20 (m, 2H), 0.98-0.96 (d, J=6.8 Hz, 2H). MS (APCI+) [M+H]+416.

Example 2

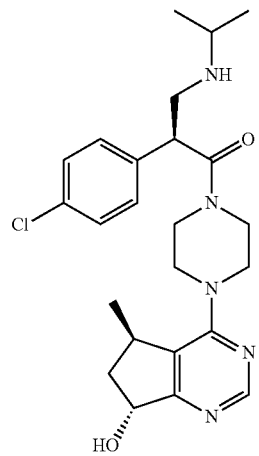 [SMILES: CC(C)NC[C@@H](C(=O)N1CCN(c2ncnc3c2[C@H](C)C[C@H]3O)CC1)c1ccc(Cl)cc1]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one Step 1: Ethyl pulegenate (130 g, 662 mmol) in EtOAc (900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to pH 7 with aqueous NaOH and NaHCO3 and extracted with ether (3×800 mL). The combined organics were dried with brine, MgSO4 and concentrated to give (2R)-ethyl 2-methyl-5-oxo-cyclopentane-carboxylate as a brown liquid (107 g, 95%).

Step 2: Ammonium acetate (240.03 g, 3113.9 mmol) was added to a solution of (R)-ethyl 2-methyl-5-oxocyclopentan-ecarboxylate (106.0 g, 622.78 mmol) in MeOH (1.2 L). The reaction mixture was stirred at room temperature under nitrogen for 20 hours, after which it was complete as judged by TLC and HPLC. The reaction mixture was concentrated to remove MeOH. The resulting residue was dissolved in DCM, washed twice with H2O, once with brine, dried (Na2SO4), filtered, and concentrated to give (R)-ethyl 2-amino-5-methylcyclopent-1-enecarboxylate (102 g, 97% yield) as an orange oil. LC/MS (APCI+) m/z 170 [M+H]+.

Step 3: A solution containing (R)-ethyl 2-amino-5-methylcyclopent-1-enecarboxylate (161.61 g, 955.024 mmol) and ammonium formate (90.3298 g, 1432.54 mmol) in formamide (303.456 ml, 7640.19 mmol) was heated to an internal temperature of 150° C. and stirred for 17 hours. The reaction mixture was cooled, and transferred to a 2 L single neck flask.

Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried ($Na_2SO_4$), filtered, and concentrated. The resulting brown oil was dissolved in minimal DCM, and this solution was added using a separatory funnel to a stirred solution of ether (ca. 5 vol of ether vs. DCM solution), causing some brown precipitate to form. This brown precipitate was removed by filtration through a medium frit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a brown-yellow pasty solid. LC/MS (APCI−) m/z 149.2.

Step 4: Neat $POCl_3$ (463.9 ml, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature, then heated to reflux and stirred for 70 minutes. The reaction was complete as determined by HPLC. The reaction mixture was cooled to room temperature, and the excess $POCl_3$ was quenched in 4 portions as follows: Reaction mixture transferred to separatory funnel and dripped into a beaker containing ice and saturated $NaHCO_3$ solution cooled in an ice bath. Once the addition of each portion of the reaction mixture was completed, the quenched mixture was stirred 30 minutes to ensure complete destruction of $POCl_3$ prior to transfer to separatory funnel. The mixture was transferred to the separatory funnel and extracted twice with DCM. The combined extracts were dried ($Na_2SO_4$), filtered, and concentrated. The crude was purified on silica gel as follows: silica gel (1 kg) was slurried in 9:1 hexane:ethyl acetate onto a 3 L fitted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as a brown oil. Triethylamine (93.0 ml, 534 mmol) and tert-butyl piperazine-1-carboxylate (34.8 g, 187 mmol) was added to a solution of (R)-4-chloro-5-methyl-6,7-dihydro-5H-cyclopenta[d]pyrimidine (30.0 g, 178 mmol) in n-BuOH (250 mL). The reaction mixture was heated to reflux under nitrogen and stirred overnight (17 hours), after which it was concentrated on a rotavap. The resulting oil was dissolved in DCM, washed with $H_2O$, dried ($Na_2SO_4$), filtered, and was concentrated. The resulting brown oil was purified on silica gel eluting first with 2:1 hexanes:ethyl acetate until product eluting cleanly, then gradient 1:1 to 1:5 DCM:ethyl acetate to give (R)-tertbutyl 4-(5-methyl-6,7-dihydro-5H-cyclopenta[d]pyrimidin-4-yl)piperazine-1-carboxylate (42.0 g, 74.1% yield) as a beige powder. LC/MS (APCI+) m/z 319.1 $[M+H]^+$.

Step 5: Solid 77% max. MCPBA (23.9 g, 107 mmol) was added portionwise to a 0° C. solution of (R)-tert-butyl 4-(5-methyl-6,7-dihydro-5H-cyclopenta[d]pyrimidin-4-yl)piperazine-1-carboxylate (20.0 g, 62.8 mmol) in $CHCl_3$ (310 mL). The reaction mixture was stirred 5 for minutes, then warmed to room temperature and stirred for 90 minutes. HPLC looked similar after 7.5 hours. The reaction mixture was cooled to 0° C., then $NaHCO_3$ (13.2 g, 157 mmol) and another 0.5 equivalents of m-CPBA were added. The reaction mixture was stirred overnight (14 hours). The reaction mixture was cooled to 0° C., and a solution of $Na_2S_2O_3$ (29.8 g, 188 mmol) in $H_2O$ (50 mL) was added dropwise by addition funnel. This was followed by a solution of $Na_2CO_3$ (24.6 g, 232 mmol) in $H_2O$ (70 mL) by addition funnel (mixture turns homogeneous). The reaction mixture was stirred for 30 minutes, then the mixture was extracted with $CHCl_3$ (3×150 mL) The combined extracts were dried ($Na_2SO_4$), filtered, and concentrated to give the N-oxide. LC/MS (APCI+) m/z 335.1 [M+H]+.

Step 6: $Ac_2O$ (77.0 ml, 816 mmol) was added to the N-oxide (21.0 g, 62.8 mmol) from Step 5. The reaction mixture was heated under nitrogen in a 90° C. sand bath and stirred for 100 minutes. The reaction mixture was cooled to room temperature, and excess acetic anhydride was removed by rotary evaporation. The resulting oil was dissolved in DCM, which was then poured carefully into ice saturated $Na_2CO_3$. The mixture was extracted with DCM, and the combined extracts were dried ($Na_2SO_4$), filtered, and concentrated to give (5R)-tert-butyl 4-(7-acetoxy-5-methyl-6,7-dihydro-5H-cyclopenta[d]pyrimidin-4-yl)piperazine-1-carboxylate (23.6 g, 100%) as a brown foam. LC/MS (APCI+) m/z 377.1 [M+H]+.

Step 7: LiOH—$H_2O$ (6.577 g, 156.7 mmol) was added to a 0° C. solution of (5R)-tert-butyl 4-(7-acetoxy-5-methyl-6,7-dihydro-5H-cyclopenta[d]pyrimidin-4-yl)piperazine-1-carboxylate (23.6 g, 62.69 mmol) in 2:1 THF:$H_2O$ (320 mL). The reaction mixture was stirred for 10 minutes, and then warmed to room temperature. LC/MS looked the same at 3 hours and 4.5 hours. The reaction mixture was cooled to 0° C., and then saturated $NH_4Cl$ was added to the mixture. The mixture was stirred for 5 minutes, and most of the THF was removed by rotary evaporation. The mixture was extracted with EtOAc (3×250 mL), and the combined extracts were dried ($Na_2SO_4$), filtered, and concentrated. The crude was flashed on Biotage 65M: 4:1 DCM:ethyl acetate, then gradient to 1:1 to 1:4 DCM:ethyl acetate. Once the product was eluting, then ethyl acetate was flushed through the column. Then 30:1 DCM:MeOH eluted the rest of the product (8.83 g). The mixed fractions were re-flashed with Biotage 40M using the same conditions to give another 2.99 g which gave a combined yield of (5R)-tert-butyl 4-(7-hydroxy-5-methyl-6,7-dihydro-5H-cyclopenta[d]pyrimidin-4-yl)piperazine-1-carboxylate (11.82 g, 56.38% yield) as a brown foam. LC/MS (APCI+) m/z 335.1 [M+H]+.

Step 8: A solution of DMSO (5.45 ml, 76.8 mmol) in DCM (50 mL) was added dropwise by addition funnel to a −78° C. solution of oxalyl chloride (3.35 ml, 38.4 mmol) in DCM (150 mL) The reaction mixture was stirred for 35 minutes, and then a solution of (5R)-tert-butyl 4-(7-hydroxy-5-methyl-6,7-dihydro-5H-cyclopenta[d]pyrimidin-4-yl)piperazine-1-carboxylate (9.17 g, 27.4 mmol) in DCM (80 mL) was added slowly by addition funnel. The reaction mixture was stirred another 1 hour at −78° C., after which neat triethylamine (18.0 ml, 129 mmol) was added to the mixture. The reaction mixture was then allowed to warm to room temperature, and then it was stirred for 30 minutes. $H_2O$ was added. The mixture was extracted with DCM (3×200 mL), and the combined extracts were dried ($Na_2SO_4$), filtered, and concentrated in vacuo. The crude was purified on silica gel (Biotage 65M): the column was flushed with ca. 800 mL 4:1 DCM:EtOAc, then gradient to 1:1 DCM:ethyl acetate until product eluting, then 1:4 DCM:EtOAc eluted product to give (R)-tert-butyl 4-(5-methyl-7-oxo-6,7-dihydro-5H-cyclopenta[d]pyrimidin-4-yl)piperazine-1-carboxylate (7.5 g, 82.3% yield) as a brown foam. The foam was concentrated (3×) from DCM/hexanes, which gave a very light brown foam. HPLC>95% area. LC/MS (APCI+) m/z 333 [M+H]+.

Step 9: Triethylamine (4.33 ml, 31.1 mmol; degassed with nitrogen 30 minutes prior to use) and formic acid (1.36 ml, 36.1 mmol; degassed with nitrogen 30 minutes prior to use) were added to a solution of (R)-tert-butyl 4-(5-methyl-7-oxo-6,7-dihydro-5H-cyclopenta[d]pyrimidin-4-yl)piperazine-1-carboxylate (9.75 g, 29.3 mmol) in DCM (210 mL; degassed with nitrogen 30 minutes prior to use). The mixture was stirred for 5 minutes, then a Ru catalyst (0.0933 g, 0.147 mmol) was added. The reaction was stirred under positive nitrogen pressure overnight (18 hours). The reaction mixture was concentrated to dryness and dried on high vacuum. The impure material was flashed on Biotage 65M loaded 1:1 DCM:ethyl acetate 500 mL flushed, then 1:4 DCM:ethyl acetate until product (2nd spot), then gradient to neat ethyl acetate, then 25:1 DCM:MeOH eluted rest of product. The fractions were combined and concentrated on a rotary evaporator. The residue was concentrated again from DCM/hexanes to give a mixture of tert-butyl 4-((5R,7R)-7-hydroxy-5-methyl-6,7-dihydro-5H-cyclopenta[d]pyrimidin-4-yl)piperazine-1-carboxylate (major) and tert-butyl 4-((5R,7S)-7-hydroxy-5-methyl-6,7-dihydro-5H-cyclopenta[d]pyrimidin-4-yl)piperazine-1-carboxylate (minor) (9.35 g, 95.3% yield) as a beige foam. LC/MS (APCI+) m/z 335 [M+H]+. 1H NMR (CDCl3) shows 88% de by integration of carbinol methine.

Step 10: 4-Nitrobenzoyl chloride (4.27 g, 23.0 mmol) was added to a 0° C. solution of tert-butyl 4-((5R,7R)-7-hydroxy-5-methyl-6,7-dihydro-5H-cyclopenta[d]pyrimidin-4-yl)piperazine-1-carboxylate (7.0 g, 20.9 mmol) and triethylamine (4.38 ml, 31.4 mmol) in DCM (110 mL) The reaction mixture was stirred at room temperature overnight, after which saturated NaHCO3 was added. The mixture was stirred 10 minutes, and then extracted with DCM. The combined extracts were dried (Na2SO4), filtered, and concentrated. The crude was flashed on Biotage 65M (3:1 hexanes:ethyl acetate loaded crude, then 2:1 hexanes:ethyl acetate eluted tert-butyl 4-((5R,7R)-5-methyl-7-(4-nitrobenzoyloxy)-6,7-dihydro-5H-cyclopenta[d]pyrimidin-4-yl)piperazine-1-carboxylate and a few mixed fractions). Then tert-butyl 4-((5R,7S)-5-methyl-7-(4-nitrobenzoyloxy)-6,7-dihydro-5H-cyclopenta[d]pyrimidin-4-yl)piperazine-1-carboxylate was eluted using 1:2 hexanes:ethyl acetate. The fractions with product were concentrated by rotary evaporation to give tert-butyl 4-((5R,7R)-5-methyl-7-(4-nitrobenzoyloxy)-6,7-dihydro-5H-cyclopenta[d]pyrimidin-4-yl)piperazine-1-carboxylate (8.55 g, 84.5% yield) as a yellow foam. LC/MS (APCI+) m/z 484 [M+H]+. 1H NMR (CDCl3) shows single diastereomer). The fractions with other diastereomer were concentrated by rotary evaporation to give tert-butyl 4-((5R,7S)-5-methyl-7-(4-nitrobenzoyloxy)-6,7-dihydro-5H-cyclopenta[d]pyrimidin-4-yl)piperazine-1-carboxylate (0.356 g, 3.52% yield) as a brown foam. LC/MS (APCI+) m/z 484 [M+H]+.

Step 11: LiOH—H2O (0.499 g, 11.9 mmol) was added to a 0° C. solution of tert-butyl 4-((5R,7R)-5-methyl-7-(4-nitrobenzoyloxy)-6,7-dihydro-5H-cyclopenta[d]pyrimidin-4-yl)piperazine-1-carboxylate (2.30 g, 4.76 mmol) in 2:1 THF:H2O (40 mL) The reaction mixture was warmed to room temperature and stirred for 1 hour. The THF was removed by rotary evaporation, saturated NaHCO3 was added, and the mixture was extracted with ethyl acetate. The combined extracts were washed (1×) with saturated NaHCO3, dried (Na2SO4), filtered, and concentrated to give tert-butyl 4-((5R,7R)-7-hydroxy-5-methyl-6,7-dihydro-5H-cyclopenta[d]pyrimidin-4-yl)piperazine-1-carboxylate (1.59 g, 100.0% yield) as a yellow foam. HPLC after workup just product >98 area % pure. LC/MS (APCI+) m/z 335 [M+H]+. The tert-butyl 4-((5R,7S)-7-hydroxy-5-methyl-6,7-dihydro-5H-cyclopenta[d]pyrimidin-4-yl)piperazine-1-carboxylate was prepared using an analogous method.

Step 12: 4M HCl/dioxane (11.2 ml, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on high vacuum line. The crude was suspended in ether, sonicated, and stirred for 5 minutes. The solids were isolated by filtration through a medium frit funnel with nitrogen pressure, rinsed with ether, dried under nitrogen pressure, and dried further on a hi vacuum line to give (5R,7R)-5-methyl-4-(piperazin-1-yl)-6,7-dihydro-5H-cyclopenta[d]pyrimidin-7-ol dihydrochloride (0.440 g, 79.8% yield) as a yellow powder. LC/MS (APCI+) m/z 235. The (5R,7S)-5-methyl-4-(piperazin-1-yl)-6,7-dihydro-5H-cyclopenta[d]pyrimidin-7-ol dihydrochloride was prepared using an analogous method.

Step 13: Methyl 2-(4-chlorophenyl)acetate (36.7 g, 199 mmol) and paraformaldehyde (6.27 g, 209 mmol) were dissolved/suspended in DMSO (400 mL) and treated with NaOMe (537 mg, 9.94 mmol). The mixture was allowed to stir at room temperature for 2 hours to completion by TLC analysis of the crude. The reaction was poured into ice-cold water (700 mL; white emulsion) and neutralized with the addition of 1M HCl solution. The aqueous layer was extracted with ethyl acetate (3×), and the organics were combined. The organic layer was washed with water (2×), brine (1×), separated, dried over MgSO4, filtered, and concentrated in vacuo to afford the crude product as a yellow oil. The residue was loaded onto a large fritted filtered with silica gel and eluted with 9:1 hexanes:ethyl acetate until the starting material/olefin were collected. The plug was then eluted with 1:1 hexanes:ethyl acetate until the pure desired product was eluted completely. The concentrated pure fractions yielded methyl 2-(4-chlorophenyl)-3-hydroxypropanoate as a colorless oil (39.4 g, 92%).

Step 14: Methyl 2-(4-chlorophenyl)-3-hydroxypropanoate (39.4 g, 184 mmol) was dissolved in DCM (500 mL) and treated with TEA (64.0 mL, 459 mmol). The solution was cooled to 0° C. and slowly treated with MSCl (15.6 mL, 202 mmol), then allowed to stir for 30 minutes to completion by TLC analysis. The solution was partitioned with 1N HCl solution, and the aqueous layer was extracted once with DCM. The combined organic layer was washed once more with 1N HCl solution, separated, washed with diluted NaHCO3 solution, and separated. The organic layer was dried over MgSO4, filtered, and concentrated in vacuo to afford an orange oil. The residue was loaded onto a large fritted filter with a plug of silica gel and eluted with 9:1 hexanes:ethyl acetate affording the pure desired product by TLC analysis. The concentrated pure fractions yielded the methyl 2-(4-chlorophenyl)acrylate as a colorless oil (30.8 g, 85%). This methyl 2-(4-chlorophenyl)acrylate (500 mg, 2.54 mmol) was added as a solution in THF (1.35 mL) to a stirring solution of i-PrNH2 (217 uL, 2.54 mmol) in THF (5.0 mL) at 0° C. The reaction was allowed to stir at room temperature overnight to completion by LCMS analysis. The Boc2O (584 uL, 2.54 mmol) was added to the stirring amine via pipet. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as a colorless oil (854 mg, 94%). LC/MS (APCI+) m/z 256.1 [M-Boc]+.

Step 15: Methyl 3-(tert-butoxycarbonyl(isopropyl) amino)-2-(4-chlorophenyl)propanoate (133 g, 374 mmol) was dissolved in THF (1.0 L) and treated with KOTMS (56.0 g, 392 mmol) at room temperature. The mixture was allowed to stir overnight to completion by LCMS analysis of the crude. The mixture was concentrated in vacuo to afford a wet foam, which was allowed to dry under vacuum overnight to afford potassium 3-(tert-butoxycarbonyl(isopropyl)amino)-2-(4-chlorophenyl)propanoate as a white solid (148.7 g, 105%). LC/MS (APCI+) m/z 242.1 [M-Boc-K]+.

Step 16: Potassium 3-(tert-butoxycarbonyl(isopropyl) amino)-2-(4-chlorophenyl)propanoate (77.2 g, 203 mmol) was dissolved in THF (515 mL) and treated with pivaloyl chloride (26.3 mL, 213 mmol) at room temperature. The mixture was allowed to stir for 3 hours to form the mixed anhydride. (S)-4-benzyloxazolidin-2-one (46.1 g, 260 mmol) was dissolved in THF (600 mL) and cooled to −78° C. in a separate flask. The solution was treated with n-BuLi (102 mL of a 2.50M solution in hexanes, 254 mmol) and allowed to stir for one hour. The prepared anhydride solution was added to the stirring Li-oxazolidinone via cannula, and the mixture was allowed to warm to room temperature overnight. The mixture was quenched with the addition of saturated ammonium chloride solution, then partitioned between more water and ethyl acetate. The aqueous layer was extracted several times, and the organics were combined. The organic layer was washed with water, then brine, separated, dried over $MgSO_4$, filtered, and concentrated in vacuo. The residue was purified/separated (diastereomers) via chromatography (silica gel eluted with 4:1 hexanes:ethyl acetate) to afford the completely separated diastereomers as viscous oils: tert-butyl(R)-3-((S)-4-benzyl-2-oxooxazolidin-3-yl)-2-(4-chlorophenyl)-3-oxopropyl(isopropyl)carbamate (12.16 g, 24% based on ½ of acid racemate) and tert-butyl(S)-3-((S)-4-benzyl-2-oxooxazolidin-3-yl)-2-(4-chlorophenyl)-3-oxopropyl(isopropyl) carbamate (39.14 g, 77% based on ½ of acid racemate). LC/MS (APCI+) m/z 401.2 [M-Boc]+.

Step 17: LiOH—$H_2O$ (168 mg, 4.00 mmol) was added to a stirring solution of THF (30 mL) and water (15 mL) at room temperature until it was dissolved. The mixture was treated with hydrogen peroxide (658 uL of a 35% wt. solution in water, 8.00 mmol) and allowed to stir at room temperature for 10 minutes. The reaction was cooled to 0° C. in an ice bath, and the tert-butyl(S)-3-((S)-4-benzyl-2-oxooxazolidin-3-yl)-2-(4-chlorophenyl)-3-oxopropyl(isopropyl)carbamate (1.00 g, 2.00 mmol) was added dropwise via addition funnel as a solution in THF (15 mL) over a 10 minutes. The mixture was allowed to stir overnight at room temperature to completion by LCMS analysis of the crude. The reaction was cooled to 0° C., and then treated with 1M $Na_2SO_3$ (9.00 mL) solution via addition funnel over a ten minute period. After the addition was complete, the mixture was allowed to warm to room temperature for 10 minutes. The mixture was concentrated to remove the THF, and then diluted with water. The aqueous layer was washed twice with ethyl acetate (discarded). The aqueous layer was partitioned with ethyl acetate, then treated dropwise while stirring with 1M HCl until pH 2-3 was attained. The aqueous layer was extracted twice with ethyl acetate, and the organics were combined. The organic was washed with brine, separated, dried over $MgSO_4$, filtered, and concentrated in vacuo. The colorless oil product was dried under high vacuum for one hour to afford (S)-3-(tert-butoxycarbonyl(isopropyl)amino)-2-(4-chlorophenyl)propanoic acid as a viscous oil/foam (685 mg, 100%). LC/MS (APCI+) m/z 242.1 [M-Boc]+.

Step 18: A solution of (5R,7R)-5-methyl-4-(piperazin-1-yl)-6,7-dihydro-5H-cyclopenta[d]pyrimidin-7-ol dihydrochloride (2.92 g, 9.51 mmol) and (S)-3-(tert-butoxycarbonyl(isopropyl)amino)-2-(4-chlorophenyl)propanoic acid (3.25 g, 9.51 mmol) in DCM (40 mL) and DIEA (5.0 mL, 28.7 mmol) was stirred at room temperature for 10 minutes. HBTU (3.61 g, 9.51 mmol) was added to the mixture. The mixture was stirred at room temperature for 1 hour. The solvent was removed, and the residue was dissolved in ethyl acetate (500 mL) and washed with water (6×100 mL) The organic phase was dried and concentrated. The residue was subject to column chromatography, eluted by EtOAc-DCM/MeOH (20:1) to give tert-butyl(S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl) carbamate (3.68 g, 69%.) LC/MS (APCI+) m/z 558.2 [M+H]+.

Step 19: The tert-butyl(S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl) carbamate (2.50 g, 4.48 mmol) was dissolved in dioxane (22.4 mL) and treated with 4M HCl in dioxane (22.4 mL, 89.6 mmol) at room temperature. The resulting solution was allowed to stir overnight to completion by LCMS analysis of the crude. The solution was concentrated in vacuo to afford a gel that was dissolved in a minimal amount of methanol (10 mL). The solution was transferred via pipette to stirred ether (300 mL) to afford a white precipitate of desired product. The addition was about half when the white precipitate melted into a yellow gel. The material was concentrated in vacuo to afford a yellow gel which was allowed to stand under reduced pressure overnight to yield (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride as a light yellow powder (2.14 g, 90%).

$^1$H NMR ($D_2O$, 400 MHz) δ 8.39 (s, 1H), 7.37-7.35 (d, J=8.4 Hz, 2H), 7.23-7.20 (d, J=8.4 Hz, 2H), 5.29-5.25 (m, 1H), 4.33-4.29 (m, 1H), 4.14-4.10 (m, 1H), 3.89-3.19 (m, 11H), 2.23-2.17 (m, 1H), 2.08-1.99 (m, 1H), 1.20-1.18 (m, 6H), 0.98-0.96 (d, J=6.8 Hz, 3H). MS (APCI+) [M+H]+458.

Examples 3-9 shown in Table 1 can also be made according to the above-described methods.

TABLE 1

| Example | Structure | Name | LCMS or $^1$H NMR |
|---|---|---|---|
| 3 | 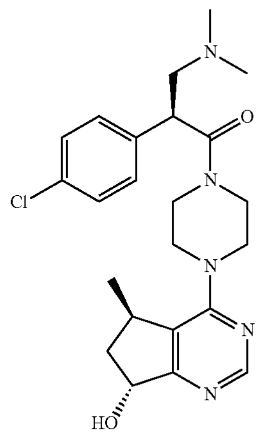 [SMILES: C[C@@H]1C[C@@H](O)c2ncnc(N3CCN(C(=O)[C@H](CN(C)C)c4ccc(Cl)cc4)CC3)c21] | (S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one | 444.1 |
| 4 | 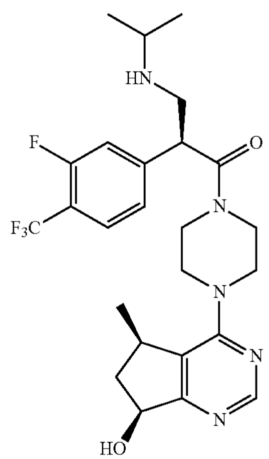 [SMILES: CC(C)NC[C@@H](C(=O)N1CCN(c2ncnc3c2[C@H](C)C[C@@H]3O)CC1)c1ccc(C(F)(F)F)c(F)c1] | (S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 510.3 |
| 5 | 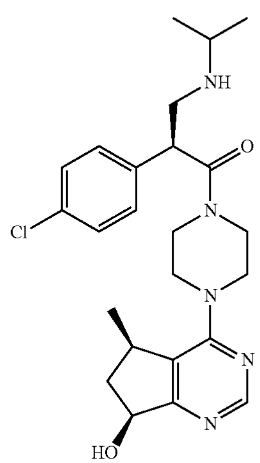 [SMILES: CC(C)NC[C@@H](C(=O)N1CCN(c2ncnc3c2[C@H](C)C[C@@H]3O)CC1)c1ccc(Cl)cc1] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 458.3 |

TABLE 1-continued

| Example | Structure | Name | LCMS or ¹H NMR |
|---|---|---|---|
| 6 | 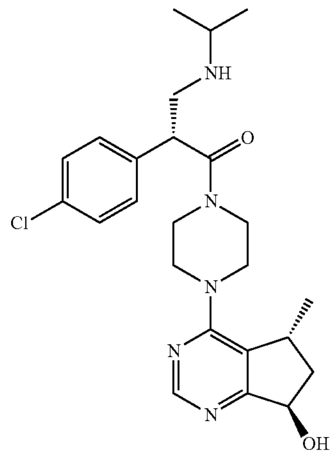 [SMILES: CC(C)NC[C@H](C(=O)N1CCN(c2ncnc3c2[C@H](C)C[C@H]3O)CC1)c1ccc(Cl)cc1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 458 |
| 7 | 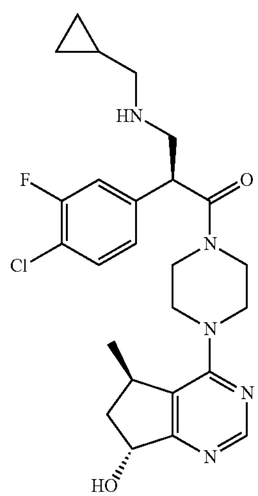 [SMILES: C[C@@H]1C[C@@H](O)c2ncnc(N3CCN(C(=O)[C@H](CNCC4CC4)c4ccc(Cl)c(F)c4)CC3)c21] | (S)-2-(4-chloro-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | LCMS (APCI+) m/z 488, 490 [M + H]+ |
| 8 | 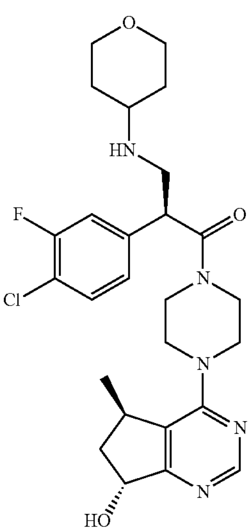 [SMILES: C[C@@H]1C[C@@H](O)c2ncnc(N3CCN(C(=O)[C@H](CNC4CCOCC4)c4ccc(Cl)c(F)c4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | LCMS (APCI+) m/z 518, 520 [M + H]+ |

TABLE 1-continued

| Example | Structure | Name | LCMS or ¹H NMR |
|---|---|---|---|
| 9 | 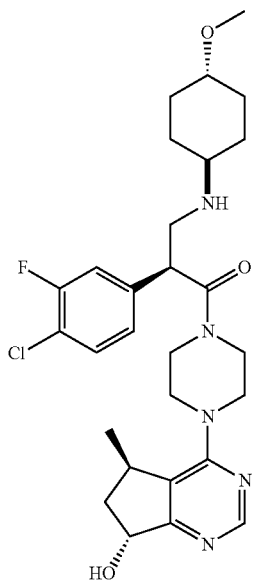 | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-((1r,4S)-4-methoxycyclohexylamino)propan-1-one | LCMS (APCI+) m/z 546 |

Example 10

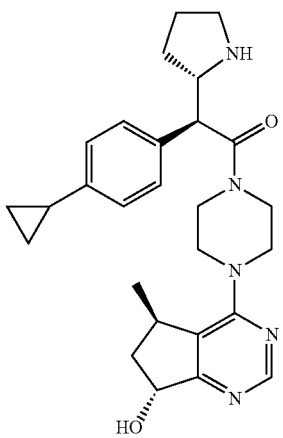 [SMILES: C[C@@H]1C[C@@H](O)c2ncnc(N3CCN(C(=O)[C@@H](c4ccc(C5CC5)cc4)[C@@H]4CCCN4)CC3)c21]

6)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone Step 1: Cyclopropylmagnesium bromide (64.0 mL, 32.00 mmol) in THF was treated with a solution of zinc (II) chloride (64.00 mL, 32.00 mmol) in THF. The mixture was stirred at ambient temperature for 20 minutes. 2-(4-Bromophenyl)acetonitrile (5.228 g, 26.67 mmol) and bis[tri-t-butyl phosphine]palladium (0.6814 g, 1.333 mmol) were added as a solution in THF (2 mL). The reaction was stirred at ambient temperature under nitrogen for 12 hours. The reaction was quenched with saturated NH4Cl, diluted with methylene chloride and separated. The aqueous layer was washed with methylene chloride (2x), and then the combined organic layers were washed with water (3x), dried over Na2SO4 and concentrated in vacuo. The crude product was subjected to chromatography on SiO2 eluting with 25:1 hexanes/ethyl acetate to yield 2-(4-cyclopropylphenyl)acetonitrile (2.76 g, 66%). 1H NMR (CDCl3, 400 MHz) ☐ 7.20 (d, J=8.2, 2H), 7.07 (d, J=8.2, 2H), 3.70 (s, 2H), 1.94-1.85 (m, 1H), 1.01-0.95 (m, 2H), 0.71-0.66 (m, 2H).

Step 2: Methanol (65 mL) was cooled to 0° C. and saturated with HCl (g). This solution was treated with a solution of 2-(4-cyclopropylphenyl)acetonitrile (2.76 g, 17.56 mmol) in methanol (6 mL). The reaction mixture was heated to reflux overnight under a drying tube containing CaSO4. The reaction was cooled and concentrated in vacuo. The crude mixture was re-suspended in ethyl acetate and water and then separated. The organic layer was washed with saturated NaHCO3, saturated NaCl, dried over Na2SO4 and concentrated in vacuo to provide methyl 2-(4-cyclopropylphenyl)acetate as an oil (3.10 g, 93%). 1H NMR (CDCl3, 400 MHz) δ 7.16 (d, J=8.3, 2H), 7.02 (d, 2H), 3.68 (s, 3H), 3.58 (s, 2H), 1.92-1.83 (m, 1H), 0.97-0.91 (m, 2H), 0.70-0.64 (m, 2H).

Step 3: Methyl 2-(4-cyclopropylphenyl)acetate (3.10 g, 16.30 mmol) was dissolved in a mixture of THF/MeOH/water (2:2:1, 80 mL), and the solution was treated with lithium hydroxide hydrate (0.8548 g, 20.37 mmol). The mixture was then stirred at ambient temperature for 4 hours. The reaction mixture was neutralized to a pH of 4 with 3N HCl and concentrated in vacuo. The solids were re-dissolved in ethyl acetate and water. The pH was re-adjusted to a pH of about 3 to about 4 with 3N HCl. The layers were then separated. The aqueous layer was washed with ethyl acetate (2x). The combined organic layers were then washed with saturated NaCl, dried over Na2SO4 and concentrated to yield 2-(4-cyclopropylphenyl)acetic acid (2.82 g, 98%). 1H NMR (CDCl3, 400 MHz) ☐ 7.16 (d, J 8.2, 2H), 7.03 (d, 2H), 3.60 (s, 2H), 1.92-1.83 (m, 1H), 098-0.91 (m, 2H), 0.70-0.64 (m, 2H).

Step 4: 2-(4-Cyclopropylphenyl)acetic acid (2.82 g, 16.003 mmol) was combined with (R)-4-benzyloxazolidin- 2-one (3.4030 g, 19.204 mmol) in toluene (14 mL). The suspension was treated with triethylamine (6.6917 mL, 48.010 mmol) and then heated to 80° C. The solution was treated dropwise with a solution of pivaloyl chloride (1.9893 mL, 16.003 mmol) in toluene (3.5 mL). The reaction was heated overnight at 80° C. The reaction was cooled and washed with 2N HCl and then separated. The aqueous layer was washed with toluene, and the combined organics were then washed with 2N HCl, water, saturated NaHCO3 (2×), saturated NaCl, dried over Na2SO4 and concentrated in vacuo. The crude product was subjected to chromatography on SiO2 eluting with 9:1 hexanes/ethyl acetate to yield (R)-4-benzyl-3-(2-(4-cyclopropylphenyl)acetyl)oxazolidin-2-one (3.43 g, 64%). 1H NMR (CDCl3, 400 MHz) ☐ 7.33-7.20 (m, 5H), 7.16-7.11 (m, 2H), 7.05 (d, J=8.2, 2H), 4.70-4.63 (m, 1H), 4.32-4.14 (m, 4H), 3.26 (dd, J1=3.2, J2=13.3, 1H), 2.75 (dd, J1=9.5, J2=13.3, 1H), 1.93-1.85 (m, 1H), 0.98-0.92 (m, 2H), 0.72-0.66 (m, 2H).

Step 5: (S)-2-((S)-1-(tert-Butoxycarbonyl)pyrrolidin-2-yl)-2-(4-cyclopropylphenyl)acetic acid was prepared according to the procedure described for Example 1, using (R)-4-benzyl-3-(2-(4-cyclopropylphenyl)acetyl)oxazolidin-2-one (0.287 g, 26%). MS (ESI+) [M+H] 345.7.

Step 6: (S)-tert-Butyl 2-((S)-1-(4-cyclopropylphenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate was prepared according to the procedure described for Example 3 using (S)-2-((S)-1-(tert-butoxycarbonyl)pyrrolidin-2-yl)-2-(4-cyclopropylphenyl)acetic acid, (0.199 g, 94%). MS (ESI+) [M+H] 562.1.

Step 7: (S)-2-(4-Cyclopropylphenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone was prepared according to the procedure described for Example 3 using (S)-tert-butyl 2-((S)-1-(4-cyclopropylphenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate (0.145 g, 77%). MS (ESI+) [M+H] 462.2. 1H NMR (CD3OD, 400 MHz) ☐ 8.56 (s, 1H), 7.26 (d, 2H), 7.13 (d, 2H), 5.29 (dd, 1H), 5.32-5.26 (dd, 1H), 4.32 (d, 1H), 4.29-4.18 (m, 1H), 4.12-3.95 (m, 2H), 3.88-3.61 (m, 6H), 3.51-3.38 (m, 1H), 3.35-3.30 (m, 1H), 2.32-2.24 (m, 1H), 2.22-2.03 (m, 2H), 1.95-1.85 (m, 2H), 1.82-1.73 (m, 2H), 1.40-1.34 (m, 1H), 1.16 (d, 3H), 1.01-0.95 (m, 2H), 0.69-0.64 (m, 2H).

Examples shown in Table 2 can also be made according to the above described methods.

TABLE 2

| Example | Structure | Name | LCMS or ¹H NMR |
|---|---|---|---|
| 11 | 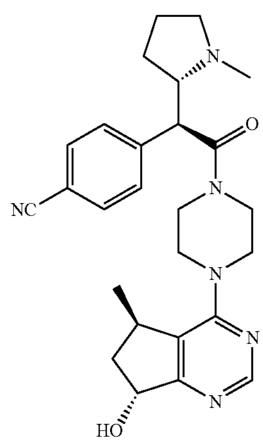 [SMILES: C[C@@H]1C[C@@H](O)c2ncnc(N3CCN(C(=O)[C@@H](c4ccc(C#N)cc4)[C@@H]4CCCN4C)CC3)c21] | 4-((S)-2-(4-((5R,7R)-7-hydroxy-5-methyl-6,7-dihydro-5H-cyclopenta[d]pyrimidin-4-yl)piperazin-1-yl)-1-((S)-1-methylpyrrolidin-2-yl)-2-oxoethyl)benzonitrile | m/z 461.3; ¹H NMR (500 MHz, DMSO-D6) d ppm 8.65 (s, 1H), 7.85 (d, 2H), 7.65 (d, 2H), 5.10 (t, 1H), 4.80 (d, 1H), 4.10-3.85 (m, 5H), 3.68 (m, 2H), 3.40 (m, 2H), 2.90 (s, 3H), 2.20-2.02 (m, 2H), 1.93 (m, 2H), 1.68 (m, 1H), 1.50 (m, 1H), 1.35-1.25 (m, 11H), 1.10 (d, 3H) |
| 12 | 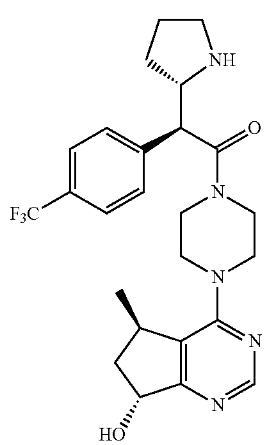 [SMILES: C[C@@H]1C[C@@H](O)c2ncnc(N3CCN(C(=O)[C@@H](c4ccc(C(F)(F)F)cc4)[C@@H]4CCCN4)CC3)c21] | (S)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone | m/z 490.3; ¹H NMR (500 MHz, DMSO-D6) d ppm 9.18 (m, 1H), 8.85 (m, 1H), 8.57 (s, 1H), 7.78 (d, 2H), 7.62 (d, 2H), 5.04 (t, 1H), 4.48 (d, 1H), 4.02 (m, 2H), 3.95 (m, 2H), 3.75-3.50 (m, 6H), 3.42 (m, 2H), 3.30-3.10 (m, 4H), 2.10-1.90 (m 3H), 1.75 (m, 1H), 1.70-1.50 (m, 2H), 1.04 (d, 3H) |

TABLE 2-continued

| Example | Structure | Name | LCMS or $^1$H NMR |
|---|---|---|---|
| 13 | 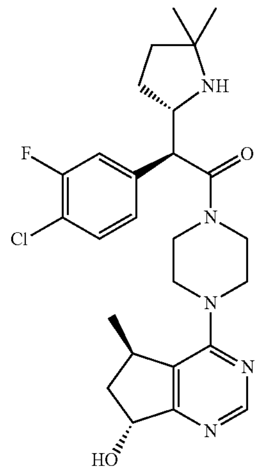 [SMILES: C[C@@H]1C[C@@H](O)c2ncnc(N3CCN(C(=O)[C@@H](c4ccc(Cl)c(F)c4)[C@@H]4CCC(C)(C)N4)CC3)c21] | (S)-2-(4-chloro-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | LCMS (apci+) 502 [M + H]+; 2.68 min; HPLC r.t. = 1.98 min, >97% purity; $^1$H NMR (400 MHz, D$_2$O) d ppm 8.37 (s, 1H), 7.43 (t, J = 8.2 Hz, 1H), 7.16 (d, J = 9.8 Hz, 1H), 7.06 (d, J = 8.2 Hz, 1H), 5.24 (t, J = 7.8 Hz, 1H), 4.27 (d, J = 9.4 Hz, 1H), 4.22-4.02 (m, 1H), 3.88-3.75 (m, 2H), 3.72-3.60 (m, 1H), 3.59-3.41 (m, 4H0, 3.37-3.22 (m, 1H), 2.24-2.11 (m, 0.5H), 2.10-1.94 (m, 0.5H), 1.89-1.71 (m, 4H), 1.36 (s, 3H), 1.30 (s, 3H), 0.96 (d, J = 7.0 Hz, 3H) |

Example 14

In Vitro Cell Proliferation Assays

The in vitro potency of the combinations of the compound of Example 2 with certain specific chemotherapeutic agents was measured using the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g., 96 or 384 well format. Data can be recorded by luminometer or CCD camera imaging device. The luminescence output is presented as relative light units (RLU), measured over time.

Figure 17A:
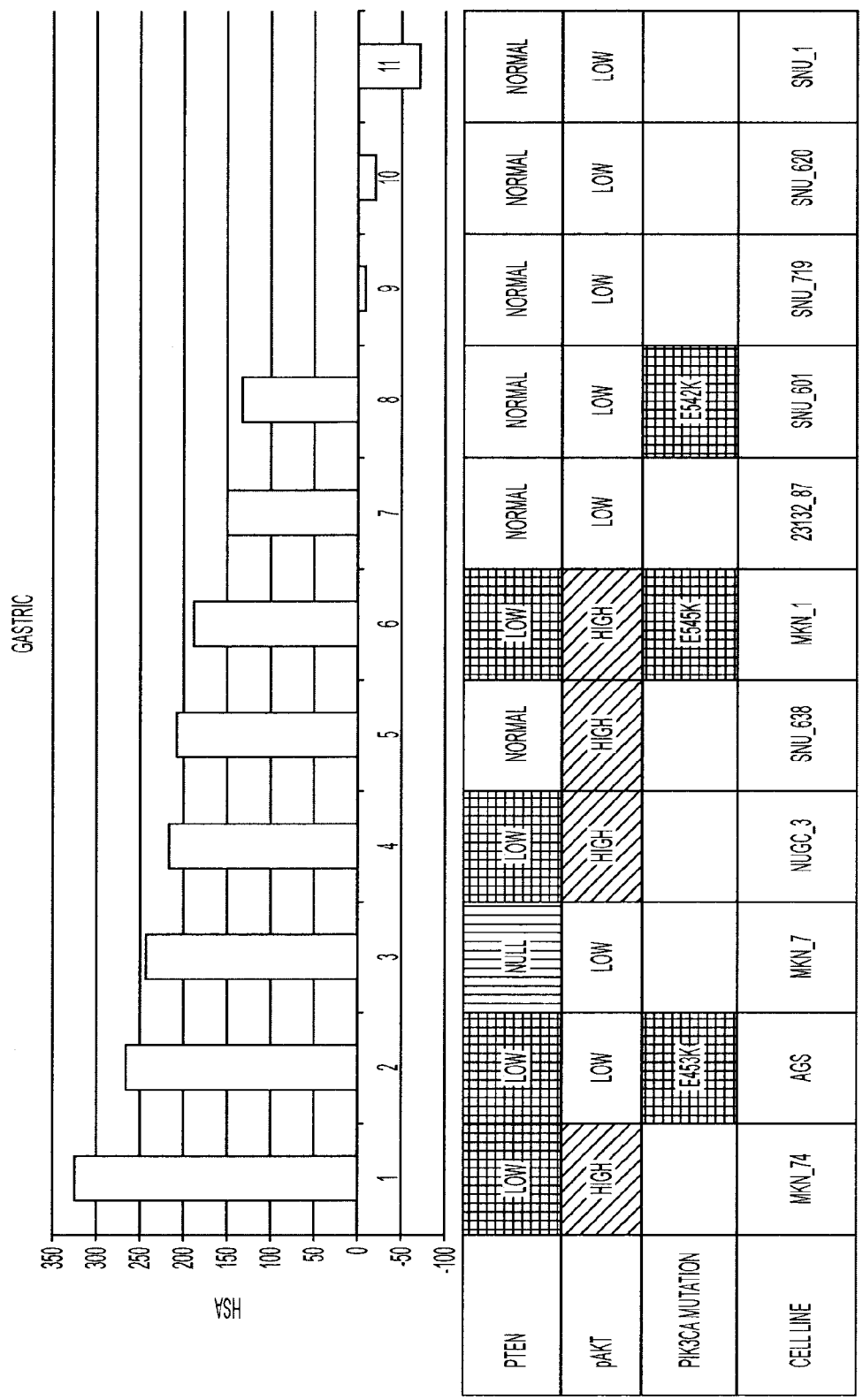
FIG. 17 illustrates data from Example 14 showing the activity of Example 2 plus 5-FU/Cisplatin is associated with AKT pathway activation, particularly in gastric and head and neck squamous cell carcinoma. Additive effects were observed for the combination of GDC-0068 plus 5-FU/cisplatin, and are associated with PTEN (low or null), pAKT (overexpression) and PI3K mutation and amplification.
Figure 17B:
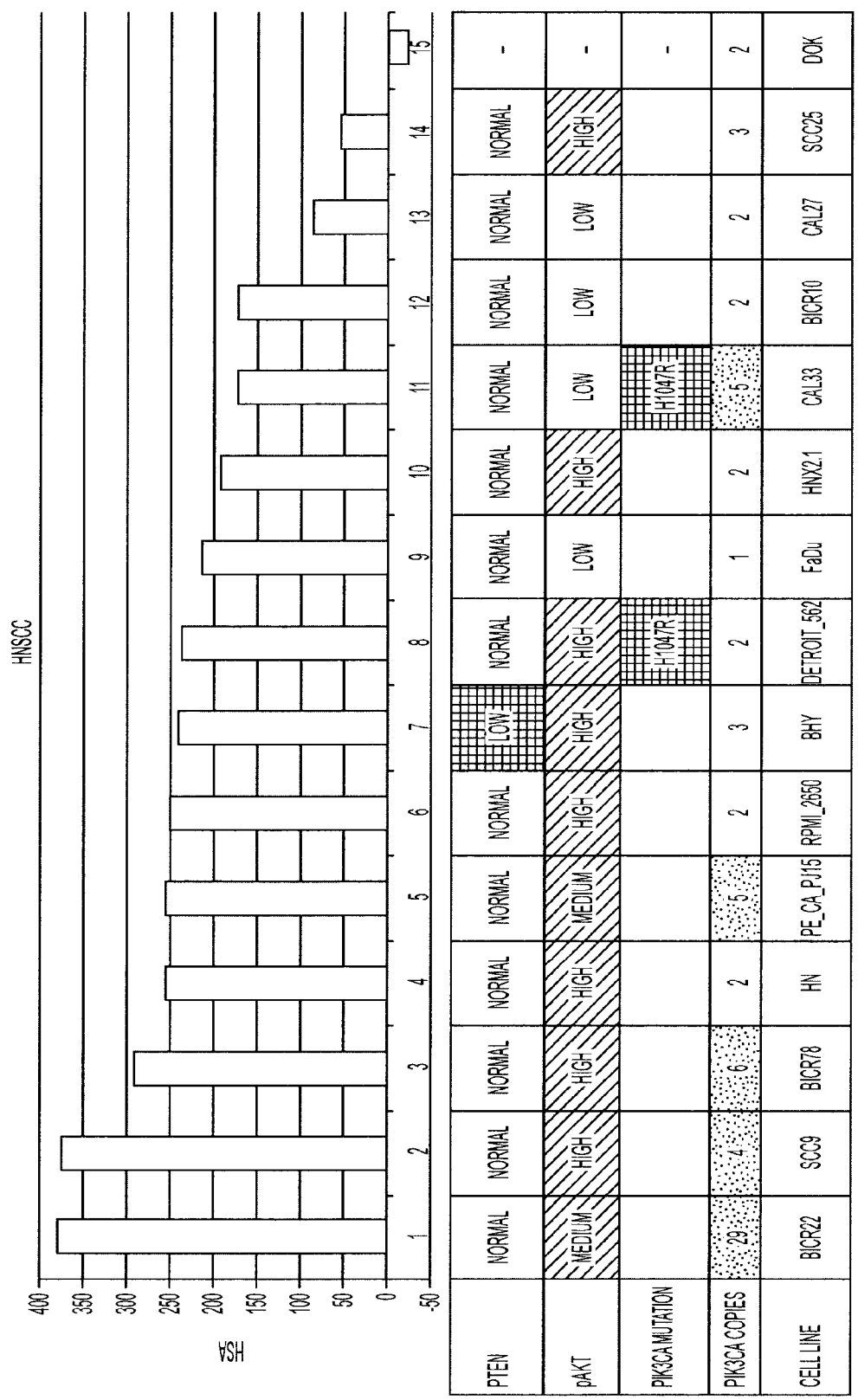
Figure 18:
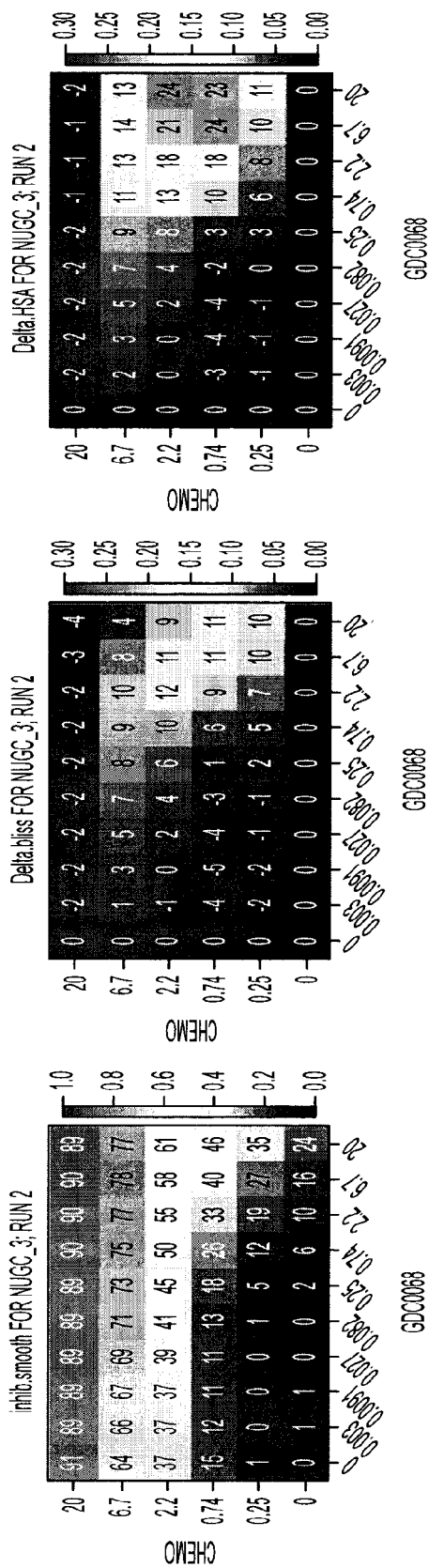
FIG. 18 illustrates BLISS score data from Example 14 showing the activity of Example 2 (GDC-0068) plus 5-FU/Cisplatin ("chemo") combinations in Gastric cell lines. Synergy is demonstrated in the combination in NUGC3 cell lines (Gastric cancer) where PTEN status is low and pAKT is overexpressed. Additionally, this particular cell line (NUGC3) shows additive effects at mid-level doses of 5-Fu/Cisplatin and high doses of GDC-0068.
Figure 19A:
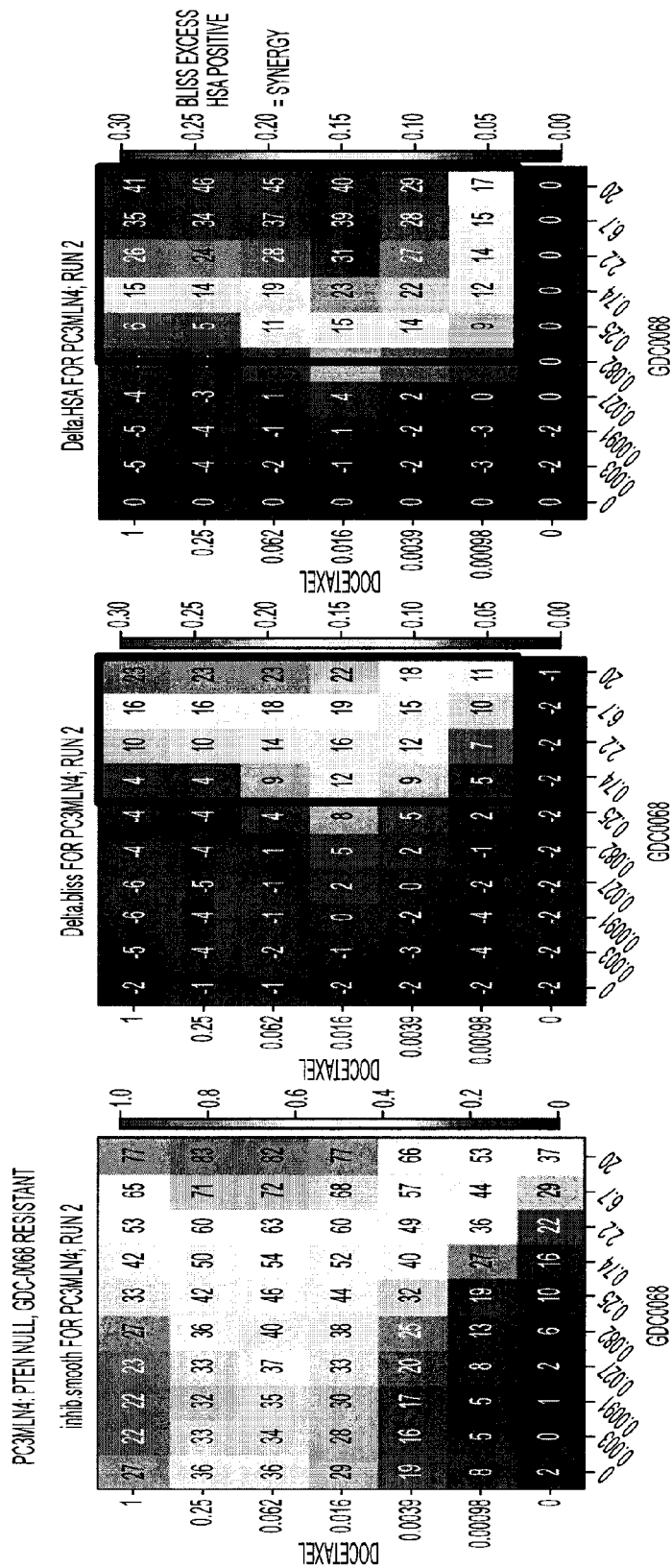
FIG. 19 illustrates data from Example 14 showing that Example 2 plus Docetaxel combinations show maximum synergy in PTEN null line which had minimal single agent response to Example 2.
Figure 19B:
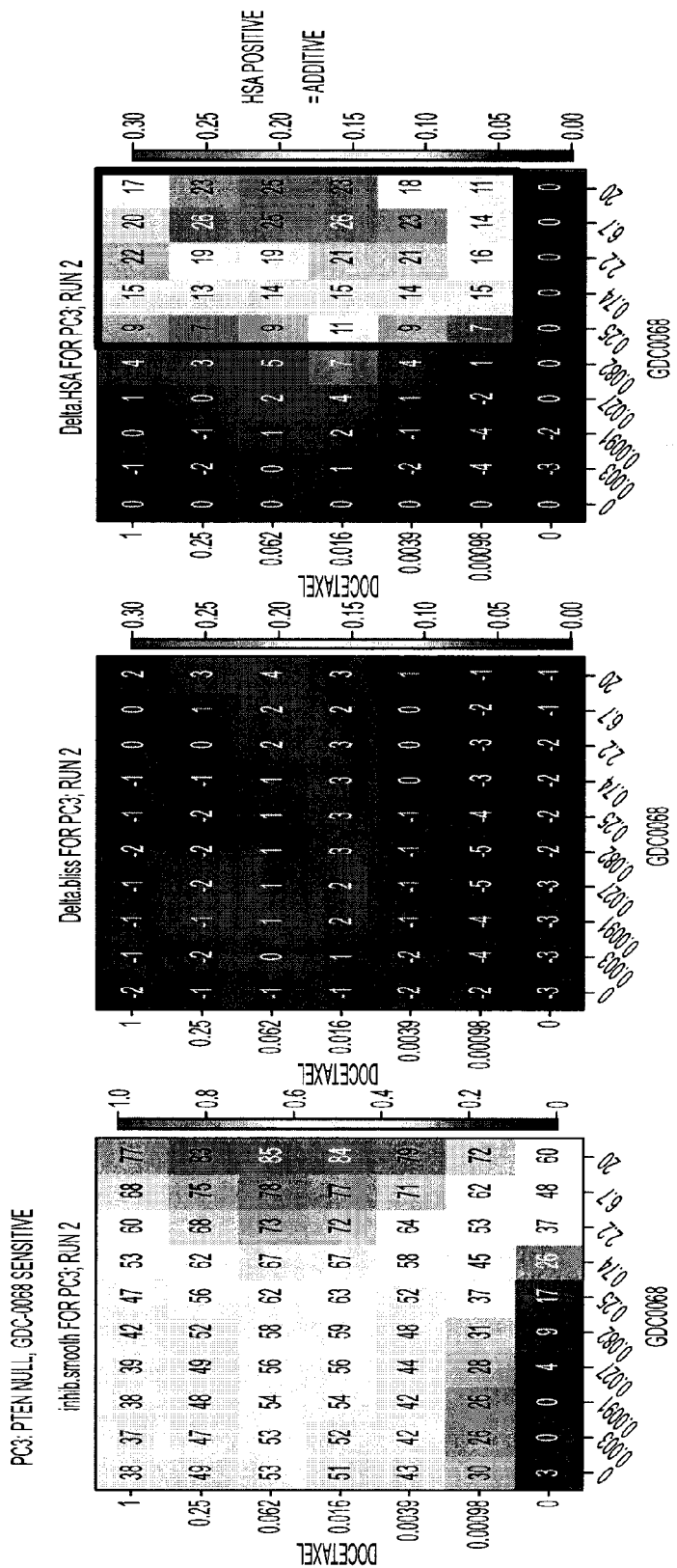
Figure 20A:
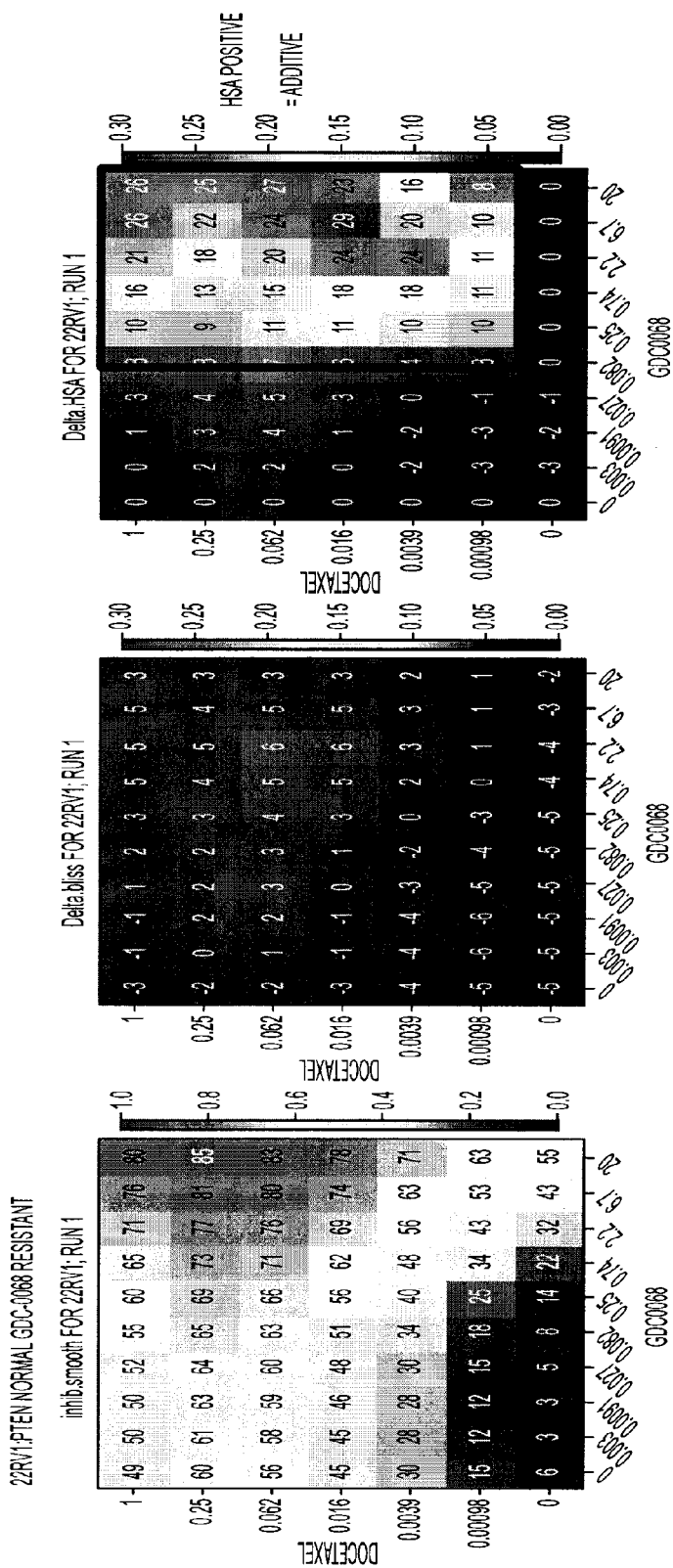
FIG. 20 illustrates data from Example 14 that shows that Example 2 plus Docetaxel combinations show weaker additivity and synergism in PTEN normal cell lines.
Figure 20B:
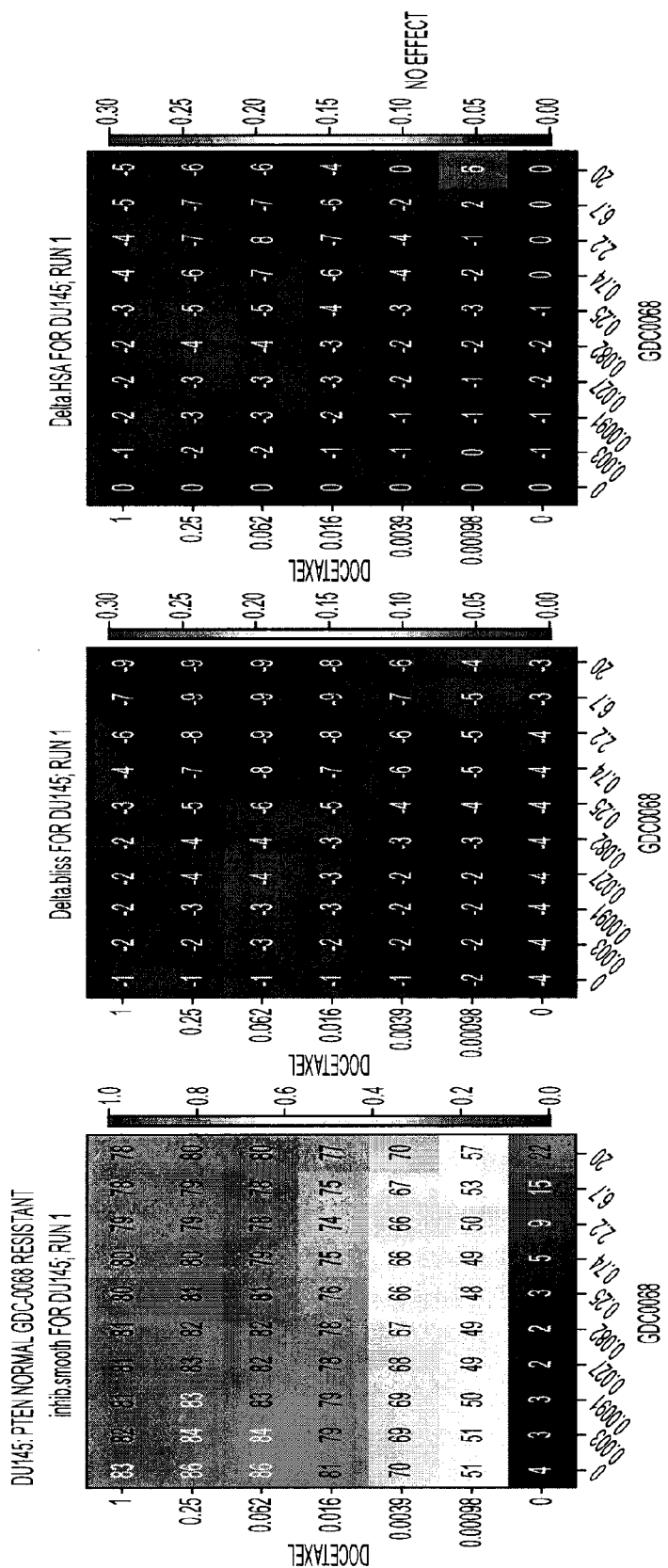
Figure 21A:
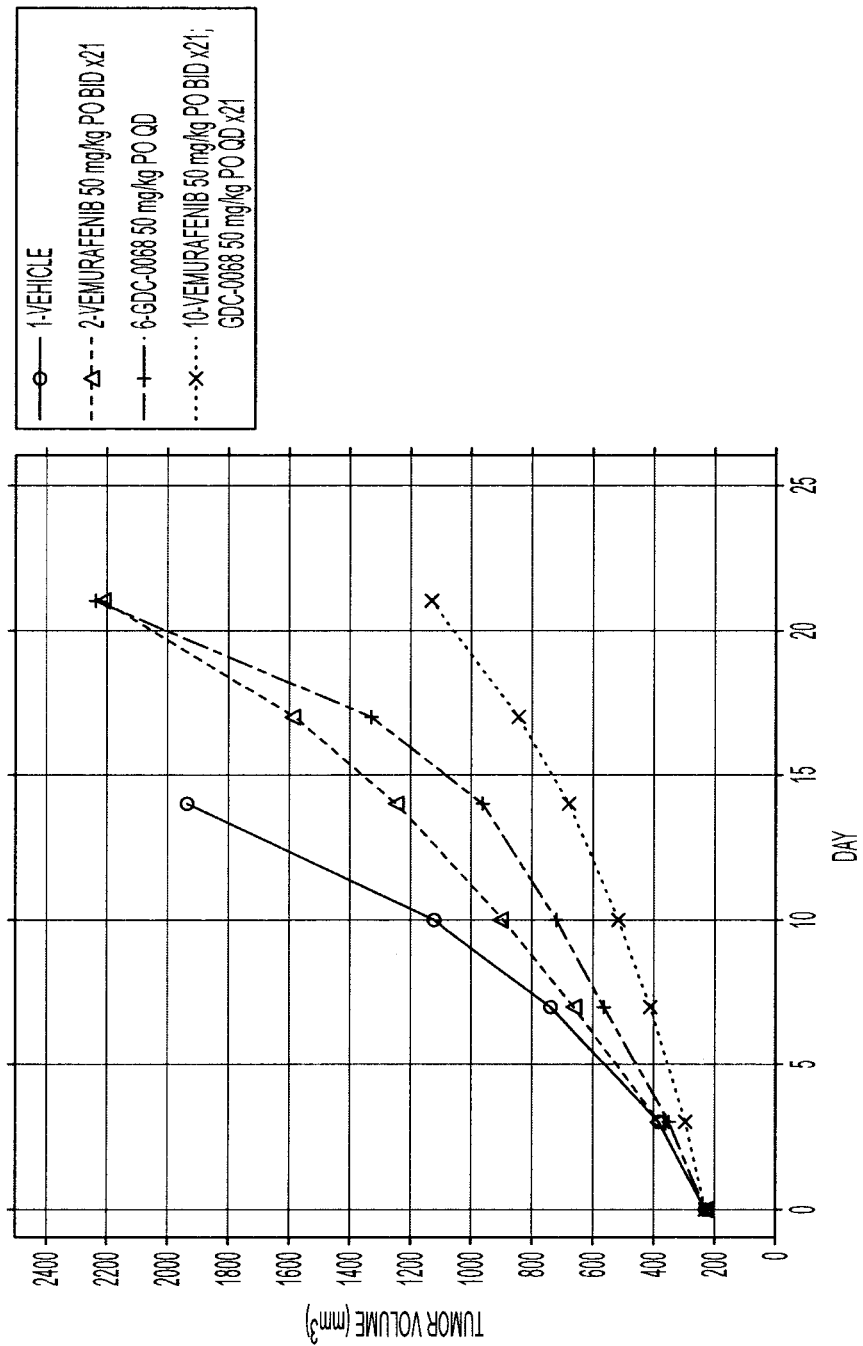
FIG. 21 illustrates results of an in vivo xenograft study, according to Example 15, using a compound of formula Ia (GDC-0068) in combination with a BRAF inhibitor (vemurafenib), dosed PO, in A2058 Melanoma Tumors.
Figure 21B:
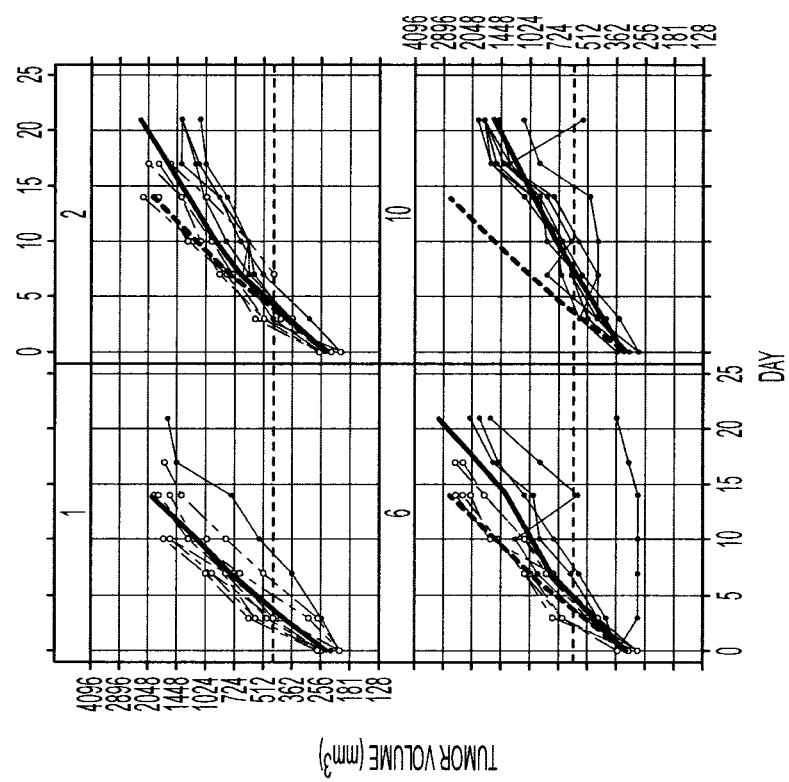
Figure 22B:
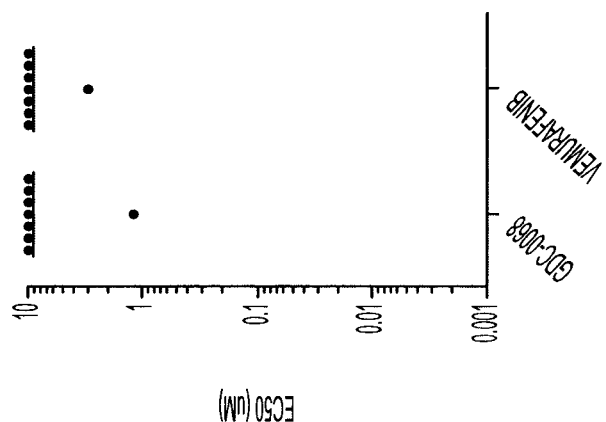
FIG. 22 illustrates in vitro EC50s for single agent GDC-0068 and vemurafenib in melanoma A375 cell lines (FIG. 22A) and melanoma A375 cell lines resistant to vemurafenib (FIG. 22B), respectively.
Figure 22A:
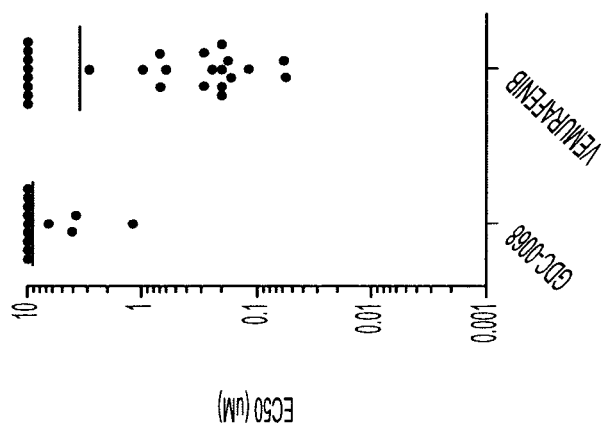
Figure 23B:
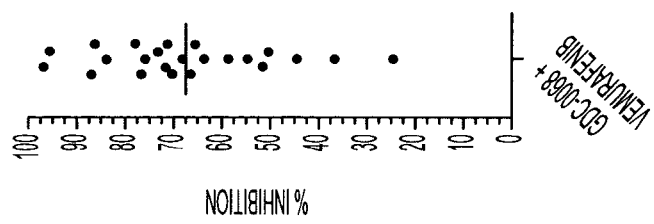
FIG. 23 illustrates in vitro EC50s for the combination of GDC-0068 and vemurafenib in melanoma A375 cell lines (FIG. 23A) and melanoma A375 cell lines resistant to vemurafenib (FIG. 23B), respectively.
Figure 23A:
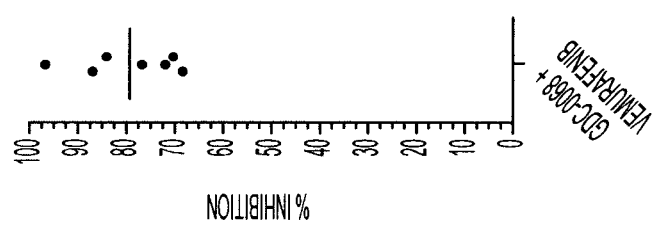
Figure 24:
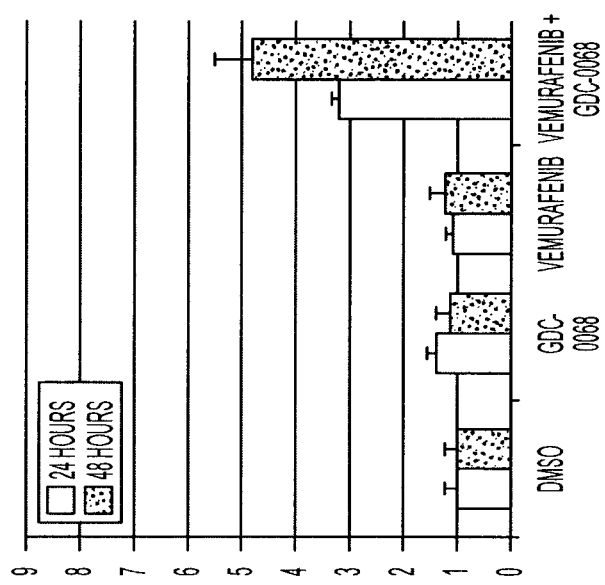
FIG. 24 illustrates absolute cell death at 24 and 48 hr time points relative to DMSO in Colo800 BRAF V600E mutant cell lines for GDC-0068 and vemurafenib single agent therapy compared to the synergistic combination of GDC-0068 plus vemurafenib in a Colo800 human melanoma cell line.

The anti-proliferative effects of combinations of the compound of Example 2 and certain chemotherapeutic agents were measured using the CellTiter-Glo® Assay. EC$_{50}$ values were established for the tested compounds and combinations. The range of in vitro cell potency activities was about 100 nM to about 10 µM. Data for representative combinations is provided in FIGS. 16-20. The data in FIG. 16 demonstrates that representative combinations provide additive or synergistic activity against a number of cancer types. FIG. 17 illustrates that combination effects of Example 2 with 5FU/C is associated with AKT pathway activation. FIG. 18 illustrates activity of Example 2 plus 5-FU/Cisplatin combinations in Gastric lines. FIG. 19 illustrates that Example 2 plus Docetaxel combinations show maximum effect in PTEN null line which had minimal single agent response to Formula I. FIG. 20 illustrates that Example 2 plus Docetaxel combinations are weaker in PTEN normal cell lines.

Example 15

In Vivo Tumor Xenograft Efficacy

The efficacy of representative combinations of the invention may be measured in vivo by implanting allografts or xenografts of cancer cells in rodents and treating the tumor-bearing animals with the combinations. Variable results are to be expected depending on the cell line, the presence or absence of certain mutations in the tumor cells, the sequence of administration the compound of Example 2 and chemotherapeutic agent, dosing regimen, and other factors. Subject mice were treated with drug(s) or control (Vehicle) and monitored over several weeks or more to measure the time to tumor doubling, log cell kill, and tumor inhibition.

Figure 2B:
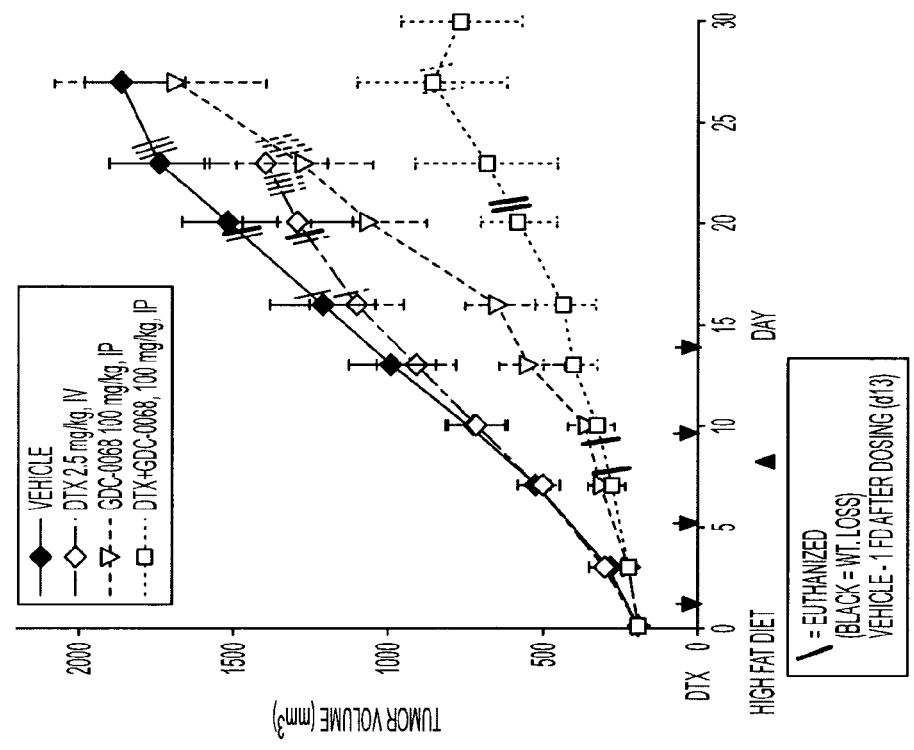
FIG. 2 illustrates results from Example 15 for the compound of Example 2 dosed intermittently either PO or IP and docetaxel in PC3-NCI prostate tumors.
Figure 2A:
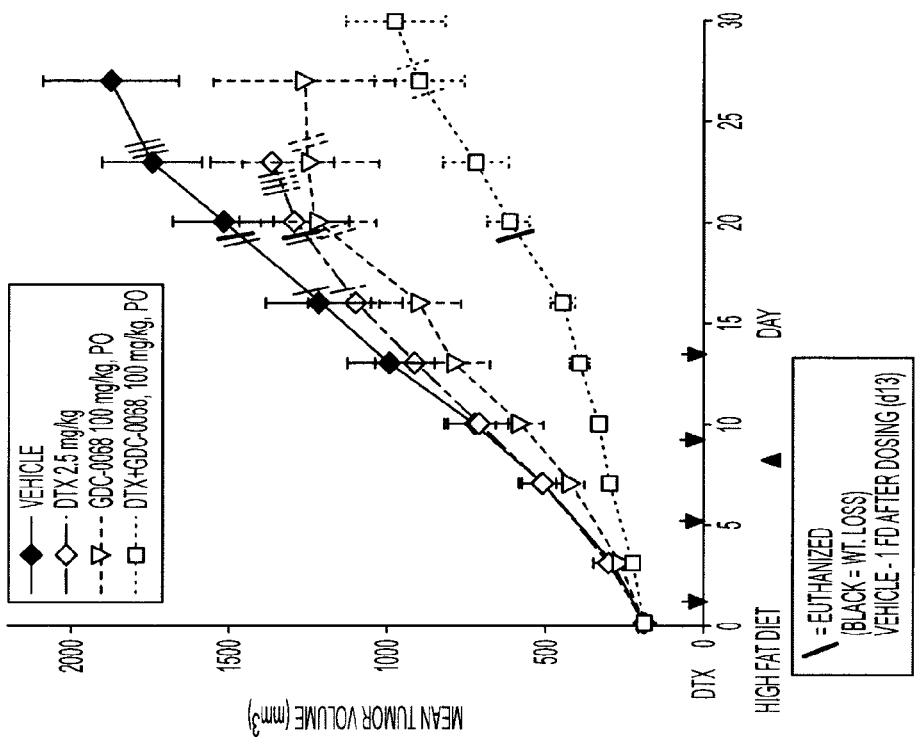
Figure 3:
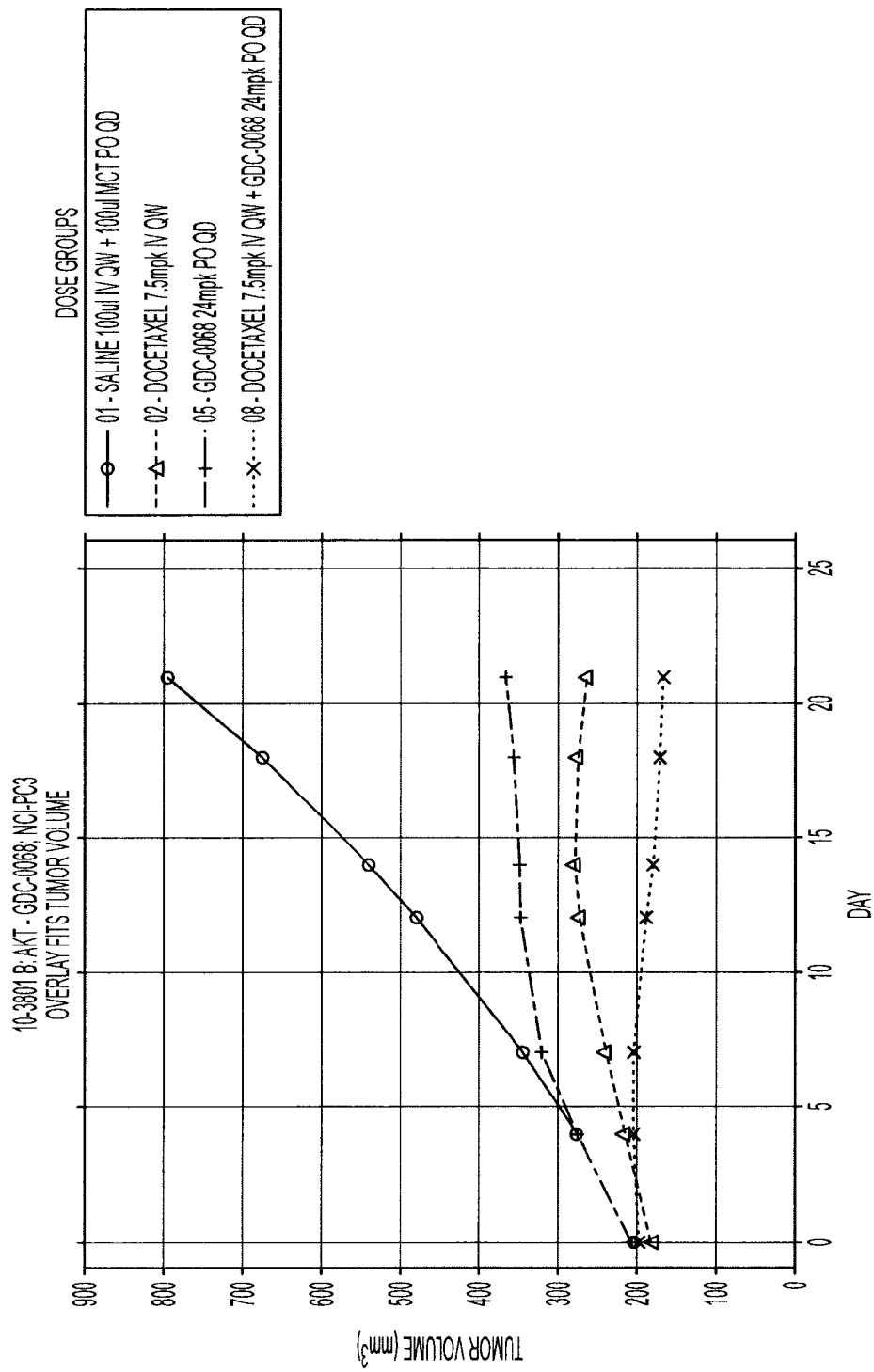
FIG. 3 illustrates results from Example 15 for the compound of Example 2 dosed PO and docetaxel in PC3-NCI prostate tumors.
Figure 5:
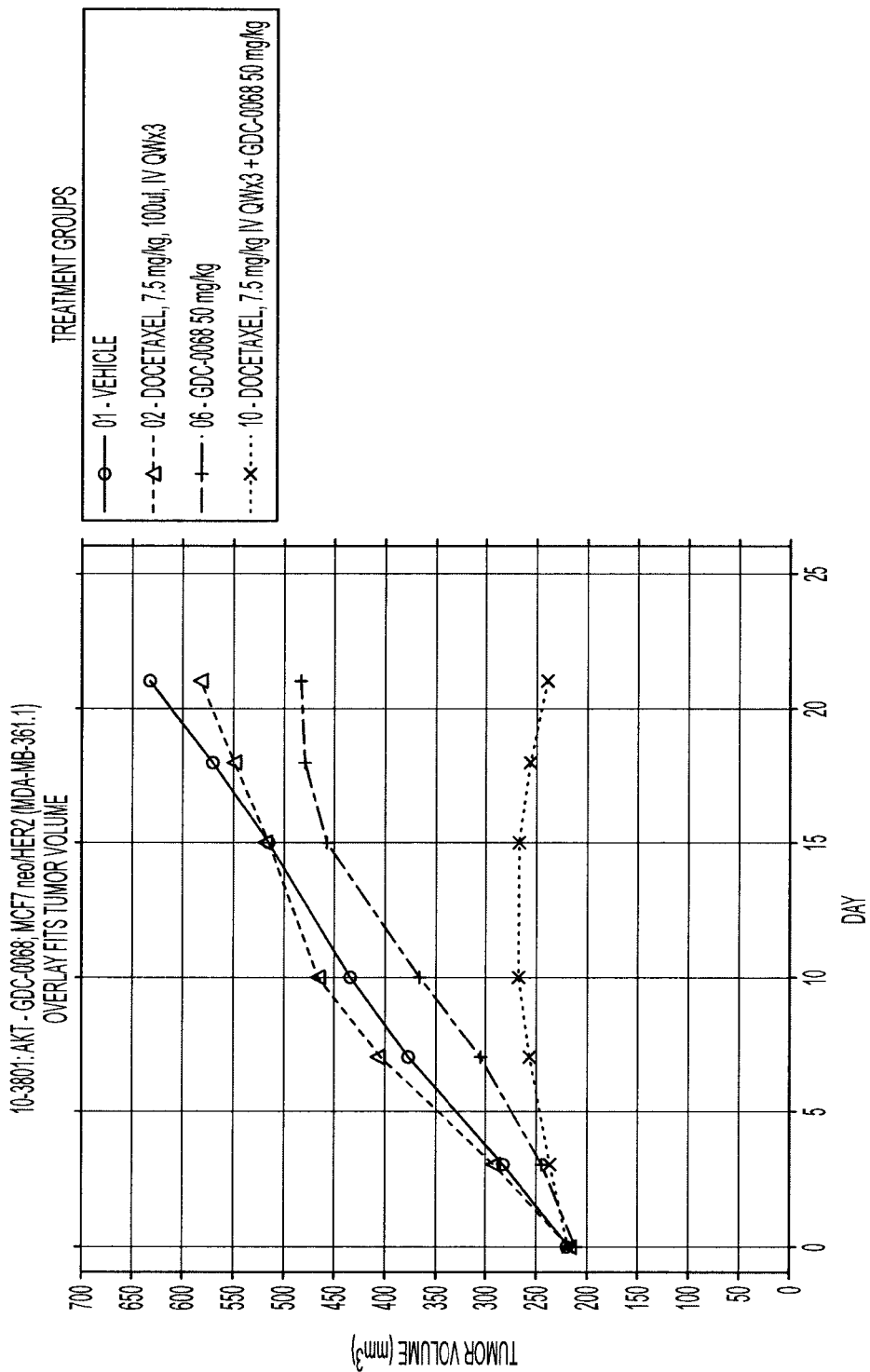
FIG. 5 illustrates results from Example 15 for the compound of Example 2 dosed PO and docetaxel in MCF7-neo/HER2 breast tumors.
Figure 6:
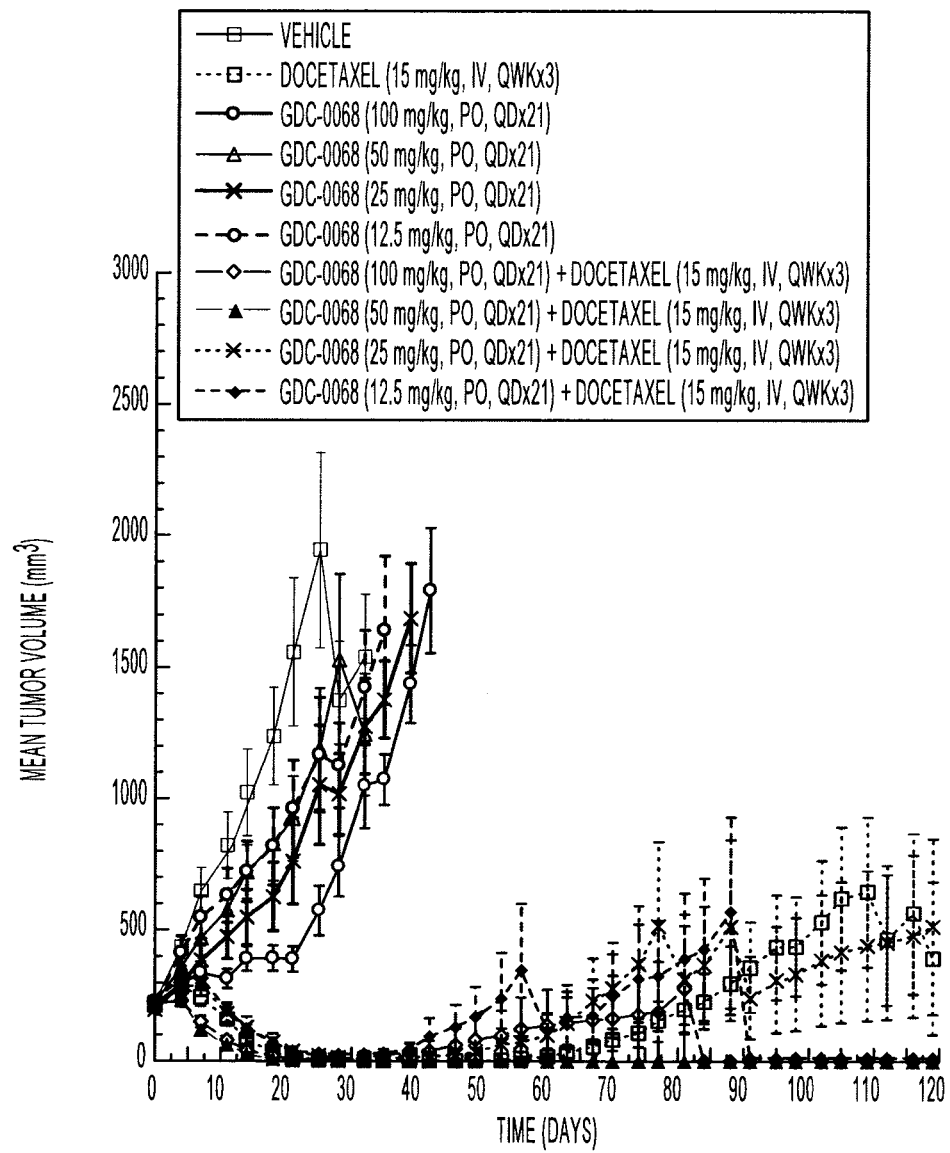
FIG. 6 illustrates results from Example 15 for the compound of Example 2 and docetaxel in MAXF401 mammary tumors.
Figure 7:
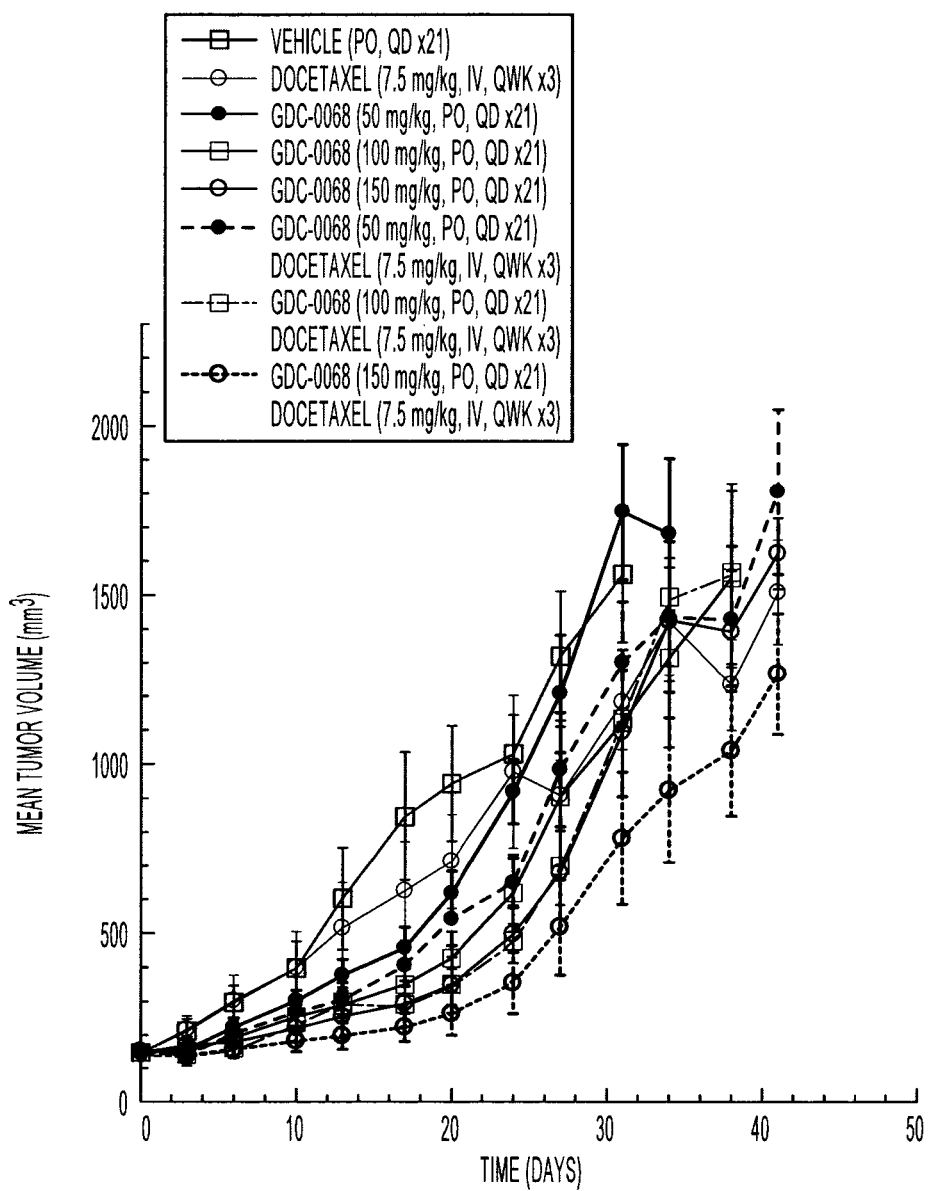
FIG. 7 illustrates results from Example 15 for the compound of Example 2 and docetaxel in SKOV3 ovarian tumors.
Figure 8:
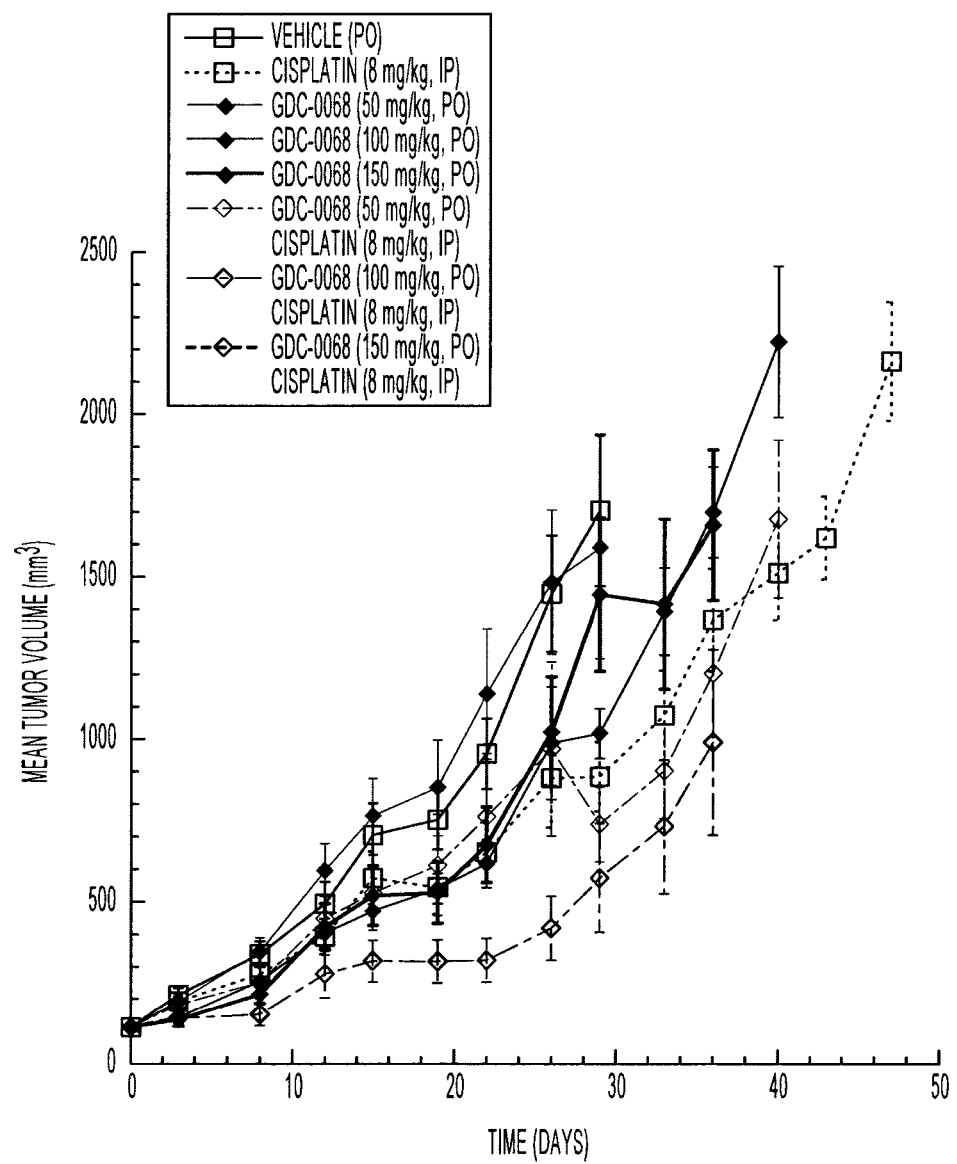
FIG. 8 illustrates results for the compound of Example 2 and cisplatnin in SKOV3 ovarian tumors.
Figure 9:
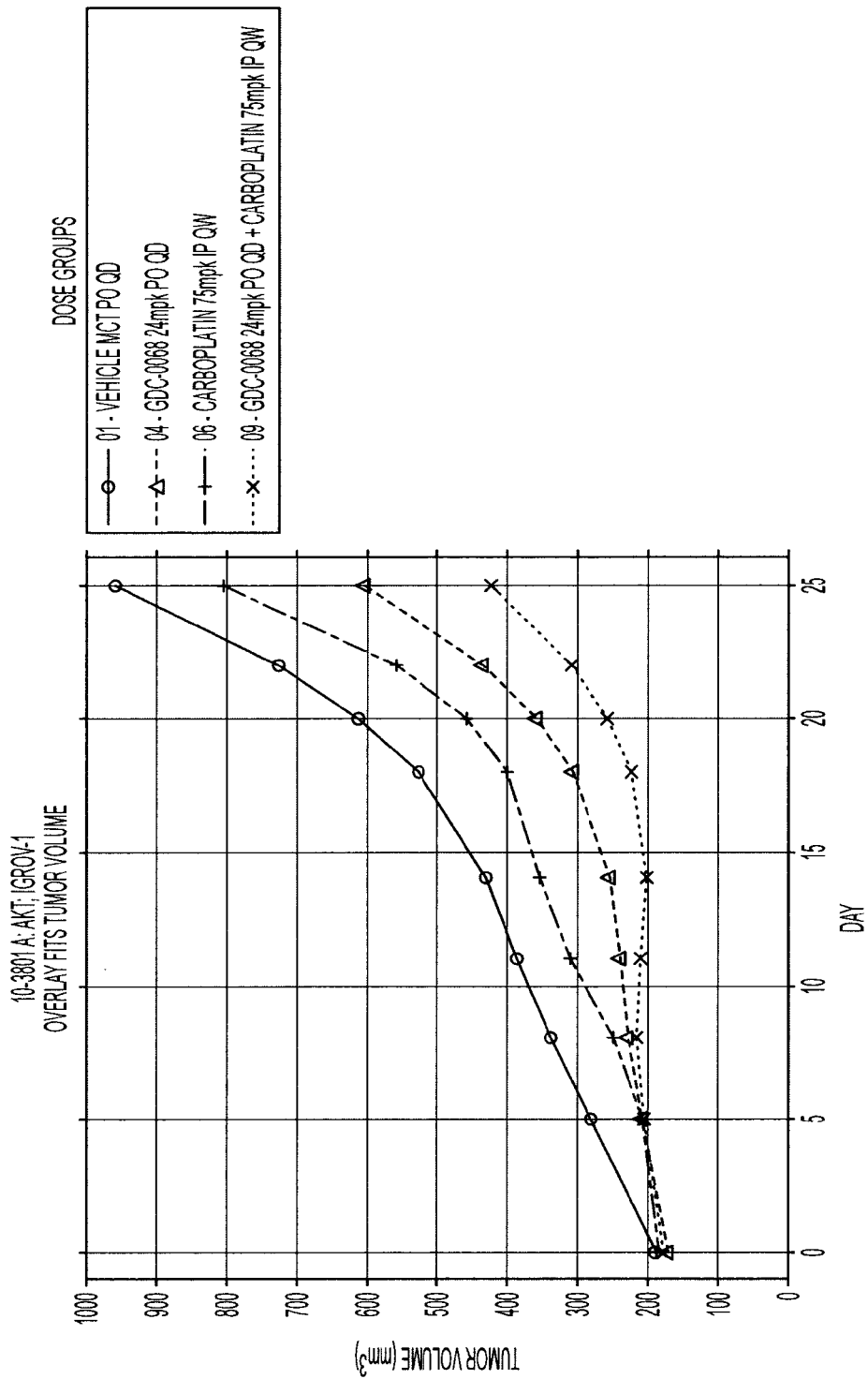
FIG. 9 illustrates results from Example 15 for the compound of Example 2 dosed PO and carboplatin in IGROV-1 ovarian tumors.
Figure 10A:
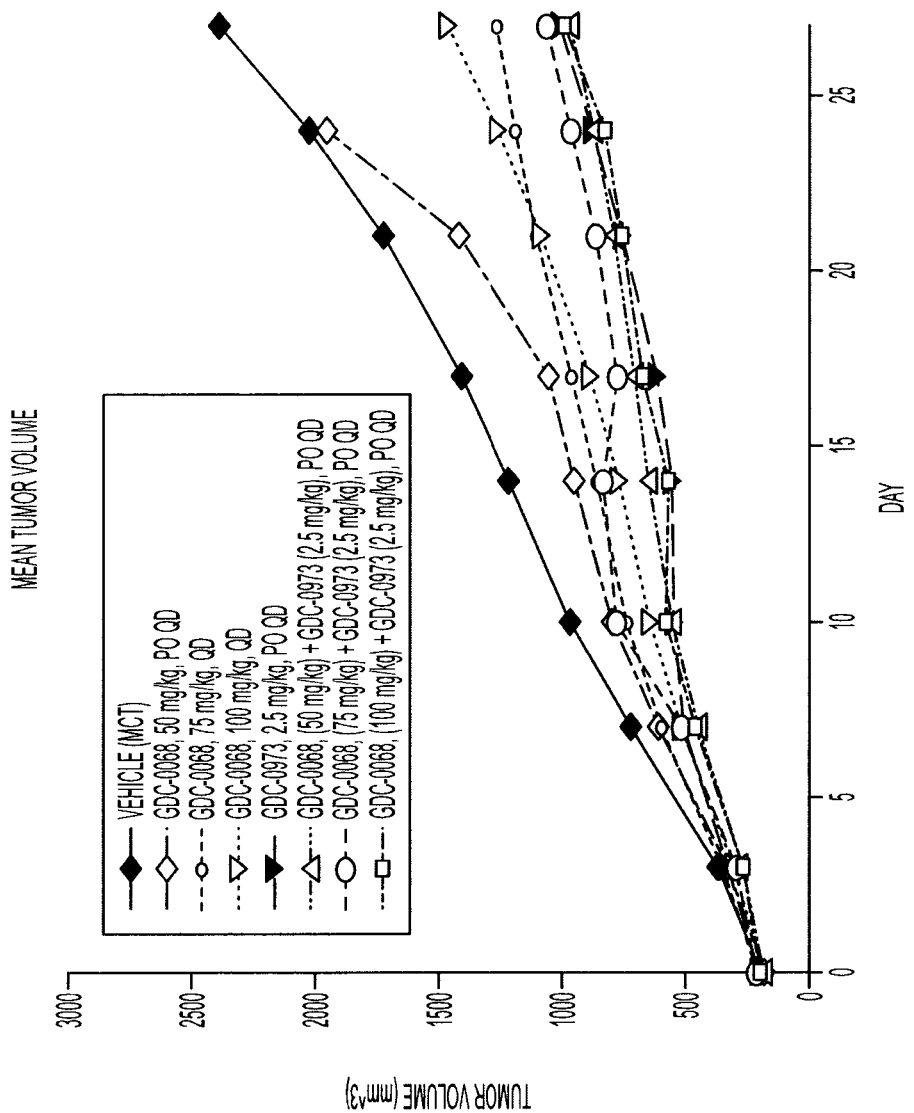
FIG. 10 illustrates results from Example 15 for the compound of Example 2 and GDC-0973 at 2.5 mg/kg.
Figure 10B:
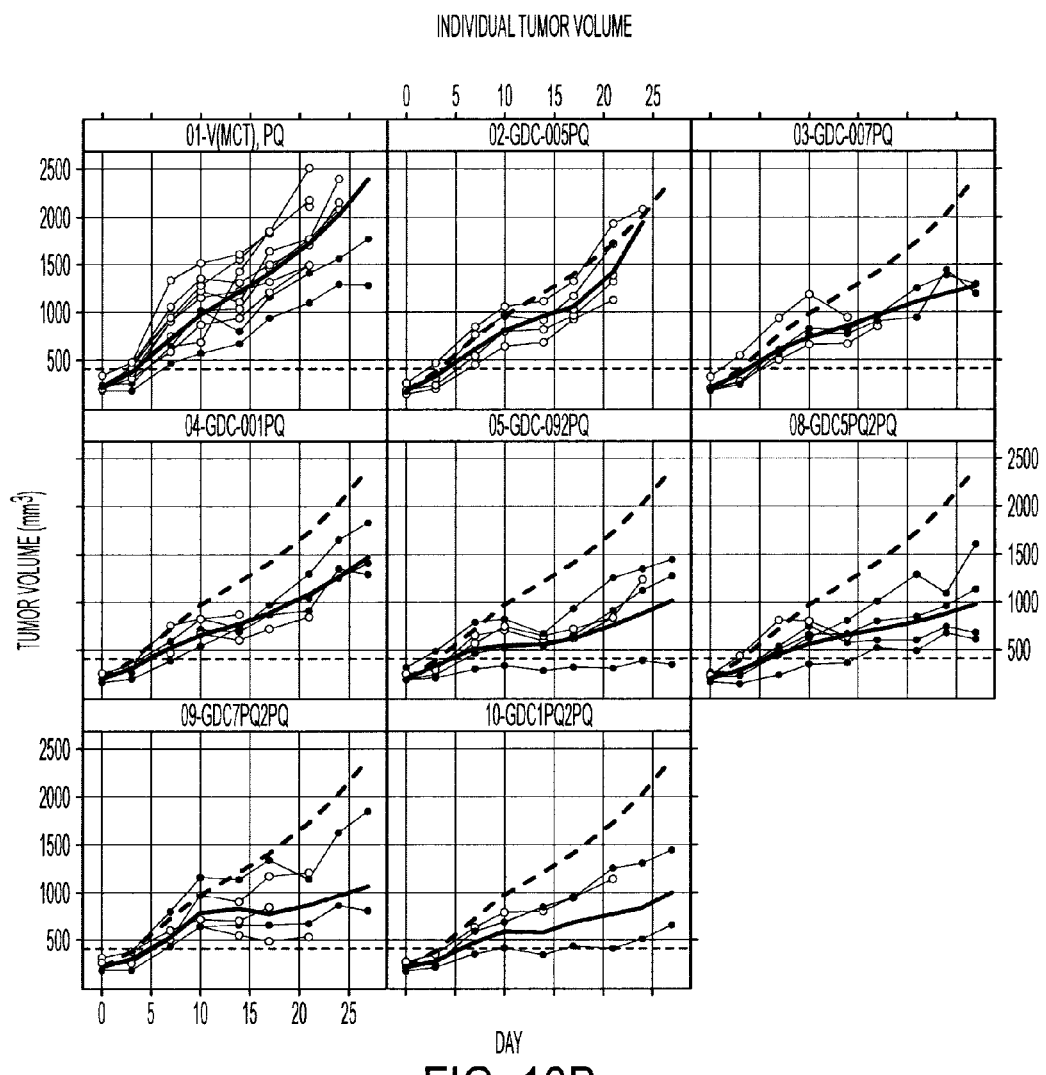
Figure 11A:
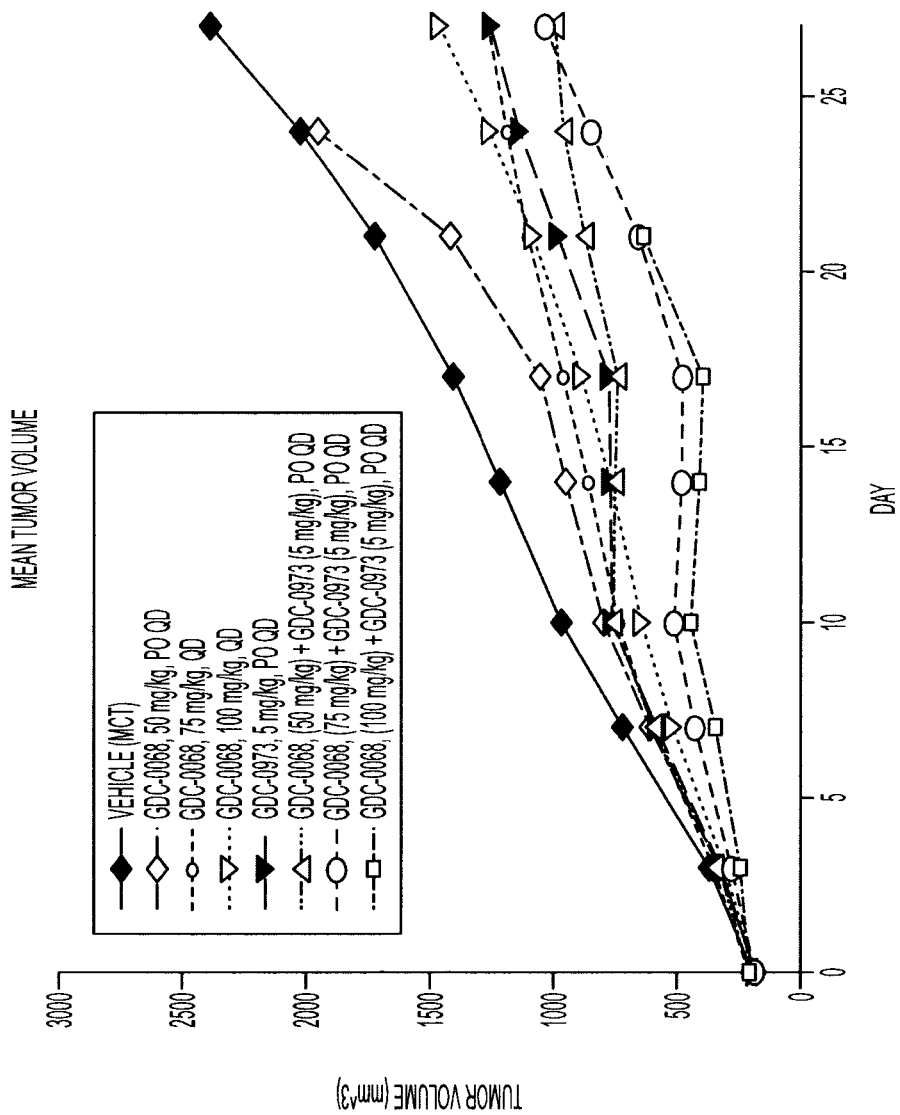
FIG. 11 illustrates results from Example 15 for the compound of Example 2 and GDC-0973 at 5.0 mg/kg.
Figure 11B:
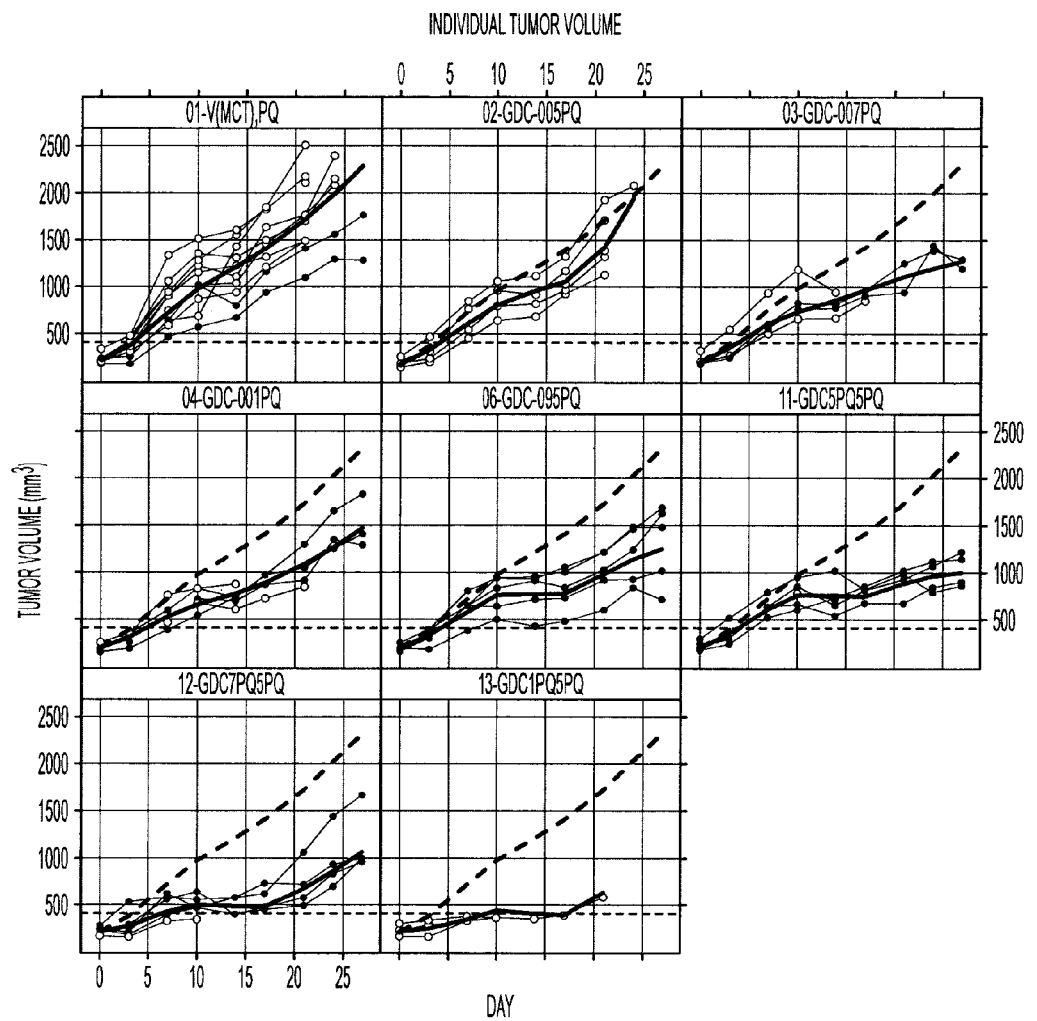
Figure 12A:
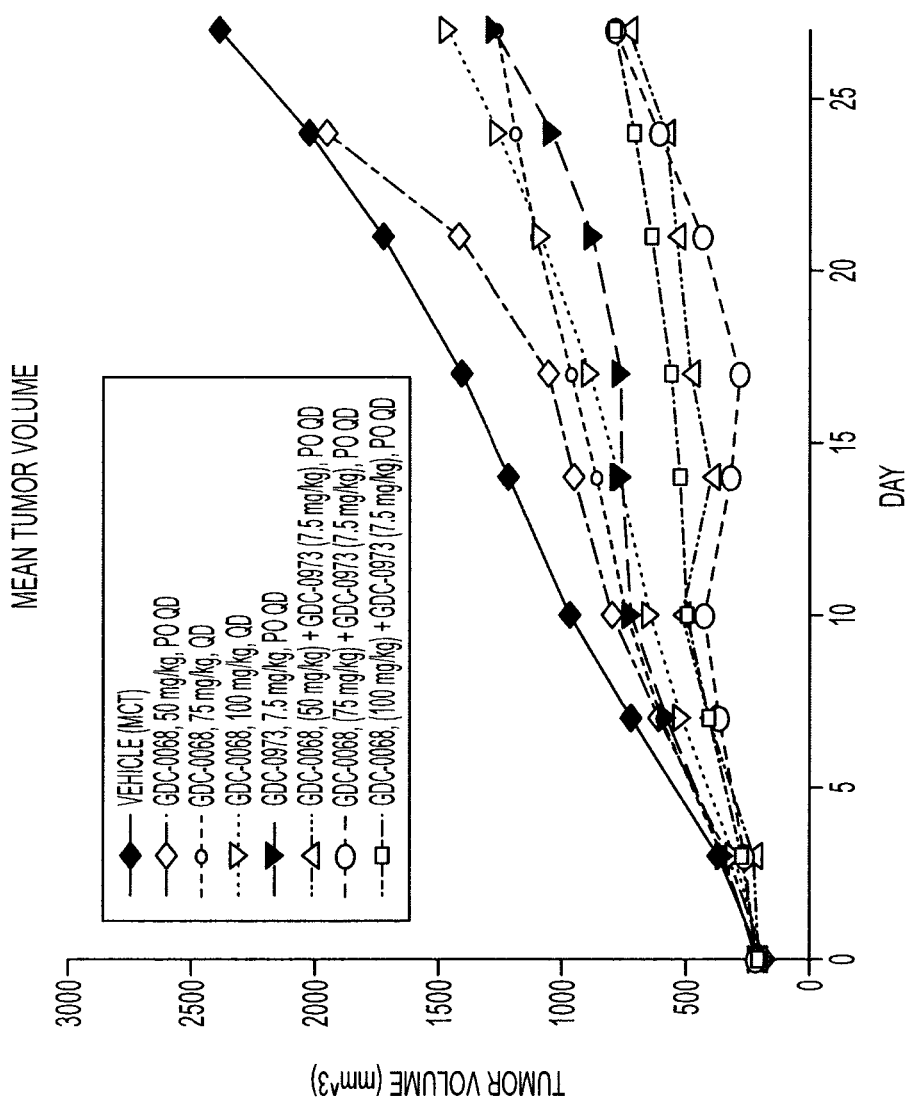
FIG. 12 illustrates results from Example 15 for the compound of Example 2 and GDC-0973 at 7.5 mg/kg.
Figure 12B:
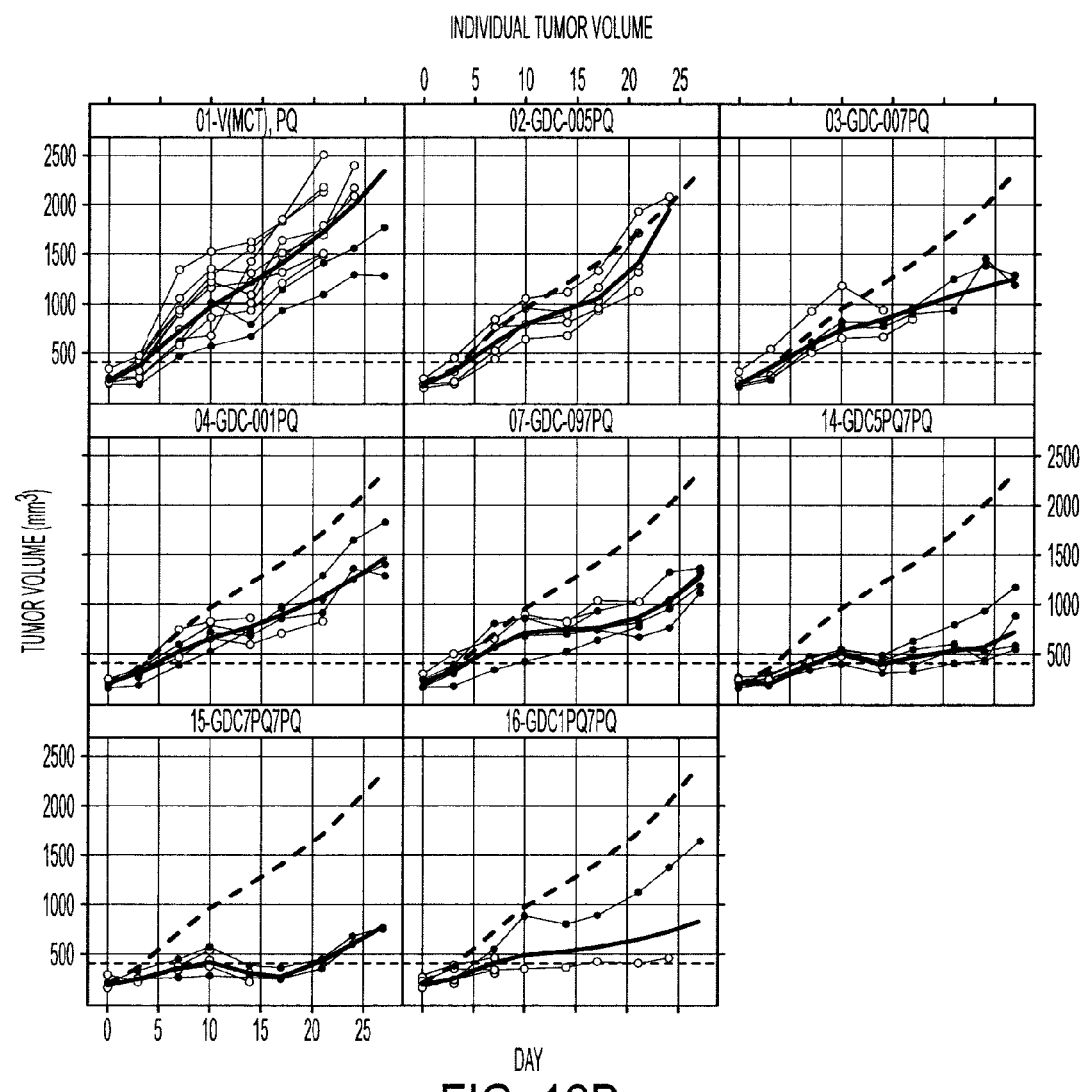
Figure 13A:
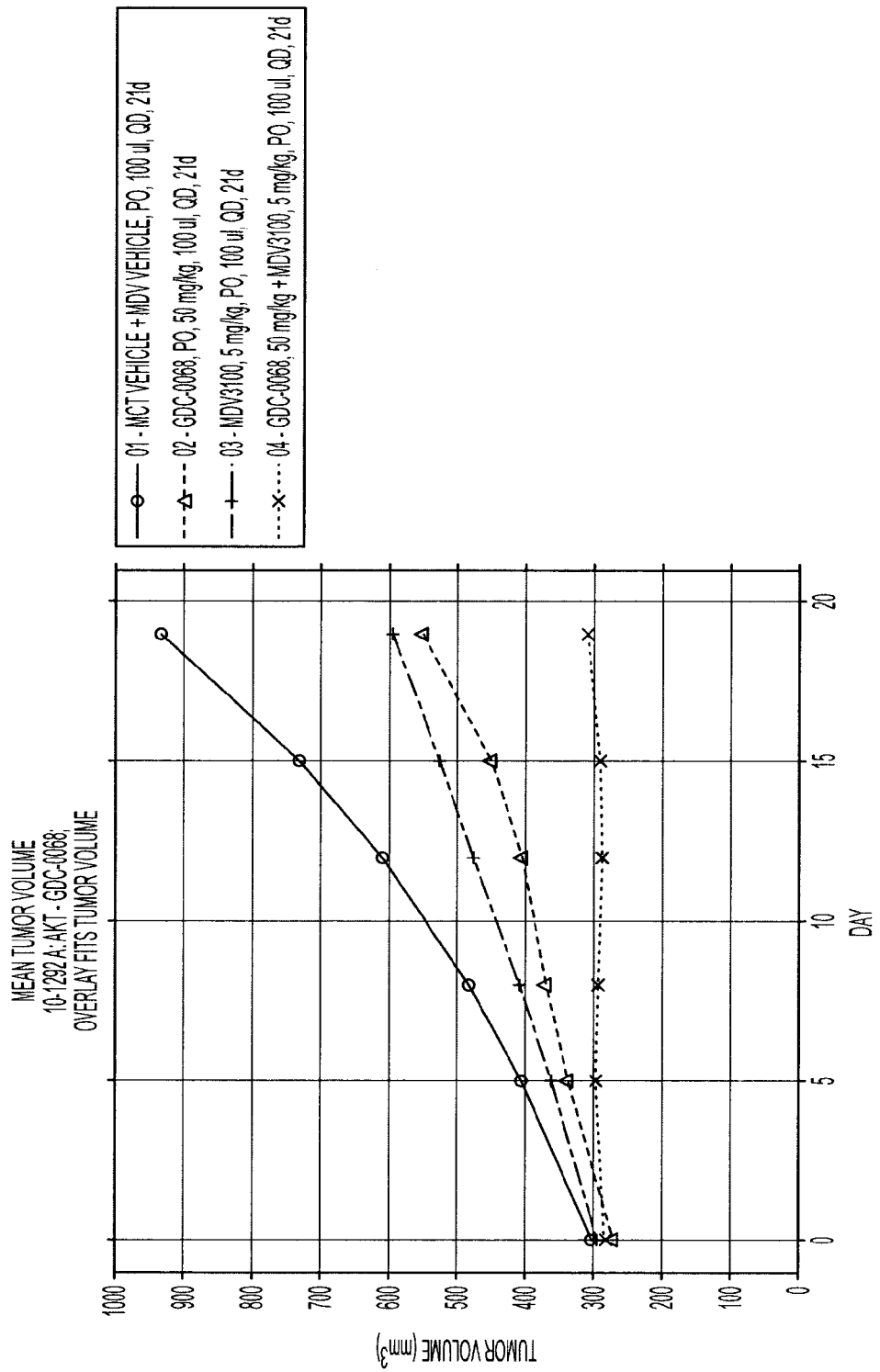
FIG. 13 illustrates results from Example 15 for the compound of Example 2 and MDV3100 in LuCap35V cells.
Figure 13B:
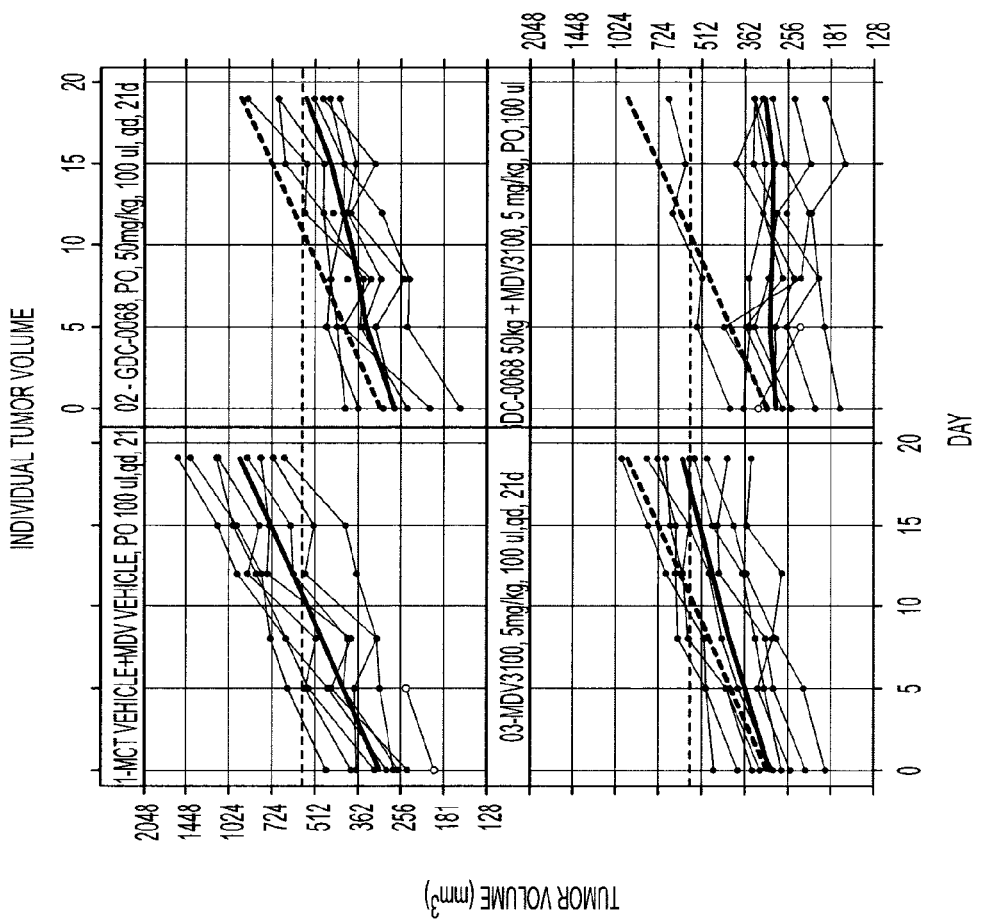
Figure 14A:
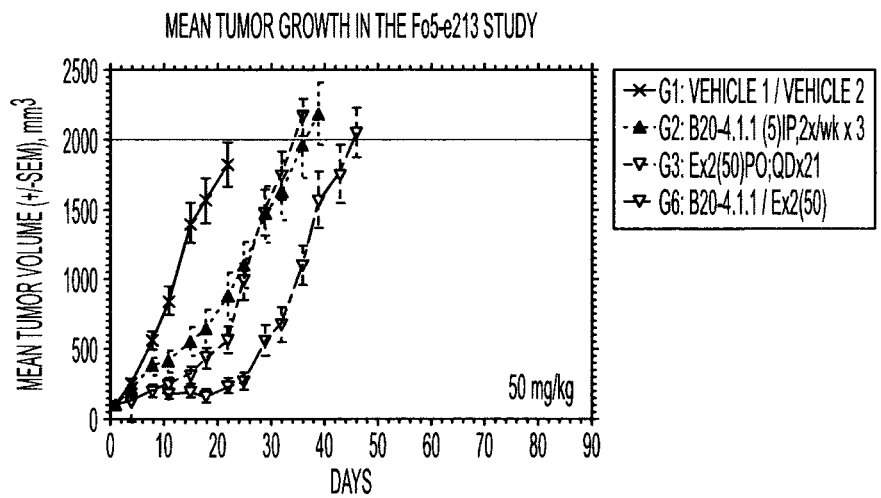
FIG. 14 illustrates results of the combination of GDC-0068 (Example 2) and B20 (murine Avastin) in a Fo5 HER2 triple positive breast cancer model (PRC), with additivity observed at 50 & 100 mg/kg of GDC-0068.
Figure 14B:
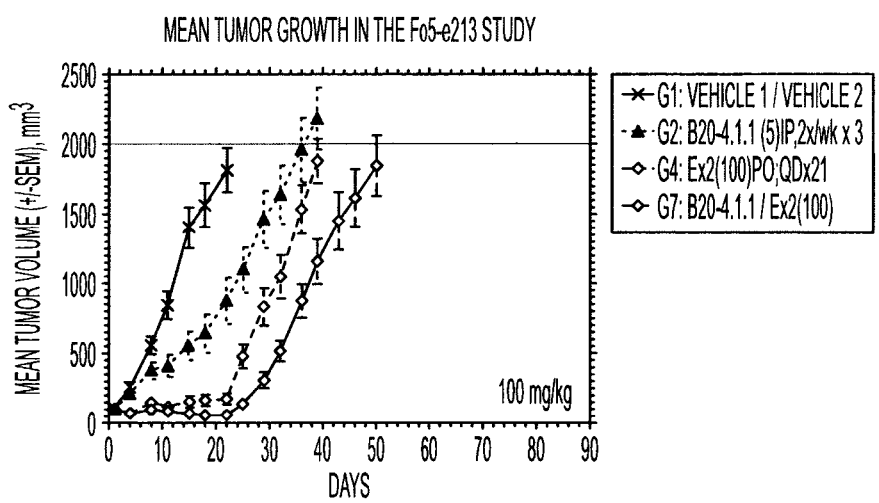
Figure 14C:
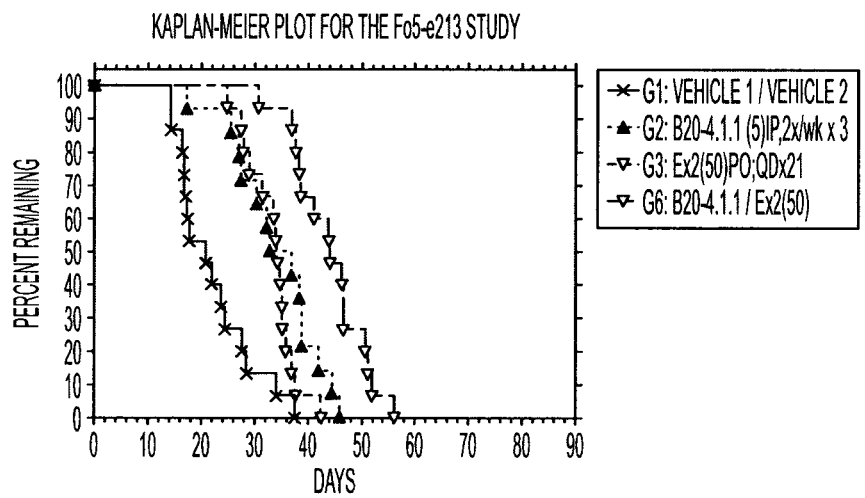
Figure 14D:
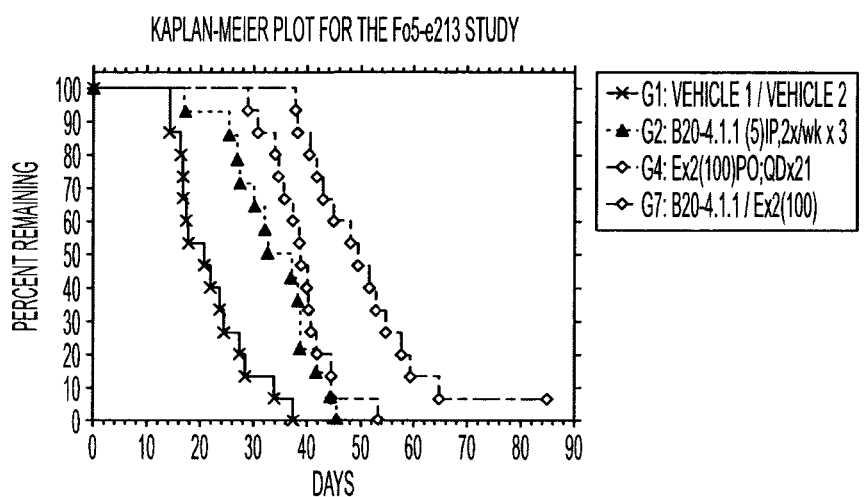

Results for representative combinations of the invention that were tested in this model are presented in FIGS. 1-9. FIG. 1 illustrates results for the compound of Example 2 and docetaxel in LuCap35V primary prostate tumors. FIG. 2 illustrates results for the compound of Example 2 dosed intermittently either PO or IP and docetaxel in PC3-NCI prostate tumors. FIG. 3 illustrates results for the compound of Example 2 dosed PO and docetaxel in PC3-NCI prostate tumors. FIG. 4 illustrates results for the compound of Example 2 dosed IP intermittently and docetaxel in MCF7-neo/HER2 tumors. FIG. 5 illustrates results for the compound of Example 2 dosed PO and docetaxel in MCF7-neo/HER2 breast tumors. FIG. 6 illustrates results for the compound of Example 2 and docetaxel in MAXF401 mammary tumors. FIG. 7 illustrates results for the compound of Example 2 and docetaxel in SKOV3 ovarian tumors. FIG. 8 illustrates results for the compound of Example 2 and cisplatnin in SKOV3 ovarian tumors. FIG. 9 illustrates results for the compound of Example 2 dosed PO and carboplatin in IGROV-1 ovarian tumors. FIG. 10 illustrates results for the compound of Example 2 and GDC-0973 at 2.5 mg/kg in H2122 NCI-NSCL tumors. FIG. 11 illustrates results for the compound of Example 2 and GDC-0973 at 5.0 mg/kg in NCI-H2122 NSCLC tumors. FIG. 12 illustrates results for the compound of Example 2 and GDC-0973 at 7.5 mg/kg in NCI-H2122 NSCLC tumors. FIG. 13 illustrates results for the compound of Example 2 and MDV3100 in LuCap35V tumors.

Figure 15B:
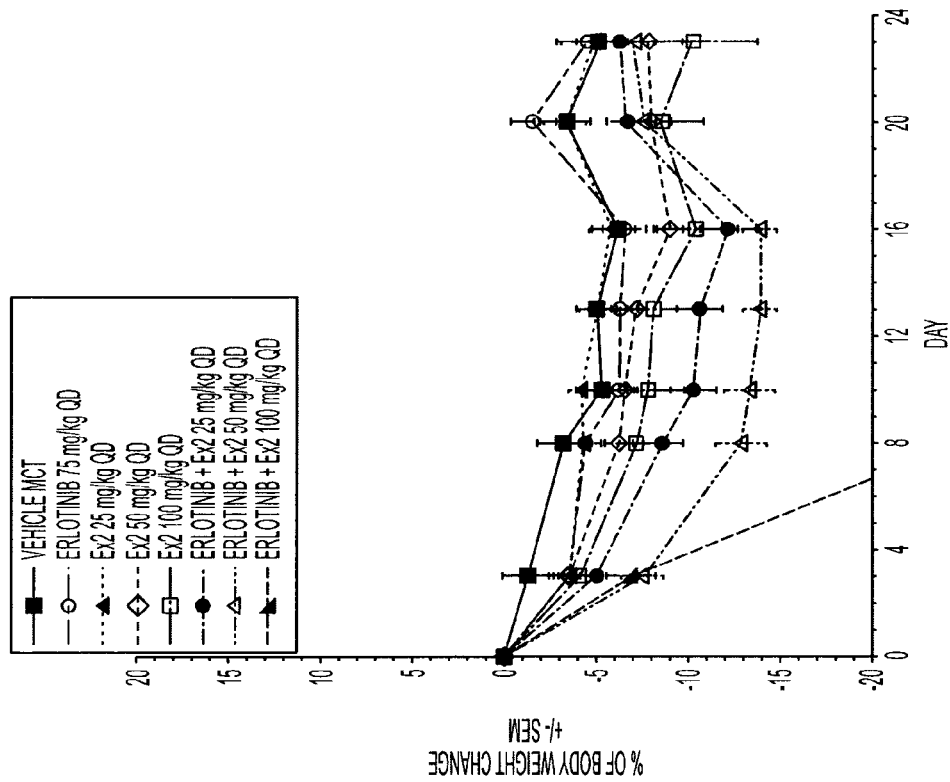
FIG. 15 illustrates results from Example 15 for the compound of Example 2 and Tarceva in NCI-H2122 (Kras mutant) cells, in which an additive effect was observed, but 100 mg/kg of Example 2 combined with erlotinib was not well tolerated.
Figure 15A:
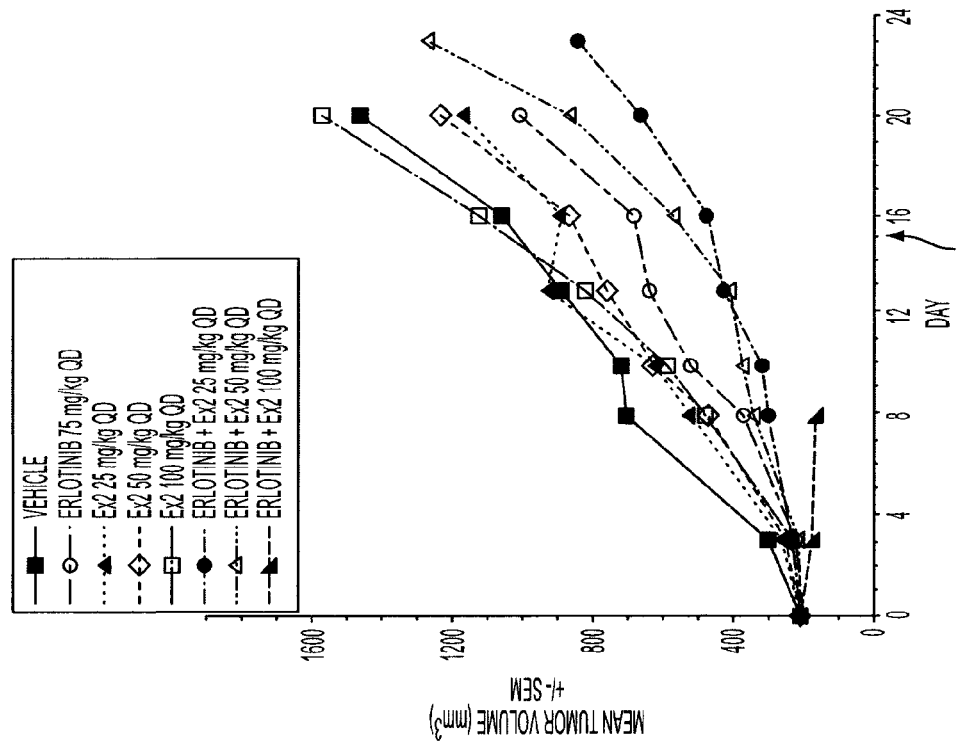

FIG. 14 illustrates results of the combination of GDC-0068 and B20 (murine Avastin) in a breast cancer model. FIG. 15 illustrates results for the compound of Example 2 and Tarceva in NCI-H2122 (Kras mutant) tumors.

Example 16

In Vitro Cell Viability (Potency) Experiments

The in vitro potency of the combinations of vemurafenib with GDC-0068 was measured by the CellTiter-Glo® Luminescent Cell Viability Assay, commercially available from Promega Corp., Madison, Wis. This homogeneous assay method determines the number of viable cells in culture based on quantitation of the ATP present, an indicator of metabolically active cells (Crouch et al (1993) J. Immunol. Meth. 160:81-88). To ascertain the role of vemurafenib with GDC-0068 in cell survival, the quantity of cytoplasmic histone-associated DNA fragments was quantified using the Cell Death Detection ELISA Plus kit (Roche, Mannheim, Germany). Both assays were conducted in 96 or 384 well format, making the assays amenable to automated high-throughput screening (HTS) (Cree et al (1995) AntiCancer Drugs 6:398-404). In some instances, the individual measured $EC_{50}$ values of vemurafenib with GDC-0068 were compared to the combination $EC_{50}$ value and a combination index score is calculated by the Chou and Talalay method (Chou, T. and Talalay, P. (1984) Adv. Enzyme Regul. 22:27-55). The strength of synergy is scored using the published ranking system. Vemurafenib-resistant cells were prepared by propagating parental A375 cells in increasing concentrations of vemurafenib to achieve resistance (Su, F., et al. Cancer Res. (2012) 72:969-978).

The data in Figures demonstrates that representative combinations provide improved results compared to the administration of the respective agents individually. For example, in the LuCap35V primary human prostate tumor model the combination of Example 2 and docetaxel resulted in tumor regressions while the single agent of either compound only resulted in tumor stasis (FIG. 1). Additionally, the combination of Example 2 and cisplatin resulted in greater tumor growth inhibition than either single agent alone in the SKOV3 ovarian human tumor model (FIG. 7).

It has been determined that certain combinations of the invention provide improved effects against certain cancer phenotypes. For example, certain combinations of the invention provide improved effects against cancers associated with PTEN mutation (or low or null status), AKT mutation (or high pAKT expression or amplification levels), PI3K mutation, or Her2/ErbB2 amplification. Accordingly, certain combinations described herein may be particularly useful against these types of cancers. For example, in gastric cancer, PTEN-loss predicts better efficacy with certain combinations of the invention (e.g., a compound of formula I with 5-FU/cisplatin), and in prostate cancer a stronger effect was seen for a combination of a compound of formula I and docetaxel in PTEN-null lines. In another example, in gastric cancer, PTEN-low predicts better efficacy with certain combinations of the invention (e.g., a compound of formula I with 5-FU/cisplatin), and in prostate cancer a stronger effect was seen for a combination of a compound of formula I and docetaxel in PTEN-low lines.

PTEN null (or low) status may be measured by any suitable means as is known in the art. In one example, IHC is used. Alternatively, Western blot analysis can be used. Antibodies to PTEN are commercially available (Cell Signaling Technology, Beverly, Mass., Cascade Biosciences, Winchester, Mass.). Example procedures for IHC and Western blot analysis for PTEN status are described in Neshat, M. S. et al. Enhanced sensitivity of PTEN-deficient tumors to inhibition of FRAP/mTOR, *Proc. Natl Acad. Sci. USA* 98, 10314-10319 (2001) and Perren, A., et. al. Immunohistochemical Evidence of Loss of PTEN Expression in Primary Ductal Adenocarcinomas of the Breast, *American Journal of Pathology*, Vol. 155, No. 4, October 1999. Additionally, cancers associated with AKT mutation, PI3K mutation, and with Her2/ErbB2 amplification can be identified using techniques that are known in the art.

The level of activation or phosphorylation of AKT ("pAKT") compared to the level of non-activated or non-phosphorylated AKT in a given sample can be measured by methods known in the art. The pAKT status can be expressed in terms of a ratio (e.g., amount of pAKT in a tumor cell divided by amount pAKT in a non-tumorous cell of the same type) or a subtraction (e.g., amount of pAKT in a tumor cell minus amount pAKT in the cell or in a non-tumorous cell of the same type). The pAKT profile can also be expressed in terms of the level of activation of the pathway by measuring amounts of phosphorylated downstream targets of AKT (for example, pGSK or PRAS40). A high pAKT refers to activation or phosphorylation levels of overall AKT in the sample that are higher than a baseline value. In one example, the baseline value is the basal levels of pAKT for a given cell type. In another example, the baseline value is average or mean level of pAKT in a given population of sample cells, for example non-cancerous or cells. In another example, a high pAKT refers to a tumor cell that over-expresses or -amplified phosphorylated or activated AKT in the cell, when compared to an average of normal, healthy (e.g., non-tumorous) cells of the same type from either the same mammal or a patient population. The pAKT profile can also be used in conjunction with other markers, for example FOXO3a localization profiles, for predicting efficacy of certain PI3k/AKT kinase pathway inhibitors, or for example with BRAF V600E mutation status, to predict efficacy of certain combinations of compounds of formula I with vemurafenib, particularly in patients with vemerafenib resistant cancers, such as metastatic or unresectable melanoma. Kits for measuring pAKT in tissue samples are commercially available (e.g., phospho-Akt (Thr308) STAR ELISA kit, EMD Millipore)

In one specific aspect, the invention provides a method for treating a patient having a cancer that is associated with PTEN mutation or loss of expression, AKT mutation or amplification, PI3K mutation or amplification, or Her2/ErbB2 amplification comprising administering a combination of the invention to the patient. In another aspect, the invention provides a method for identifying a patient having a cancer that that can be treated with a combination of the invention comprising determining if the patient's cancer is associated with PTEN mutation or loss of expression, AKT mutation or amplification, PI3K mutation or amplification, or Her2/ErbB2 amplification, wherein association of the patient's cancer with PTEN mutation or loss of expression, AKT mutation or amplification, PI3K mutation or amplification, or Her2/ErbB2 amplification is indicative of a cancer that can be treated with a combination of the invention. In a further aspect, the invention provides a method further comprising treating the patient so identified with a combination of the invention.

Further, since numerous modifications and changes will be readily apparent to those skilled in the art, it is not desired to limit the invention to the exact construction and process shown as described above. Accordingly, all suitable modifications and equivalents may be considered to fall within the scope as defined by the claims that follow.

We claim:

1. A combination of a) a compound of Formula Ia:

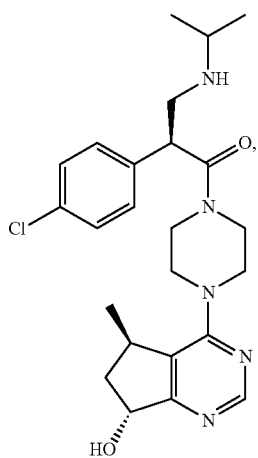

or a pharmaceutically acceptable salt thereof, and b) vemurafenib or a pharmaceutically acceptable salt thereof for the prophylactic or therapeutic treatment of a hyperproliferative disorder.

2. A method for treating a hyperproliferative disorder in a mammal comprising, administering to the mammal, a) a compound of formula Ia or a pharmaceutically acceptable salt thereof as defined in claim 1; and b) vemurafenib or a pharmaceutically acceptable salt thereof.

3. The method of claim 2, wherein the hyperproliferative disorder is cancer.

4. The method of claim 3 wherein the cancer comprises a BRAF V600E mutation.

5. The method of claim 3 wherein the cancer is associated with high pAKT expression or activation levels.

6. The method of claim 3, wherein the cancer is lymphoma, colon, melanoma, thyroid or lung cancer.

7. The method of claim 6 wherein the cancer is resistant to vemurafenib single agent therapy.

8. The method of claim 7 wherein the cancer is metastatic or unresectable melanoma.

9. The method of claim 2, wherein the combination provides a synergistic effect in treating the disorder.

10. The method of claim 2, wherein the compound of formula Ia or the salt thereof is administered simultaneously with the vemurafenib or the salt thereof.

11. The method of claim 2, wherein the compound of formula Ia or the salt and the vemurafenib or the salt thereof are administered sequentially.

12. The method of claim 2, wherein the patient previously received vemurafenib single agent therapy.

13. The method of claim 2, wherein the compound of formula Ia or the salt thereof is administered separately from the vemurafenib or the salt thereof.

14. A kit comprising a compound of formula Ia or a pharmaceutically acceptable salt thereof as defined in claim 1, vemurafenib or a pharmaceutically acceptable salt thereof, a container, and a package insert or label indicating the administration of the compound of formula Ia with vemurafenib or a pharmaceutically acceptable salt thereof for treating a hyperproliferative disorder.

* * * * *